US010159714B2

(12) United States Patent
Leung

(10) Patent No.: US 10,159,714 B2
(45) Date of Patent: Dec. 25, 2018

(54) COMPOSITIONS, DEVICES AND METHODS OF USE THEREOF FOR THE TREATMENT OF CANCERS

(71) Applicant: Intarcia Therapeutics, Inc., Boston, MA (US)

(72) Inventor: Karling Alice Leung, Oakland, CA (US)

(73) Assignee: Intarcia Therapeutics, Inc., Boston, MA (US)

( * ) Notice: Subject to any disclaimer, the term of this patent is extended or adjusted under 35 U.S.C. 154(b) by 0 days.

(21) Appl. No.: 15/597,788

(22) Filed: May 17, 2017

(65) Prior Publication Data
US 2017/0252409 A1 Sep. 7, 2017

Related U.S. Application Data

(63) Continuation of application No. 14/525,201, filed on Oct. 27, 2014, now abandoned, which is a continuation of application No. 13/372,326, filed on Feb. 13, 2012, now abandoned.

(60) Provisional application No. 61/443,628, filed on Feb. 16, 2011.

(51) Int. Cl.
| A61K 38/26 | (2006.01) |
| C07K 14/605 | (2006.01) |
| A61M 31/00 | (2006.01) |
| A61K 45/06 | (2006.01) |
| A61M 37/00 | (2006.01) |

(52) U.S. Cl.
CPC .............. *A61K 38/26* (2013.01); *A61K 45/06* (2013.01); *A61M 31/002* (2013.01); *C07K 14/605* (2013.01); *A61M 37/00* (2013.01)

(58) Field of Classification Search
None
See application file for complete search history.

(56) References Cited

U.S. PATENT DOCUMENTS

| 2,110,208 A | 3/1938 | Eggert |
| 2,168,437 A | 8/1939 | Buercklin |
| 2,531,724 A | 11/1950 | Cevasco |
| D179,537 S | 1/1957 | Floyd et al. |
| 3,025,991 A | 3/1962 | Gillon |
| 3,122,162 A | 2/1964 | Sands |
| 3,523,906 A | 8/1970 | Vrancken et al. |
| 3,625,214 A | 12/1971 | Higuchi |
| 3,632,768 A | 1/1972 | Bergy et al. |
| 3,691,090 A | 9/1972 | Kitajima et al. |
| D226,915 S | 5/1973 | Huggins |
| 3,732,865 A | 5/1973 | Higuchi et al. |
| 3,737,337 A | 6/1973 | Schnoring et al. |
| 3,773,919 A | 11/1973 | Boswell et al. |
| 3,797,492 A | 3/1974 | Place |
| 3,869,549 A | 3/1975 | Geller |
| 3,891,570 A | 6/1975 | Fukushima et al. |
| D236,035 S | 7/1975 | Ciencewicki |
| 3,960,757 A | 6/1976 | Morishita et al. |
| 3,987,790 A | 10/1976 | Eckenhoff et al. |
| 3,995,631 A | 12/1976 | Higuchi et al. |
| 3,995,632 A | 12/1976 | Nakano et al. |
| 4,008,719 A | 2/1977 | Theeuwes et al. |
| 4,034,756 A | 7/1977 | Higuchi et al. |
| 4,078,060 A | 3/1978 | Benson et al. |
| 4,111,201 A | 9/1978 | Theeuwes |
| 4,111,202 A | 9/1978 | Theeuwes |
| 4,111,203 A | 9/1978 | Theeuwes |
| 4,203,439 A | 5/1980 | Theeuwes |
| 4,211,771 A | 7/1980 | Witkowski et al. |
| 4,221,862 A | 9/1980 | Naito et al. |
| 4,243,030 A | 1/1981 | Lynch et al. |
| D258,837 S | 4/1981 | Spranger et al. |
| D259,458 S | 6/1981 | Fuller et al. |
| 4,305,927 A | 12/1981 | Theeuwes et al. |
| 4,310,516 A | 1/1982 | Chang et al. |
| 4,340,054 A | 7/1982 | Michaels |
| 4,350,271 A | 9/1982 | Eckenhoff |
| 4,373,527 A | 2/1983 | Fischell |
| 4,376,118 A | 3/1983 | Daher et al. |
| 4,384,975 A | 5/1983 | Fong |
| 4,389,330 A | 6/1983 | Tice et al. |
| 4,439,196 A | 3/1984 | Higuchi |
| 4,444,498 A | 4/1984 | Heinemann |
| 4,455,143 A | 6/1984 | Theeuwes et al. |
| 4,455,145 A | 6/1984 | Theeuwes |
| 4,530,840 A | 7/1985 | Tice et al. |
| 4,552,561 A | 11/1985 | Eckenhoff et al. |
| 4,588,614 A | 5/1986 | Lauchenauer |
| 4,594,108 A | 6/1986 | Greminger, Jr. et al. |
| 4,609,374 A | 9/1986 | Ayer |
| 4,639,244 A | 1/1987 | Rizk et al. |
| 4,655,462 A | 4/1987 | Balsells |
| 4,673,405 A | 6/1987 | Guittard et al. |
| 4,675,184 A | 6/1987 | Hasegawa et al. |

(Continued)

FOREIGN PATENT DOCUMENTS

| EP | 0052510 A2 | 5/1982 |
| EP | 0079405 | 5/1983 |

(Continued)

OTHER PUBLICATIONS

Adolf, "Human interferon omega-a review," Mult. Sclr. 1:S44-47 (1995).

(Continued)

Primary Examiner — Satyanarayana R Gudibande
(74) Attorney, Agent, or Firm — Brian C. Trinque; Lathrop Gage LLP

(57) ABSTRACT

The use of GLP-1 receptor agonists, such as glucagon-like peptide-1 (GLP-1) or exenatide, for the treatment of cancer is described. The GLP-1 receptor agonists are typically delivered using an implanted osmotic delivery device that provides for continuous delivery of the GLP-1 receptor agonist for at least one month. Additional beneficial agents, such as anticancer agents, can also be administered.

8 Claims, 2 Drawing Sheets

Specification includes a Sequence Listing.

(56) References Cited

U.S. PATENT DOCUMENTS

| | | |
|---|---|---|
| 4,695,623 A | 9/1987 | Stabinsky |
| 4,727,138 A | 2/1988 | Goeddel et al. |
| 4,734,284 A | 3/1988 | Terada et al. |
| 4,737,437 A | 4/1988 | Gutsell, Jr. et al. |
| 4,743,449 A | 5/1988 | Yoshida et al. |
| 4,753,651 A | 6/1988 | Eckenhoff |
| 4,762,791 A | 8/1988 | Goeddel et al. |
| 4,765,989 A | 8/1988 | Wong et al. |
| 4,783,337 A | 11/1988 | Wong et al. |
| 4,818,517 A | 4/1989 | Kwee et al. |
| 4,820,638 A | 4/1989 | Swetly et al. |
| 4,826,144 A | 5/1989 | Balsells |
| 4,830,344 A | 5/1989 | Balsells |
| 4,840,896 A | 6/1989 | Reddy et al. |
| 4,845,196 A | 7/1989 | Cowling |
| 4,847,079 A | 7/1989 | Kwan |
| 4,851,228 A | 7/1989 | Zentner et al. |
| 4,865,845 A | 9/1989 | Eckenhoff et al. |
| 4,873,080 A | 10/1989 | Brickl et al. |
| 4,874,388 A | 10/1989 | Wong et al. |
| 4,876,781 A | 10/1989 | Balsells |
| 4,885,166 A | 12/1989 | Meyer et al. |
| 4,886,668 A | 12/1989 | Haslam et al. |
| 4,892,778 A | 1/1990 | Theeuwes et al. |
| 4,893,795 A | 1/1990 | Balsells |
| 4,897,471 A | 1/1990 | Stabinsky |
| 4,907,788 A | 3/1990 | Balsells |
| 4,915,366 A | 4/1990 | Balsells |
| 4,915,949 A | 4/1990 | Wong et al. |
| 4,915,954 A | 4/1990 | Ayer et al. |
| 4,917,887 A | 4/1990 | Hauptmann et al. |
| 4,917,895 A | 4/1990 | Lee et al. |
| 4,923,805 A | 5/1990 | Reddy et al. |
| 4,927,687 A | 5/1990 | Nuwayser |
| 4,929,554 A | 5/1990 | Goeddel et al. |
| 4,931,285 A | 6/1990 | Edgren et al. |
| 4,934,666 A | 6/1990 | Balsells |
| 4,940,465 A | 7/1990 | Theeuwes et al. |
| 4,940,588 A | 7/1990 | Sparks et al. |
| 4,952,402 A | 8/1990 | Sparks et al. |
| 4,957,119 A | 9/1990 | de Nijs |
| 4,961,253 A | 10/1990 | Balsells |
| 4,964,204 A | 10/1990 | Balsells |
| 4,969,884 A | 11/1990 | Yum |
| 4,974,821 A | 12/1990 | Balsells |
| 4,976,966 A | 12/1990 | Theeuwes et al. |
| 5,004,689 A | 4/1991 | Fiers et al. |
| 5,006,346 A | 4/1991 | Theeuwes et al. |
| 5,019,382 A | 5/1991 | Cummins, Jr. |
| 5,019,400 A | 5/1991 | Gombotz et al. |
| 5,023,088 A | 6/1991 | Wong et al. |
| 5,024,842 A | 6/1991 | Edgren et al. |
| 5,030,216 A | 7/1991 | Theeuwes et al. |
| 5,034,229 A | 7/1991 | Magruder et al. |
| 5,057,318 A | 10/1991 | Magruder et al. |
| 5,059,423 A | 10/1991 | Magruder et al. |
| 5,066,436 A | 11/1991 | Komen et al. |
| 5,071,642 A | 12/1991 | Lahr et al. |
| 5,072,070 A | 12/1991 | Balsells |
| 5,079,388 A | 1/1992 | Balsells |
| 5,091,188 A | 2/1992 | Haynes |
| 5,108,078 A | 4/1992 | Balsells |
| 5,110,596 A | 5/1992 | Magruder et al. |
| 5,112,614 A | 5/1992 | Magruder et al. |
| 5,113,938 A | 5/1992 | Clayton |
| 5,117,066 A | 5/1992 | Balsells |
| D326,718 S | 6/1992 | Maxwell |
| 5,118,666 A | 6/1992 | Habener |
| 5,120,306 A | 6/1992 | Gosselin |
| 5,120,712 A | 6/1992 | Habener |
| 5,120,832 A | 6/1992 | Goeddel et al. |
| 5,122,128 A | 6/1992 | Cardinal et al. |
| 5,122,377 A | 6/1992 | Miller |
| 5,126,142 A | 6/1992 | Ayer et al. |
| 5,126,147 A | 6/1992 | Silvestri et al. |
| 5,134,244 A | 7/1992 | Balsells |
| 5,137,727 A | 8/1992 | Eckenhoff |
| D329,278 S | 9/1992 | Gallup |
| 5,151,093 A | 9/1992 | Theeuwes et al. |
| 5,160,122 A | 11/1992 | Balsells |
| 5,160,743 A | 11/1992 | Edgren et al. |
| 5,161,806 A | 11/1992 | Balsells |
| 5,180,591 A | 1/1993 | Margruder et al. |
| 5,190,765 A | 3/1993 | Jao et al. |
| 5,203,849 A | 4/1993 | Balsells |
| 5,204,108 A | 4/1993 | Illum |
| 5,207,752 A | 5/1993 | Sorensen et al. |
| 5,209,746 A | 5/1993 | Balaban et al. |
| 5,213,809 A | 5/1993 | Wright et al. |
| 5,213,810 A | 5/1993 | Steber |
| 5,219,572 A | 6/1993 | Sivaramakrishnan |
| 5,221,278 A | 6/1993 | Linkwitz et al. |
| 5,223,265 A | 6/1993 | Wong |
| 5,225,205 A | 7/1993 | Orsolini |
| 5,231,176 A | 7/1993 | Goeddel et al. |
| 5,234,424 A | 8/1993 | Yum et al. |
| 5,234,692 A | 8/1993 | Magruder et al. |
| 5,234,693 A | 8/1993 | Magruder et al. |
| 5,234,695 A | 8/1993 | Hobbs et al. |
| 5,252,338 A | 10/1993 | Jao et al. |
| 5,260,069 A | 11/1993 | Chen |
| D342,855 S | 1/1994 | Butler, II |
| 5,278,151 A | 1/1994 | Korb et al. |
| 5,279,608 A | 1/1994 | Cherif Cheikh |
| 5,284,655 A | 2/1994 | Bogdansky et al. |
| 5,288,501 A | 2/1994 | Nürnberg et al. |
| 5,288,502 A | 2/1994 | Mcginity et al. |
| 5,290,271 A | 3/1994 | Jernberg |
| 5,300,079 A | 4/1994 | Niezink et al. |
| 5,300,302 A | 4/1994 | Tachon et al. |
| 5,308,348 A | 5/1994 | Balaban et al. |
| 5,312,335 A | 5/1994 | McKinnon et al. |
| 5,312,389 A | 5/1994 | Theeuwes et al. |
| 5,312,390 A | 5/1994 | Wong |
| 5,318,558 A | 6/1994 | Linkwitz et al. |
| 5,318,780 A | 6/1994 | Viegas et al. |
| 5,320,616 A | 6/1994 | Magndu et al. |
| 5,324,280 A | 6/1994 | Wong et al. |
| 5,336,057 A | 8/1994 | Fukuda et al. |
| 5,336,505 A | 8/1994 | Ng et al. |
| 5,352,662 A | 10/1994 | Brooks et al. |
| 5,368,588 A | 11/1994 | Bettinger |
| 5,368,863 A | 11/1994 | Eckenhoff et al. |
| 5,371,089 A | 12/1994 | Rattan |
| 5,374,620 A | 12/1994 | Clark et al. |
| 5,385,738 A | 1/1995 | Yamahira et al. |
| 5,385,887 A | 1/1995 | Yim et al. |
| 5,407,609 A | 4/1995 | Tice et al. |
| D358,644 S | 5/1995 | Park |
| 5,411,951 A | 5/1995 | Mitchell |
| 5,413,572 A | 5/1995 | Wong et al. |
| 5,413,672 A | 5/1995 | Hirotsuji et al. |
| 5,424,286 A | 6/1995 | Eng |
| 5,428,024 A | 6/1995 | Chu et al. |
| 5,429,602 A | 7/1995 | Hauser |
| 5,439,688 A | 8/1995 | Orsolini et al. |
| 5,443,459 A | 8/1995 | Wong et al. |
| 5,445,829 A | 8/1995 | Paradissis et al. |
| 5,456,679 A | 10/1995 | Balaban et al. |
| 5,458,888 A | 10/1995 | Chen |
| 5,464,929 A | 11/1995 | Bezwada et al. |
| 5,472,708 A | 12/1995 | Chen |
| 5,478,564 A | 12/1995 | Wantier et al. |
| 5,486,365 A | 1/1996 | Takado et al. |
| 5,498,255 A | 3/1996 | Wong et al. |
| 5,511,355 A | 4/1996 | Dingler |
| 5,512,293 A | 4/1996 | Landrau et al. |
| 5,512,549 A | 4/1996 | Chen et al. |
| 5,514,110 A | 5/1996 | Teh |
| 5,529,914 A | 6/1996 | Hubbell et al. |
| 5,531,736 A | 7/1996 | Wong et al. |
| 5,540,665 A | 7/1996 | Mercado et al. |
| 5,540,912 A | 7/1996 | Roorda et al. |
| 5,541,172 A | 7/1996 | Labrie et al. |

(56) References Cited

U.S. PATENT DOCUMENTS

| | | |
|---|---|---|
| 5,542,682 A | 8/1996 | Goldstein et al. |
| 5,543,156 A | 8/1996 | Roorda et al. |
| 5,545,618 A | 8/1996 | Buckley et al. |
| 5,556,642 A | 9/1996 | Kobayashi et al. |
| 5,557,318 A | 9/1996 | Gabriel |
| 5,571,525 A | 11/1996 | Roorda et al. |
| 5,574,008 A | 11/1996 | Johnson et al. |
| 5,574,137 A | 11/1996 | Gray et al. |
| 5,580,578 A | 12/1996 | Oshlack et al. |
| 5,589,167 A | 12/1996 | Cleland et al. |
| 5,595,751 A | 1/1997 | Bezwada |
| 5,595,759 A | 1/1997 | Wright et al. |
| 5,597,579 A | 1/1997 | Bezwada et al. |
| 5,602,010 A | 2/1997 | Hauptmann et al. |
| 5,605,688 A | 2/1997 | Himmler et al. |
| 5,607,687 A | 3/1997 | Bezwada et al. |
| 5,609,885 A | 3/1997 | Rivera et al. |
| 5,614,221 A | 3/1997 | Fjellstrom |
| 5,614,492 A | 3/1997 | Habener |
| 5,618,552 A | 4/1997 | Bezwada et al. |
| 5,620,698 A | 4/1997 | Bezwada et al. |
| 5,620,705 A | 4/1997 | Dong et al. |
| 5,630,796 A | 5/1997 | Bellhouse et al. |
| 5,633,011 A | 5/1997 | Dong et al. |
| 5,635,213 A | 6/1997 | Nystrom et al. |
| 5,639,477 A | 6/1997 | Maruyama et al. |
| 5,639,640 A | 6/1997 | Reddy et al. |
| 5,645,850 A | 7/1997 | Bezwada et al. |
| 5,648,088 A | 7/1997 | Bezwada et al. |
| 5,650,173 A | 7/1997 | Ramstack et al. |
| 5,654,008 A | 8/1997 | Herbert et al. |
| 5,654,010 A | 8/1997 | Johnson et al. |
| 5,656,297 A | 8/1997 | Bernstein et al. |
| 5,656,299 A | 8/1997 | Kino et al. |
| 5,658,593 A | 8/1997 | Orly et al. |
| 5,660,847 A | 8/1997 | Magruder et al. |
| 5,660,858 A | 8/1997 | Parikh et al. |
| 5,660,861 A | 8/1997 | Jao et al. |
| 5,667,808 A | 9/1997 | Johnson et al. |
| 5,668,170 A | 9/1997 | Gyory |
| 5,672,549 A | 9/1997 | Minami et al. |
| 5,676,942 A | 10/1997 | Testa et al. |
| 5,686,097 A | 11/1997 | Taskovich et al. |
| 5,688,801 A | 11/1997 | Mesens et al. |
| 5,690,925 A | 11/1997 | Gray et al. |
| 5,690,952 A | 11/1997 | Magruder et al. |
| 5,697,113 A | 12/1997 | Shatz et al. |
| 5,698,213 A | 12/1997 | Jamiolkowski et al. |
| 5,700,486 A | 12/1997 | Canal et al. |
| 5,700,583 A | 12/1997 | Jamiolkowski et al. |
| 5,703,200 A | 12/1997 | Bezwada et al. |
| 5,707,644 A | 1/1998 | Illum |
| 5,711,967 A | 1/1998 | Juch |
| 5,713,847 A | 2/1998 | Howard, III et al. |
| 5,718,922 A | 2/1998 | Herrero-Vanrell |
| 5,728,088 A | 3/1998 | Margruder et al. |
| 5,728,396 A | 3/1998 | Peery et al. |
| 5,733,572 A | 3/1998 | Unger et al. |
| 5,736,159 A | 4/1998 | Chen et al. |
| 5,738,845 A | 4/1998 | Imakawa |
| 5,747,058 A | 5/1998 | Tipton et al. |
| 5,756,450 A | 5/1998 | Lorenz et al. |
| 5,767,251 A | 6/1998 | Reddy et al. |
| 5,770,231 A | 6/1998 | Mesens et al. |
| 5,782,396 A | 7/1998 | Mastri et al. |
| 5,792,477 A | 8/1998 | Rickey et al. |
| 5,795,591 A | 8/1998 | Lee et al. |
| 5,795,779 A | 8/1998 | McCormick et al. |
| 5,807,876 A | 9/1998 | Armistead et al. |
| 5,814,323 A | 9/1998 | Lyle |
| D399,821 S | 10/1998 | Tyneski et al. |
| 5,817,129 A | 10/1998 | Labrecque et al. |
| 5,830,501 A | 11/1998 | Dong et al. |
| 5,836,935 A | 11/1998 | Ashton et al. |
| 5,843,891 A | 12/1998 | Sherman |
| 5,844,017 A | 12/1998 | Jamiolkowski et al. |
| 5,851,451 A | 12/1998 | Takechi et al. |
| 5,858,746 A | 1/1999 | Hubbell et al. |
| 5,859,150 A | 1/1999 | Jamiolkowski et al. |
| 5,861,166 A | 1/1999 | Eckenhoff |
| 5,871,770 A | 2/1999 | Margruder et al. |
| 5,871,778 A | 2/1999 | Kino et al. |
| 5,874,388 A | 2/1999 | Hsu |
| 5,876,746 A | 3/1999 | Jona et al. |
| 5,882,676 A | 3/1999 | Lee et al. |
| D408,917 S | 4/1999 | Hacker |
| 5,904,935 A | 5/1999 | Eckenhoff et al. |
| 5,906,816 A | 5/1999 | Soos et al. |
| 5,906,830 A | 5/1999 | Farinas et al. |
| 5,908,621 A | 6/1999 | Glue et al. |
| 5,916,598 A | 6/1999 | Rickey et al. |
| 5,922,253 A | 7/1999 | Herbert et al. |
| 5,928,666 A | 7/1999 | Farinas et al. |
| 5,932,547 A | 8/1999 | Stevenson et al. |
| 5,938,654 A | 8/1999 | Wong et al. |
| 5,939,286 A | 8/1999 | Johnson et al. |
| 5,942,223 A | 8/1999 | Bazer et al. |
| 5,942,253 A | 8/1999 | Gombotz et al. |
| 5,945,126 A | 8/1999 | Thanoo et al. |
| 5,948,430 A | 9/1999 | Zerbe et al. |
| 5,958,909 A | 9/1999 | Habener |
| D415,073 S | 10/1999 | Meehan et al. |
| 5,962,023 A | 10/1999 | Jamiolkowski et al. |
| 5,965,168 A | 10/1999 | Mesens et al. |
| 5,972,370 A | 10/1999 | Eckenhoff et al. |
| 5,972,373 A | 10/1999 | Yajima et al. |
| 5,976,109 A | 11/1999 | Heruth |
| 5,980,945 A | 11/1999 | Ruiz |
| 5,981,719 A | 11/1999 | Woiszwillo et al. |
| 5,984,890 A | 11/1999 | Gast et al. |
| 5,985,305 A | 11/1999 | Peery et al. |
| 5,989,463 A | 11/1999 | Tracy et al. |
| 5,997,527 A | 12/1999 | Gumucio et al. |
| 5,997,902 A | 12/1999 | Maruyama et al. |
| 6,007,805 A | 12/1999 | Foster et al. |
| 6,017,545 A | 1/2000 | Modi |
| 6,022,561 A | 2/2000 | Carlsson et al. |
| 6,023,802 A | 2/2000 | King |
| 6,029,361 A | 2/2000 | Newman |
| 6,056,718 A | 5/2000 | Funderburk et al. |
| 6,060,450 A | 5/2000 | Soos et al. |
| 6,069,133 A | 5/2000 | Carlo et al. |
| 6,074,660 A | 6/2000 | Jamiolkowski et al. |
| 6,074,673 A | 6/2000 | Guillen |
| 6,100,346 A | 8/2000 | Jamiolkowski et al. |
| 6,110,503 A | 8/2000 | Rickey et al. |
| 6,113,938 A | 9/2000 | Chen et al. |
| 6,113,947 A | 9/2000 | Cleland et al. |
| 6,120,787 A | 9/2000 | Gustafsson et al. |
| 6,124,261 A | 9/2000 | Stevenson et al. |
| 6,124,281 A | 9/2000 | Lewis et al. |
| 6,127,520 A | 10/2000 | Ueda et al. |
| 6,129,761 A | 10/2000 | Hubbell |
| 6,130,200 A | 10/2000 | Brodbeck et al. |
| 6,132,420 A | 10/2000 | Dionne et al. |
| 6,133,249 A | 10/2000 | Hills |
| 6,133,429 A | 10/2000 | Davis et al. |
| 6,147,168 A | 11/2000 | Jamiolkowski et al. |
| 6,156,331 A | 12/2000 | Peery et al. |
| 6,172,046 B1 | 1/2001 | Albrecht |
| 6,174,547 B1 | 1/2001 | Dong et al. |
| 6,177,096 B1 | 1/2001 | Zerbe et al. |
| 6,183,461 B1 | 2/2001 | Matsuura et al. |
| 6,187,095 B1 | 2/2001 | Labrecque et al. |
| 6,190,350 B1 | 2/2001 | Davis et al. |
| 6,190,700 B1 | 2/2001 | Okada et al. |
| 6,190,702 B1 | 2/2001 | Takada et al. |
| 6,191,102 B1 | 2/2001 | DiMarchi et al. |
| 6,204,022 B1 | 3/2001 | Johnson et al. |
| 6,217,893 B1 | 4/2001 | Pellet et al. |
| 6,217,906 B1 | 4/2001 | Gumucio et al. |
| 6,217,908 B1 | 4/2001 | Mathiowitz et al. |
| 6,218,431 B1 | 4/2001 | Schoen et al. |
| 6,224,894 B1 | 5/2001 | Jamiolkowski et al. |

(56) References Cited

U.S. PATENT DOCUMENTS

| | | |
|---|---|---|
| 6,235,712 B1 | 5/2001 | Stevenson et al. |
| 6,245,349 B1 | 6/2001 | Yiv et al. |
| 6,245,357 B1 | 6/2001 | Edgren et al. |
| 6,248,112 B1 | 6/2001 | Gambale et al. |
| 6,251,435 B1 | 6/2001 | Jamiolkowski et al. |
| D445,975 S | 7/2001 | Stratford |
| 6,258,377 B1 | 7/2001 | New et al. |
| 6,261,584 B1 | 7/2001 | Peery et al. |
| 6,268,343 B1 | 7/2001 | Knudsen et al. |
| 6,270,700 B1 | 8/2001 | Ignatious |
| 6,270,787 B1 | 8/2001 | Ayer |
| 6,277,413 B1 | 8/2001 | Sankaram |
| 6,283,949 B1 | 9/2001 | Roorda |
| 6,284,264 B1 | 9/2001 | Zerbe et al. |
| 6,284,727 B1 | 9/2001 | Kim et al. |
| 6,287,295 B1 | 9/2001 | Chen et al. |
| 6,284,725 B1 | 12/2001 | Coolidge et al. |
| 6,329,336 B1 | 12/2001 | Bridon et al. |
| 6,331,311 B1 | 12/2001 | Brodbeck et al. |
| 6,372,218 B1 | 4/2002 | Cummins, Jr. |
| 6,372,256 B2 | 4/2002 | Jamiolkowski et al. |
| 6,375,978 B1 | 4/2002 | Kleiner et al. |
| 6,395,292 B2 | 5/2002 | Peery et al. |
| 6,403,655 B1 | 6/2002 | Bezwada et al. |
| 6,419,952 B2 | 7/2002 | Wong et al. |
| 6,433,144 B1 | 8/2002 | Morris et al. |
| 6,436,091 B1 | 8/2002 | Harper et al. |
| 6,447,522 B2 | 9/2002 | Gambale et al. |
| 6,451,974 B1 | 9/2002 | Hansen |
| 6,458,385 B2 | 10/2002 | Jamiolkowski et al. |
| 6,458,387 B1 | 10/2002 | Scott et al. |
| 6,458,924 B2 | 10/2002 | Knudsen et al. |
| 6,461,605 B1 | 10/2002 | Cutler et al. |
| 6,464,688 B1 | 10/2002 | Harper et al. |
| 6,468,961 B1 | 10/2002 | Brodbeck et al. |
| 6,471,688 B1 | 10/2002 | Harper et al. |
| 6,472,512 B1 | 10/2002 | LaFleur et al. |
| 6,485,706 B1 | 11/2002 | McCoy et al. |
| 6,495,164 B1 | 12/2002 | Ramstack et al. |
| 6,506,724 B1 | 1/2003 | Hiles et al. |
| 6,508,808 B1 | 1/2003 | Carr et al. |
| 6,514,500 B1 | 2/2003 | Bridon et al. |
| 6,514,517 B2 | 2/2003 | Jamilolkowski et al. |
| 6,524,305 B1 | 2/2003 | Peterson et al. |
| 6,528,093 B1 | 3/2003 | Kamei et al. |
| 6,528,486 B1 | 3/2003 | Larsen et al. |
| D472,896 S | 4/2003 | Peiker |
| 6,541,021 B1 | 4/2003 | Johnson et al. |
| 6,544,252 B1 | 4/2003 | Theeuwes et al. |
| 6,547,250 B1 | 4/2003 | Noble |
| 6,551,613 B1 | 4/2003 | Dong et al. |
| 6,569,420 B2 | 5/2003 | Chen et al. |
| 6,572,890 B2 | 6/2003 | Faour et al. |
| 6,579,851 B2 | 6/2003 | Goeke et al. |
| 6,592,887 B2 | 7/2003 | Zerbe et al. |
| 6,593,295 B2 | 7/2003 | Bridon et al. |
| 6,635,268 B2 | 10/2003 | Peery et al. |
| 6,667,061 B2 | 12/2003 | Ramstack et al. |
| 6,670,368 B1 | 12/2003 | Breault et al. |
| 6,673,767 B1 | 1/2004 | Brodbeck et al. |
| 6,682,522 B2 | 1/2004 | Carr et al. |
| 6,703,225 B1 | 3/2004 | Kojima et al. |
| 6,703,359 B1 | 3/2004 | Young et al. |
| 6,706,689 B2 | 3/2004 | Coolidge et al. |
| 6,709,671 B2 | 3/2004 | Zerbe et al. |
| 6,720,407 B1 | 4/2004 | Hughes et al. |
| 6,730,328 B2 | 5/2004 | Maskiwicz et al. |
| 6,767,887 B2 | 7/2004 | Hoffmann et al. |
| 6,821,949 B2 | 11/2004 | Bridon et al. |
| 6,833,256 B1 | 12/2004 | Pontzer et al. |
| 6,835,194 B2 | 12/2004 | Johnson et al. |
| 6,840,931 B2 | 1/2005 | Peterson et al. |
| 6,849,708 B1 | 2/2005 | Habener |
| 6,849,714 B1 | 2/2005 | Bridon et al. |
| 6,858,576 B1 | 2/2005 | Young et al. |
| 6,872,700 B1 | 3/2005 | Young et al. |
| 6,875,748 B2 | 4/2005 | Manthorpe et al. |
| 6,887,470 B1 | 5/2005 | Bridon et al. |
| 6,887,849 B2 | 5/2005 | Bridon et al. |
| 6,899,887 B2 | 5/2005 | Ayer |
| 6,899,898 B2 | 5/2005 | Albayrak |
| 6,902,744 B1 | 6/2005 | Kolterman et al. |
| 6,903,186 B1 | 6/2005 | Dong |
| 6,913,767 B1 | 7/2005 | Cleland et al. |
| 6,923,800 B2 | 8/2005 | Chen et al. |
| 6,924,264 B1 | 8/2005 | Prickett et al. |
| 6,939,556 B2 | 9/2005 | Lautenbach |
| 6,956,026 B2 | 10/2005 | Beeley et al. |
| 6,969,702 B2 | 11/2005 | Bertilsson et al. |
| 6,976,981 B2 | 12/2005 | Ayer |
| 6,989,366 B2 | 1/2006 | Beeley et al. |
| 6,992,065 B2 | 1/2006 | Okumu |
| 6,997,922 B2 | 2/2006 | Theeuwes et al. |
| 7,014,636 B2 | 3/2006 | Gilbert |
| 7,022,674 B2 | 4/2006 | DeFelippis et al. |
| 7,041,646 B2 | 5/2006 | Pan et al. |
| 7,074,423 B2 | 7/2006 | Fereira et al. |
| 7,084,243 B2 | 8/2006 | Glaesner et al. |
| 7,101,567 B1 | 9/2006 | Sano et al. |
| 7,101,843 B2 | 9/2006 | Glaesner et al. |
| 7,112,335 B2 | 9/2006 | Lautenbach |
| 7,115,569 B2 | 10/2006 | Beeley et al. |
| 7,138,375 B2 | 11/2006 | Beeley et al. |
| 7,138,486 B2 | 11/2006 | Habener et al. |
| 7,141,547 B2 | 11/2006 | Rosen et al. |
| 7,144,863 B2 | 12/2006 | DeFelippis et al. |
| 7,153,825 B2 | 12/2006 | Young et al. |
| 7,157,555 B1 | 1/2007 | Beeley et al. |
| 7,163,688 B2 | 1/2007 | Peery et al. |
| 7,163,697 B2 | 1/2007 | Hanes et al. |
| 7,199,217 B2 | 4/2007 | DiMarchi et al. |
| 7,205,409 B2 | 4/2007 | Pei et al. |
| 7,207,982 B2 | 4/2007 | Dionne et al. |
| 7,241,457 B2 | 7/2007 | Chen et al. |
| 7,258,869 B1 | 8/2007 | Berry et al. |
| D555,589 S | 11/2007 | Hussaini et al. |
| 7,297,761 B2 | 11/2007 | Beeley et al. |
| 7,316,680 B2 | 1/2008 | Gilbert |
| 7,393,827 B2 | 7/2008 | Nadler |
| 7,407,499 B2 | 8/2008 | Trautman |
| 7,442,682 B2 | 10/2008 | Kitaura et al. |
| 7,456,254 B2 | 11/2008 | Wright et al. |
| 7,459,432 B2 | 12/2008 | Cowley et al. |
| 7,521,423 B2 | 4/2009 | Young et al. |
| 7,563,871 B2 | 7/2009 | Wright et al. |
| 7,589,169 B2 | 9/2009 | Bolotin |
| 7,612,176 B2 | 11/2009 | Wright et al. |
| 7,635,463 B2 | 12/2009 | Bolotin et al. |
| D608,447 S | 1/2010 | Meyer et al. |
| 7,655,254 B2 | 2/2010 | Dennis et al. |
| 7,655,257 B2 | 2/2010 | Peery et al. |
| 7,666,835 B2 | 2/2010 | Bloom et al. |
| 7,682,356 B2 | 3/2010 | Alessi et al. |
| 7,727,519 B2 | 6/2010 | Moran |
| 7,731,947 B2 | 6/2010 | Eliaz et al. |
| 7,736,665 B2 | 6/2010 | Patel et al. |
| 7,741,269 B2 | 6/2010 | Young et al. |
| 7,790,140 B2 | 9/2010 | Bolotin |
| 7,825,091 B2 | 11/2010 | Bloom et al. |
| 7,829,109 B2 | 11/2010 | Chen et al. |
| 7,833,543 B2 | 11/2010 | Gibson et al. |
| 7,879,028 B2 | 2/2011 | Alessi et al. |
| 7,879,794 B2 | 4/2011 | Berry et al. |
| 7,919,109 B2 | 4/2011 | Berry et al. |
| D638,478 S | 5/2011 | Block |
| 7,928,065 B2 | 6/2011 | Rohloff et al. |
| 7,964,183 B2 | 6/2011 | Eliaz et al. |
| 8,039,432 B2 | 10/2011 | Bridon et al. |
| 7,959,938 B2 | 11/2011 | Lautenbach et al. |
| 8,048,438 B2 | 11/2011 | Berry et al. |
| 8,052,996 B2 | 11/2011 | Lautenbach et al. |
| 8,058,233 B2 | 11/2011 | Cowley et al. |
| 8,101,576 B2 | 1/2012 | Bloom |
| 8,114,430 B2 | 2/2012 | Rohloff et al. |

(56) References Cited

U.S. PATENT DOCUMENTS

| | | |
|---|---|---|
| 8,114,437 B2 | 2/2012 | Rohloff et al. |
| 8,158,150 B2 | 4/2012 | Lautenbach et al. |
| 8,173,150 B2 | 5/2012 | Berry et al. |
| 8,202,836 B2 | 6/2012 | Moore et al. |
| 8,206,745 B2 | 6/2012 | Rohloff et al. |
| 8,211,467 B2 | 7/2012 | Rohloff et al. |
| 8,217,001 B2 | 7/2012 | Cowley et al. |
| 8,231,859 B2 | 7/2012 | Bolotin et al. |
| 8,257,682 B2 | 9/2012 | Bolotin et al. |
| 8,257,691 B2 | 9/2012 | Eliaz et al. |
| 8,262,667 B1 | 9/2012 | Silver et al. |
| 8,263,545 B2 | 9/2012 | Bloom |
| 8,263,736 B2 | 9/2012 | Berry |
| 8,268,341 B2 | 9/2012 | Berry |
| 8,273,365 B2 | 9/2012 | Lautenbach et al. |
| 8,273,713 B2 | 9/2012 | Pittner et al. |
| D669,589 S | 10/2012 | Delaey |
| 8,277,776 B2 | 10/2012 | Bolotin et al. |
| 8,278,267 B2 | 10/2012 | Weyer et al. |
| 8,288,338 B2 | 10/2012 | Alessi et al. |
| 8,298,561 B2 | 10/2012 | Alessi et al. |
| 8,299,025 B2 | 10/2012 | Alessi et al. |
| 8,343,140 B2 | 1/2013 | Alessi et al. |
| 8,367,095 B2 | 2/2013 | Lautenbach et al. |
| 8,372,424 B2 | 2/2013 | Berry et al. |
| D678,889 S | 3/2013 | Chiu |
| 8,398,967 B2 | 3/2013 | Eliaz et al. |
| 8,440,226 B2 | 5/2013 | Rohloff et al. |
| 8,460,694 B2 | 6/2013 | Rohloff et al. |
| 8,470,353 B2 | 6/2013 | Lautenbach et al. |
| 8,801,700 B2 | 8/2014 | Alessi et al. |
| 8,815,802 B2 * | 8/2014 | Kalthoff ............... A61K 38/00 514/11.7 |
| 8,858,621 B2 | 10/2014 | Oba et al. |
| 8,865,202 B2 | 10/2014 | Zerbe et al. |
| 8,888,745 B2 | 11/2014 | Van Der Graaf et al. |
| 8,926,595 B2 * | 1/2015 | Alessi ............... A61K 9/0004 604/892.1 |
| 8,940,316 B2 * | 1/2015 | Alessi ............... A61K 9/0004 424/423 |
| 8,992,961 B2 | 3/2015 | Berry et al. |
| 8,992,962 B2 | 3/2015 | Lautenbach et al. |
| 9,044,209 B2 | 6/2015 | Dayton et al. |
| 9,078,900 B2 | 7/2015 | Kuzma et al. |
| 9,095,553 B2 | 8/2015 | Rohloff et al. |
| 9,241,722 B2 | 1/2016 | Yu |
| D750,764 S | 3/2016 | DeSocio |
| 9,332,995 B2 | 5/2016 | Russo |
| 9,526,763 B2 | 12/2016 | Rohloff et al. |
| 9,539,200 B2 | 1/2017 | Lautenbach |
| 9,572,889 B2 | 2/2017 | Alessi et al. |
| D789,539 S | 6/2017 | Kleiner et al. |
| D789,540 S | 6/2017 | Gyorgy |
| 9,682,127 B2 | 6/2017 | Alessi et al. |
| RE46,577 E | 10/2017 | Collins et al. |
| 9,889,085 B1 | 2/2018 | Alessi et al. |
| 2001/0012511 A1 | 8/2001 | Bezwada et al. |
| 2001/0021377 A1 | 9/2001 | Jamiolkowski et al. |
| 2001/0021822 A1 | 9/2001 | Ayer |
| 2001/0022974 A1 | 9/2001 | Ayer |
| 2001/0026793 A1 | 10/2001 | Jamiolkowski et al. |
| 2001/0027311 A1 | 10/2001 | Chen et al. |
| 2001/0031790 A1 | 11/2001 | Beisswenger |
| 2001/0036472 A1 | 11/2001 | Wong et al. |
| 2001/0040326 A1 | 11/2001 | Balczun |
| 2002/0001631 A1 | 1/2002 | Okumu |
| 2002/0004481 A1 | 1/2002 | Cleland et al. |
| 2002/0012818 A1 | 1/2002 | Ruppi et al. |
| 2002/0034532 A1 | 3/2002 | Brodbeck et al. |
| 2002/0037309 A1 | 3/2002 | Jaworowicz et al. |
| 2002/0048600 A1 | 4/2002 | Bhatt et al. |
| 2002/0098180 A1 | 7/2002 | Lei |
| 2002/0136848 A1 | 9/2002 | Yoshii et al. |
| 2002/0137666 A1 | 9/2002 | Beeley et al. |
| 2002/0141985 A1 | 10/2002 | Pittner et al. |
| 2002/0197185 A1 | 12/2002 | Jamiolkowski et al. |
| 2002/0197235 A1 | 12/2002 | Moran |
| 2003/0032947 A1 | 2/2003 | Harper et al. |
| 2003/0044467 A1 | 3/2003 | Brodbeck et al. |
| 2003/0045454 A1 | 3/2003 | Okumu et al. |
| 2003/0059376 A1 | 3/2003 | Libbey et al. |
| 2003/0060425 A1 | 3/2003 | Ahlem et al. |
| 2003/0097121 A1 | 6/2003 | Babcock et al. |
| 2003/0104063 A1 | 6/2003 | Babcock et al. |
| 2003/0108608 A1 | 6/2003 | Berry et al. |
| 2003/0108609 A1 | 6/2003 | Berry et al. |
| 2003/0113380 A1 | 6/2003 | Ramstack et al. |
| 2003/0114837 A1 | 6/2003 | Peterson et al. |
| 2003/0118660 A1 | 6/2003 | Rickey et al. |
| 2003/0138403 A1 | 7/2003 | Drustrup |
| 2003/0138491 A1 | 7/2003 | Tracy et al. |
| 2003/0157178 A1 | 8/2003 | Chen et al. |
| 2003/0170289 A1 | 9/2003 | Chen et al. |
| 2003/0180364 A1 | 9/2003 | Chen et al. |
| 2003/0186858 A1 | 10/2003 | Arentsen |
| 2003/0191099 A1 | 10/2003 | Bohlmann et al. |
| 2003/0211974 A1 | 11/2003 | Brodbeck et al. |
| 2003/0215515 A1 | 11/2003 | Truong-Le et al. |
| 2004/0001689 A1 | 1/2004 | Goldsmith et al. |
| 2004/0001889 A1 | 1/2004 | Chen et al. |
| 2004/0002442 A1 | 1/2004 | Pan et al. |
| 2004/0022859 A1 | 2/2004 | Chen et al. |
| 2004/0024068 A1 | 2/2004 | Chen et al. |
| 2004/0024069 A1 | 2/2004 | Chen et al. |
| 2004/0029784 A1 | 2/2004 | Hathaway |
| 2004/0039376 A1 | 2/2004 | Peery et al. |
| 2004/0097906 A1 | 5/2004 | Fereira et al. |
| 2004/0101557 A1 | 5/2004 | Gibson et al. |
| 2004/0102762 A1 | 5/2004 | Gilbert |
| 2004/0115236 A1 | 6/2004 | Chan et al. |
| 2004/0142867 A1 | 7/2004 | Oi et al. |
| 2004/0142902 A1 | 7/2004 | Struijker-Boudier |
| 2004/0151753 A1 | 8/2004 | Chen et al. |
| 2004/0157951 A1 | 8/2004 | Wolf |
| 2004/0198654 A1 | 10/2004 | Glaesner et al. |
| 2004/0209801 A1 | 10/2004 | Brand et al. |
| 2004/0224903 A1 | 11/2004 | Berry et al. |
| 2004/0225113 A1 | 11/2004 | LaFleur et al. |
| 2004/0243106 A1 | 12/2004 | Ayer |
| 2004/0265273 A1 | 12/2004 | Li et al. |
| 2004/0266683 A1 | 12/2004 | Hathaway et al. |
| 2004/0266692 A1 | 12/2004 | Young et al. |
| 2005/0004557 A1 | 1/2005 | Russell |
| 2005/0008661 A1 | 1/2005 | Fereira et al. |
| 2005/0009742 A1 | 1/2005 | Bertilsson et al. |
| 2005/0010196 A1 | 1/2005 | Fereira et al. |
| 2005/0070883 A1 | 3/2005 | Brown et al. |
| 2005/0070927 A1 | 3/2005 | Feinberg |
| 2005/0079200 A1 | 4/2005 | Rathenow et al. |
| 2005/0079202 A1 | 4/2005 | Chen et al. |
| 2005/0010942 A1 | 5/2005 | Eliaz et al. |
| 2005/0095284 A1 | 5/2005 | Trautman |
| 2005/0101943 A1 | 5/2005 | Ayer et al. |
| 2005/0106214 A1 | 5/2005 | Chen |
| 2005/0112188 A1 | 5/2005 | Eliaz et al. |
| 2005/0118206 A1 | 6/2005 | Luk et al. |
| 2005/0118221 A1 | 6/2005 | Blakely et al. |
| 2005/0131386 A1 | 6/2005 | Freeman et al. |
| 2005/0131389 A1 | 6/2005 | Peterson et al. |
| 2005/0175701 A1 | 8/2005 | Pan et al. |
| 2005/0201980 A1 | 9/2005 | Moran |
| 2005/0215475 A1 | 9/2005 | Ong et al. |
| 2005/0216087 A1 | 9/2005 | Zucherman, Jr. et al. |
| 2005/0266087 A1 | 12/2005 | Junnarkar et al. |
| 2005/0271702 A1 | 12/2005 | Wright et al. |
| 2005/0276856 A1 | 12/2005 | Fereira et al. |
| 2005/0281879 A1 | 12/2005 | Chen et al. |
| 2006/0013879 A9 | 1/2006 | Brodbeck et al. |
| 2006/0014678 A1 | 1/2006 | Cowley et al. |
| 2006/0030526 A1 | 2/2006 | Liu et al. |
| 2006/0069029 A1 | 3/2006 | Kolterman et al. |
| 2006/0073182 A1 | 4/2006 | Wong et al. |
| 2006/0084604 A1 | 4/2006 | Kitaura et al. |
| 2006/0084922 A1 | 4/2006 | Botha |

(56) References Cited

U.S. PATENT DOCUMENTS

| | | |
|---|---|---|
| 2006/0094652 A1 | 5/2006 | Levy et al. |
| 2006/0094693 A1 | 5/2006 | Aziz et al. |
| 2006/0106399 A1 | 5/2006 | Taras et al. |
| 2006/0141040 A1 | 6/2006 | Chen et al. |
| 2006/0142234 A1 | 6/2006 | Chen et al. |
| 2006/0160736 A1 | 7/2006 | Nadler |
| 2006/0178304 A1 | 8/2006 | Juul-Mortensen et al. |
| 2006/0193918 A1 | 8/2006 | Rohloff et al. |
| 2006/0216242 A1 | 9/2006 | Rohloff et al. |
| 2006/0224145 A1 | 10/2006 | Gills |
| 2006/0233841 A1 | 10/2006 | Brodbeck et al. |
| 2006/0246138 A1 | 11/2006 | Rohloff et al. |
| 2006/0251618 A1 | 11/2006 | Dennis et al. |
| 2006/0263433 A1 | 11/2006 | Ayer et al. |
| 2006/0264890 A1 | 11/2006 | Moberg et al. |
| 2006/0280795 A1 | 12/2006 | Penhasi et al. |
| 2006/0293232 A1 | 12/2006 | Levy et al. |
| 2007/0027105 A1 | 2/2007 | Junnarkar et al. |
| 2007/0149011 A1 | 6/2007 | Kent et al. |
| 2007/0166352 A1 | 7/2007 | Wright et al. |
| 2007/0207958 A1 | 9/2007 | Bridon et al. |
| 2007/0248572 A1 | 10/2007 | Moran et al. |
| 2007/0281024 A1 | 12/2007 | Lautenbach et al. |
| 2008/0020016 A1 | 1/2008 | Li et al. |
| 2008/0038316 A1 | 2/2008 | Wong et al. |
| 2008/0064636 A1 | 3/2008 | Bloom et al. |
| 2008/0065090 A1 | 3/2008 | Scribner et al. |
| 2008/0091176 A1 | 4/2008 | Alessi et al. |
| 2008/0110515 A1 | 5/2008 | Angelosanto et al. |
| 2008/0112994 A1 | 5/2008 | Junnarkar et al. |
| 2008/0200383 A1 | 8/2008 | Jennings et al. |
| 2008/0207512 A1 | 8/2008 | Roth et al. |
| 2008/0208194 A1 | 8/2008 | Bickenbach |
| 2008/0226625 A1 | 9/2008 | Berry et al. |
| 2008/0226689 A1 | 9/2008 | Berry et al. |
| 2008/0260838 A1 | 10/2008 | Hokenson et al. |
| 2008/0260840 A1 | 10/2008 | Alessi et al. |
| 2008/0269725 A1 | 10/2008 | Deem et al. |
| 2008/0312157 A1 | 12/2008 | Levy et al. |
| 2009/0022727 A1 | 1/2009 | Houston et al. |
| 2009/0036364 A1 | 2/2009 | Levy et al. |
| 2009/0042781 A1 | 2/2009 | Petersen et al. |
| 2009/0074734 A1 | 3/2009 | Rottiers |
| 2009/0087408 A1 | 4/2009 | Berry et al. |
| 2009/0156474 A1 | 6/2009 | Roth et al. |
| 2009/0163447 A1 | 6/2009 | Maggio |
| 2009/0186817 A1 | 7/2009 | Ghosh et al. |
| 2009/0202481 A1 | 8/2009 | Li et al. |
| 2009/0202608 A1 | 8/2009 | Alessi et al. |
| 2009/0209460 A1 | 8/2009 | Young et al. |
| 2009/0210019 A1 | 8/2009 | Kim et al. |
| 2009/0215694 A1 | 8/2009 | Kolterman et al. |
| 2009/0234392 A1 | 9/2009 | Dziedzic |
| 2009/0247463 A1 | 10/2009 | Wright et al. |
| 2009/0254143 A1 | 10/2009 | Tweden et al. |
| 2009/0286723 A1 | 11/2009 | Levy et al. |
| 2009/0312246 A1 | 12/2009 | Baron et al. |
| 2010/0092566 A1 | 4/2010 | Alessi et al. |
| 2010/0105627 A1 | 4/2010 | Salama et al. |
| 2010/0144621 A1 | 6/2010 | Kim et al. |
| 2010/0185184 A1 | 7/2010 | Alessi et al. |
| 2010/0297209 A1 | 11/2010 | Rohloff et al. |
| 2010/0298840 A1 | 11/2010 | Schwartz |
| 2011/0076317 A1 | 3/2011 | Alessi et al. |
| 2011/0091527 A1 | 4/2011 | Moonen et al. |
| 2011/0104111 A1 | 5/2011 | Rohloff et al. |
| 2011/0152181 A1 | 6/2011 | Alsina-Fernandez et al. |
| 2011/0152182 A1 | 6/2011 | Alsina-Fernandez et al. |
| 2011/0160708 A1 | 6/2011 | Berry et al. |
| 2011/0166554 A1 | 7/2011 | Alessi et al. |
| 2011/0264077 A1 | 10/2011 | Rohloff et al. |
| 2011/0306549 A1 | 12/2011 | Tatarkiewicz et al. |
| 2012/0208755 A1 | 8/2012 | Leung |
| 2013/0030417 A1 | 1/2013 | Alessi |
| 2013/0034210 A1 | 2/2013 | Rohloff et al. |
| 2013/0052237 A1 | 2/2013 | Eliaz et al. |
| 2014/0058425 A1 | 2/2014 | Porat |
| 2014/0121741 A1 | 5/2014 | Bennett et al. |
| 2014/0257272 A1 | 9/2014 | Clark, III et al. |
| 2014/0378900 A1 | 12/2014 | Alessi et al. |
| 2015/0057227 A1 | 2/2015 | Leung |
| 2015/0111818 A1 | 4/2015 | Alessi et al. |
| 2015/0133791 A1 | 5/2015 | Sato et al. |
| 2015/0231062 A1 | 8/2015 | Lautenbach et al. |
| 2015/0231256 A1 | 8/2015 | Berry et al. |
| 2015/0297509 A1 | 10/2015 | Schwarz |
| 2016/0022582 A1 | 1/2016 | Alessi et al. |
| 2016/0030337 A1 | 2/2016 | Kuzma et al. |
| 2016/0354115 A1 | 12/2016 | Smith et al. |
| 2016/0354305 A1 | 12/2016 | Alessi et al. |
| 2017/0056476 A1 | 3/2017 | Rohloff et al. |
| 2017/0079906 A1 | 3/2017 | Alessi et al. |
| 2017/0119854 A1 | 5/2017 | Alessi et al. |
| 2017/0119855 A1 | 5/2017 | Berry et al. |
| 2017/0181964 A1 | 6/2017 | Lautenbach et al. |
| 2017/0273706 A1 | 9/2017 | Mirza et al. |
| 2017/0319470 A1 | 11/2017 | Eliaz et al. |
| 2017/0319662 A1 | 11/2017 | Berry et al. |
| 2017/0348392 A1 | 12/2017 | Rohloff et al. |
| 2017/0368145 A1 | 12/2017 | Alessi et al. |
| 2018/0009871 A1 | 1/2018 | Blackwell et al. |
| 2018/0185451 A1 | 7/2018 | Young et al. |

FOREIGN PATENT DOCUMENTS

| | | |
|---|---|---|
| EP | 0254394 | 1/1988 |
| EP | 0295411 | 12/1988 |
| EP | 0302582 A1 | 2/1989 |
| EP | 0368339 | 5/1990 |
| EP | 0373867 | 6/1990 |
| EP | 0431942 | 6/1991 |
| EP | 0486959 A1 | 5/1992 |
| EP | 0521586 A1 | 1/1993 |
| EP | 0596161 | 5/1994 |
| EP | 0379147 | 9/1994 |
| EP | 0627231 | 12/1994 |
| EP | 0729747 | 5/1997 |
| EP | 0771817 | 5/1997 |
| EP | 0841359 | 5/1998 |
| EP | 0767689 | 6/1999 |
| EP | 1046399 | 10/2000 |
| EP | 1084703 | 3/2001 |
| EP | 1300129 A2 | 4/2003 |
| EP | 1300173 A2 | 4/2003 |
| EP | 1600187 | 1/2009 |
| EP | 2133073 A1 | 12/2009 |
| EP | 2020990 | 9/2010 |
| FR | 640907 | 7/1928 |
| GB | 1049104 | 11/1966 |
| GB | 1518683 | 7/1978 |
| GB | 2501400 | 10/2013 |
| JP | H02124814 A | 5/1990 |
| JP | H07196479 A | 8/1995 |
| JP | 9241153 | 9/1997 |
| JP | 11-100353 | 4/1999 |
| JP | 2006/213727 A | 8/2006 |
| NL | 9100160 | 8/1992 |
| NZ | 592113 | 8/2012 |
| TW | 200634060 | 10/2006 |
| WO | WO-1989003678 A1 | 5/1989 |
| WO | WO-1990013285 A1 | 11/1990 |
| WO | WO-1990013361 A1 | 11/1990 |
| WO | WO-1990013780 A1 | 11/1990 |
| WO | WO 91/07160 | 5/1991 |
| WO | WO-1992019241 A1 | 11/1992 |
| WO | WO 93/06819 | 4/1993 |
| WO | WO 93/06821 | 4/1993 |
| WO | WO 93/008832 | 5/1993 |
| WO | WO 93/09763 | 5/1993 |
| WO | WO 93/23083 | 11/1993 |
| WO | WO 94/09743 | 5/1994 |
| WO | WO 1994010982 A1 | 5/1994 |
| WO | WO 94/21262 | 9/1994 |
| WO | WO 95/01167 | 1/1995 |

(56) References Cited

FOREIGN PATENT DOCUMENTS

| | | |
|---|---|---|
| WO | WO 95/09006 | 4/1995 |
| WO | WO 95/09007 | 4/1995 |
| WO | WO-1995013799 A1 | 5/1995 |
| WO | WO 95/34285 | 12/1995 |
| WO | WO 96/001134 | 1/1996 |
| WO | WO 96/003116 | 2/1996 |
| WO | WO-1996036317 A1 | 11/1996 |
| WO | WO 96/39142 | 12/1996 |
| WO | WO 96/40049 | 12/1996 |
| WO | WO 96/40139 | 12/1996 |
| WO | WO 96/40355 | 12/1996 |
| WO | WO-1996040049 A1 | 12/1996 |
| WO | WO 97/15289 | 5/1997 |
| WO | WO 97/15296 | 5/1997 |
| WO | WO 97/28181 | 8/1997 |
| WO | WO-1997031943 A1 | 9/1997 |
| WO | WO-1997044039 A1 | 11/1997 |
| WO | WO 97/46204 | 12/1997 |
| WO | WO 97/47339 | 12/1997 |
| WO | WO 98/00152 | 1/1998 |
| WO | WO 98/00157 | 1/1998 |
| WO | WO 98/00158 | 1/1998 |
| WO | WO 98/02169 | 1/1998 |
| WO | WO-1997041837 A3 | 2/1998 |
| WO | WO-1998007412 A1 | 2/1998 |
| WO | WO 98/16250 | 4/1998 |
| WO | WO 98/17315 | 4/1998 |
| WO | WO 98/20930 | 5/1998 |
| WO | WO 98/27960 | 7/1998 |
| WO | WO 98/027962 | 7/1998 |
| WO | WO 98/27963 | 7/1998 |
| WO | WO 98/030231 | 7/1998 |
| WO | WO 98/32463 | 7/1998 |
| WO | WO-1998030231 A1 | 7/1998 |
| WO | WO 98/42317 | 10/1998 |
| WO | WO 98/47487 | 10/1998 |
| WO | WO 98/51282 | 11/1998 |
| WO | WO 99/03453 | 1/1999 |
| WO | WO 99/04767 | 2/1999 |
| WO | WO 99/004768 | 2/1999 |
| WO | WO-1999012549 A2 | 3/1999 |
| WO | WO 99/16419 | 4/1999 |
| WO | WO 99/025728 | 5/1999 |
| WO | WO 99/29306 | 6/1999 |
| WO | WO 99/033446 | 7/1999 |
| WO | WO 99/33449 | 7/1999 |
| WO | WO 99/39700 | 8/1999 |
| WO | WO 99/040788 | 8/1999 |
| WO | WO 99/044659 | 9/1999 |
| WO | WO 99/062501 | 12/1999 |
| WO | WO 99/064061 | 12/1999 |
| WO | WO 00/013663 | 3/2000 |
| WO | WO 00/029206 | 5/2000 |
| WO | WO 00/038652 | 7/2000 |
| WO | WO 00/039280 | 7/2000 |
| WO | WO 00/040273 | 7/2000 |
| WO | WO 00/041548 | 7/2000 |
| WO | WO 00/045790 | 8/2000 |
| WO | WO 00/054745 | 9/2000 |
| WO | WO-2000059476 A1 | 10/2000 |
| WO | WO 00/066138 | 11/2000 |
| WO | WO 00/067728 | 11/2000 |
| WO | WO-2000066087 A2 | 11/2000 |
| WO | WO-2001019345 A1 | 3/2001 |
| WO | WO 2001028525 A2 | 4/2001 |
| WO | WO 01/043528 | 6/2001 |
| WO | WO 01/051041 | 7/2001 |
| WO | WO 01/78683 | 10/2001 |
| WO | WO 02/028366 | 4/2002 |
| WO | WO 02/036072 | 5/2002 |
| WO | WO 02/043800 | 6/2002 |
| WO | WO 02/045752 | 6/2002 |
| WO | WO 02/47716 | 6/2002 |
| WO | WO 02/067895 | 9/2002 |
| WO | WO 02/069983 | 9/2002 |
| WO | WO 02/76344 | 10/2002 |
| WO | WO 02/085428 | 10/2002 |
| WO | WO 03/000230 | 1/2003 |
| WO | WO 03/007981 | 1/2003 |
| WO | WO 03/011892 | 2/2003 |
| WO | WO 03/024357 | 3/2003 |
| WO | WO 03/024503 | 3/2003 |
| WO | WO-2003020245 A1 | 3/2003 |
| WO | WO 03/030923 | 4/2003 |
| WO | WO 03/041684 | 5/2003 |
| WO | WO 03/041757 | 5/2003 |
| WO | WO 03/053400 | 7/2003 |
| WO | WO-2003066585 A2 | 8/2003 |
| WO | WO 03/072113 | 9/2003 |
| WO | WO 03/072133 | 9/2003 |
| WO | WO 04/002565 | 1/2004 |
| WO | WO-2004034975 A2 | 4/2004 |
| WO | WO-2004035754 A2 | 4/2004 |
| WO | WO-2004035762 A2 | 4/2004 |
| WO | WO 2004036186 A2 | 4/2004 |
| WO | WO 04/052336 | 6/2004 |
| WO | WO 04/056338 | 7/2004 |
| WO | WO 04/089335 | 10/2004 |
| WO | WO 2004103342 A2 | 12/2004 |
| WO | WO 05/048930 | 6/2005 |
| WO | WO 05/048952 | 6/2005 |
| WO | WO 05/102293 | 11/2005 |
| WO | WO-2005102293 A1 | 11/2005 |
| WO | WO 2005110425 | 11/2005 |
| WO | WO 06/017772 | 2/2006 |
| WO | WO 06/023526 | 3/2006 |
| WO | WO 06/081279 | 8/2006 |
| WO | WO 06/083761 | 8/2006 |
| WO | WO 06/084139 | 8/2006 |
| WO | WO 06/086727 | 8/2006 |
| WO | WO 06/101815 | 9/2006 |
| WO | WO 06/111169 | 10/2006 |
| WO | WO-2006/131730 | 12/2006 |
| WO | WO 07/024700 | 3/2007 |
| WO | WO 07/056681 | 5/2007 |
| WO | WO 07/075534 | 7/2007 |
| WO | WO 07/084460 | 7/2007 |
| WO | WO 07/133778 | 11/2007 |
| WO | WO 07/140416 | 12/2007 |
| WO | WO 08/021133 | 2/2008 |
| WO | WO-2008041245 A2 | 4/2008 |
| WO | WO 08/061355 | 5/2008 |
| WO | WO-2008/086086 A2 | 7/2008 |
| WO | WO 08/133908 | 11/2008 |
| WO | WO 08/134425 | 11/2008 |
| WO | WO 09/109927 | 9/2009 |
| WO | WO-2009143285 A2 | 11/2009 |
| WO | WO 2013/004983 | 1/2013 |

OTHER PUBLICATIONS

Costantino et al., "Protein Spray Freeze Drying. 2. Effect of Formulation Variables on particle Size and Stability," J. Pharm. Sci. 91:388-395 (2002).

Henry et al., "Comparing ITCA 650, continuous subcutaneous delivery of exenatide via DUROS® device vs. twice daily exenatide injections in metformin-treated type 2 diabetes," oral presentation at the 46th Annual Meeting of the European Association for the Study of Diabetes in Stockholm, Sweden , 21 pages (Sep. 20-24, 2010).

Huggins et al., "Synergistic antiviral effects of ribavirin and the C-nucleoside analogs tiazofurin and selenazofurin against togaviruses, bunyaviruses, and arenaviruses," Antimicrobial Agents & Chemotherapy, 26(4):476-480 (1984).

Ishiwata et al., "Clinical effects of the recombinant feline interferon-omega on experimental parvovirus infection in beagle dogs," J. Vet. Med. Sci. 60(8):911-917 (1998).

Johnson et al., "How interferons fight disease," Sci. Am. 270(5):68-75 (May 1994).

Lublin et al., "Defining the clinical course of multiple sclerosis: results of an international survey," Neurology. 46:907-911 (1996).

(56) References Cited

OTHER PUBLICATIONS

Madsbad, "Exenatide and liraglutide: different approaches to develop GLP-1 receptor agonists (incretin mimetics)—preclinical and clinical results," Best Practice & Research Clinical Endocrinology & Metabolism 23:463-77 (2009).
Nielsen, "Incretin mimetics and DPP-IV inhibitors for the treatment of type 2 diabetes," Drug Discovery Today 10(10):703-710 (May 15, 2005).
Palmeri et al., "5-Fluorouracil and recombinant α-interferon-2a in the treatment of advanced colorectal carcinoma: a dose optimization study," J. Chemotherapy 2(5):327-330 (Oct. 1990).
Patti et al., "Natural interferon-b treatment of relapsing-remitting and secondary-progressive multiple sclerosis patients: two-year study," Acta. Neurol. Scand. 100:283-289 (1999).
Paty et al., "Interferon beta-1 b is effective in relapsing-remitting multiple sclerosis," Neurology 43:662-667 (1993).
PCT International Search Report for PCT/US2009/000916, 4 pages (dated Aug. 12, 2009).
"Intarcia Therapeutics Announces Final Results from a Phase 2 Study of Injectable Omega Interferon plus Ribavirin for the Treatment of Hepatitis C Genotype-1," NLV Partners Press Coverage Portfolio News (Apr. 12, 2007) (Press Release).
Quianzon et al., "Lixisenatide-Once-daily Glucagon-like Peptide-1 Diabetes," US Endocrinology 7(2):104-109 (2011).
Ratner et al., "Dose-dependent effects of the one-daily GLP-1 receptor agonist lixisenatide in patients with Type 2 diabetes inadequately controlled with metfmmin: a randomized, double-blind, placebo-controlled trial," Diabetic Medicine 27(9):1024-1032 (Sep. 2010).
Roberts et al., "The Evolution of the Type I Interferons1," J. Interferon Cytokine Res. 18(10):805-816 (Oct. 1998).
Rohloff et al., "DUROS Technology Delivers Peptides and Proteins at Consistent Rate Continuously for 3 to 12 Months," J. Diabetes Sci. & Tech., 2(3):461-467 (May 1, 2008).
"Sequence Listings for International Patent Application Publication No. W02009109927, WIPO Patentscope", http://patentscope.wipo.int/search/docservicepdf_pct/id00000008776887, 1 page (last visited Nov. 14, 2012).
Shire et al., "Challenges in the Development of High Protein Concentration Formulations," J. Pharm. Sci. 93:1390-1402 (2004).
Smith, "Peripheral Neuro-hormones as a Strategy to Treat Obesity," oral presentation at the 2007 Cardiometabolic Health Congress in Boston, MA, pp. 1-35 (Sep. 26-29, 2007).
Written Opinion for International Patent Application No. PCT/US2009/005629 (corresponding to U.S. Appl. No. 12/587,946), 5 pages (dated Apr. 15, 2011).
Zhang et al., "Efficacy observations of different dosages of interferon to treat 150 Hepatitis B carriers," Current Physician 2(12):45-46 (1997).
Pratley et al., "Targeting Incretins in Type 2 Diabetes: Role of GLP-1 Receptor Agonists and DPP-4 Inhibitors," Rev. Diabet. Stud., 5(2):73-94 (2008).
Gonzalez, et al., "Hemoglobin A1c: A Reliable and Accurate Test for Diabetes Care? A Prospective Study in Mexico," Salud Publica Mex 55:462-468 (2013).
Ahn et al., "A New Approach to Search for the Bioactive Confirmation of Glucagon: Positional Cyclization Scanning" Journal of Medicinal Chemistry, vol. 44, No. 19, (2001): 3109-3116.
"Abstracts 2007," Diabetologia Clinical & Experimental Diabetes & Metabolism, Springer, Berlin, Germany, vol. 50 S243 (Aug. 21, 2007) (paragraph [0586]) (X0002538652).
Jetschmann et al., "Open-label rising-dose study of omega interferon in IFN-naive patients with chronic hepatitis C," Gastroenterology 122:A278-A347 (Apr. 1, 2002) (Abstract M1454).
Bray, "Gut Signals and Energy Balance: Ghrelin, Peptide YY, Leptin, and Amylin," (Dec. 19, 2007) (slides and transcript for presentation at Medscape CME).
"Implantable infusion pumps: technology poised for takeoff," BBI Newsletter 17(12):209-211 (Dec. 1994).

Adamson et al., "Phase I trial and pharmacokinetic study of all-trans-retinoic acid administered on an intermittent schedule in combination with interferon-alpha2a in pediatric patients with refractory cancer," J. Clin. Oncol. 15(11):3330-3337 (Nov. 1997).
Adolf et al., "Monoclonal antibodies and enzyme immunoassays specific for human interferon (IFN) ω1: evidence that IFN-ω1 is a component of human leukocyte IFN," Virology 175(2):410-471 (Apr. 1990).
Adolf et al., "Antigenic structure of human interferon ω1 (Interferon αII1): comparison with other human interferons," J. Gen. Virol. 68(6):1669-1676 (Jun. 1987).
Adolf et al., "Purification and characterization of natural human interferon ω1," J. Bio. Chem. 265(16):9290-9295 (Jun. 1990).
Adolf et al., "Human interferon ω1: isolation of the gene, expression in Chinese hamster ovary cells and characterization of the recombinant protein," Biochim. Biophys. Acta 108(9):167-174 (Jun. 1991).
Andrx Pharmaceuticals, LLC, ANDA for Concerta® Extended-Release Tablets, 6 pages (correspondence dated Sep. 6, 2005).
ASTM International, Annual Book of ASTM Standards, 8.02:208-211, 584-587 (1984).
Ansel et al., "Dosage Form Design: Pharmaceutical and Formulation Considerations," Pharmaceutical Dosage Forms and Drug Delivery Systems, Ch. 3 at 87-92 (7th ed. Lippincott Williams & Wilkins 1999).
Ansel et al., "Modified-Release Dosage Forms and Drug Delivery Systems," Pharmaceutical Dosage Forms and Drug Delivery Systems, Ch. 8 at 229-243 (7th ed. Lippincott Williams & Wilkins 1999).
Aulitzky, "Successful Treatment of Metastatic Renal Cell Carcinoma With a Biologically Active Dose of Recombinant Interferon-Gama," Journal of Clinical Oncology 7(12):1875-1884 (1989).
Hauck, "Engineer's Guide to Plastics," Materials Engineering 5(72):38-45 (Jul. 17, 1972).
Bailon et al., "Rational Design of a Potent, Long-lasting Form of Interferon: A 40 kDa Branched Polyethylene Glycol-conjugated Interferon Alpha-2a for the Treatment of Hepatitis C," Bioconjugate Chemistry 12(2):195-202 (2001).
Bakan et al., "Physicochemical Characterization of a Synthetic Lipid Emulsion for Hepatocyte-Selective Delivery of Lipophilic Compounds: Application to Polyiodinated triglycerides as Contrast Agents for Computed Tomography," J. Pharm. Sci., 85(9):908-914 (1996).
Bakhtiar et al, "Taking Delivery," Soap Perfumery & Cosmetics 76(3):59-65 (2003) (liposomes in cosmetic delivery systems).
Balkwill, F., "Interferons," Lancet 1(8646):1060-1063 (May 1989).
Bauer et al., "Non-aqueous emulsions as vehicles for capsule fillings," Drug Dev. & Industrial Pharmacy 10(5):699-712 (1984).
Bekkering et al., "Estimation of early hepatitis C viral clearance in patients receiving daily interferon and ribavirin therapy using a mathematical model," Hepatology 33(2):419-423 (Feb. 2001).
Bell et al., "Hamster preproglucagon contains the sequence of glucagon and two related peptides," Nature 302:716-718 (1983).
Bell et al, "Impact of moisture on thermally induced denaturation and decomposition of lyophilized bovine somatotropin," Drug Delivery Research & Dev. Biopolymers, (35):201-209 (1995).
Bertoncello et al., "Haematopoietic radioprotection by Cremophor EL: a polyethoxylated castor oil," Int. J. Radiat. Biol. 67(1):57-64 (1995).
Bohlinder et al., "Use and characteristics of a novel lipid particle-forming matrix as a drug-carrier system," Euro. J. Pharm. Sci. 2(4):271-279 (1994).
Bolinger et al., "Recombinant interferon γ for treatment of chronic granulomatous disease and other disorders," Clin. Pharm. 11(10):834-850 (Oct. 1992).
Bonkovsky et al., "Outcomes research in chronic viral hepatitis C: effects of interferon therapy," Can. J. Gastroenterol. 14(Supp. B):21B-29B (Jul.-Aug. 2000).
Borden et al., "Second-generation interferons for cancer: clinical targets," Semin. Cancer Biol. 10(2):125-144 (Apr. 2000).
Boué et al., "Antiviral and antiluteolytic activity of recombinant bovine IFN-ω1 obtained from Pichia pastoris," J. Interferon & Cytokine Res. 20:677-683 (2000).

(56) References Cited

OTHER PUBLICATIONS

Buckwold et. al. "Antiviral activity of CHO-SS cell-derived human omega interferon and other human interferons against HCV RNA replicons and related viruses," Antiviral Res. 73(2):118-25 (Feb. 2007) (Epub Sep. 11, 2006).
Cantor, "Theory of lipid monolayers comprised of mixtures of flexible and stiff amphiphiles in anthermal solvents: fluid phase coexistence," J. Chem. Physics 104(20):8082-8095 (1996).
CAS No. 56-81-5 (Nov. 16, 1984).
Chang et al., "Biodegradable polyester implants and suspension injection for sustained release of a cognitive enhancer," Pharm. Tech. 20(1):80-84 (1996).
Chapman et al., "Physical Studies of Phospholipids. VI. Thermotropic and Lyotropic Mesomorphism of Some 1,2-Diacylphosphatidylcholines (lecithins)," Chem. & Physics of Lipids 1(5):445-475 (1967).
Chaumeil, "Micronization: a method of improving the bioavailability of poorly soluble drugs," Methods & Findings in Experimental & Clinical Pharmacology 20(3):211-215 (1998).
Clark et al., "The diabetic Zucker fatty rat," Proc. Soc. Exp. Biol. 173(1):68-75 (1983).
Condino-Neto, "Interferon-γ improves splicing efficiency of CYBB gene transcripts in an interferon responsive variant of chronic granulomatous disease due to a splice site consensus region mutation," Blood 95(11):3548-3554 (Jun. 2000).
Darney, "Subdermal progestin implant contraception," Current Opinion in Obstetrics & Gynecology 3:470-476 (1991).
DAS et al., "Reviewing Antisense Oligonucleotide Therapy: Part 2, Delivery Issues," BioPharm, 2(11):44-51 (1999).
Dash et al., "Therapeutic applications of implantable drug delivery systems," Journal of Pharmacological and Toxicological Methods, 40(1):1-12 (1998).
Davis et al., "Durability of viral response to interferon alone or in combination with oral ribavirin in patients with chronic hepatitis C," Prog. Abstr. 50th Annu. Mtg. Postgrad. Courses Am. Assn. Study Liver Dis., Dallas, TX (Nov. 5-9, 1999)(Abstract 570 ).
Deacon et al., "GLP-1-(9-36) amide reduces blood glucose in anesthetized pigs by a mechanism that does not involve insulin secretion," Am. J. Physiol. Endocrinol. Metab., 282:E873-E879 (2002).
Desai et al., "Protein structure in the lyophilized state: a hydrogen isotope exchange/NMR study with bovine pancreatic trypsin inhibitor," J. Am. Chem. Soc. 116(21):9420-9422 (1994).
Di Marco et al., "Combined treatment of relapse of chronic hepatitis C with high-dose α-2B interferon plus ribavirin for 6 or 12 months," Prog. Abstr. 50th Annu. Mtg. Postgrad. Courses Am. Assn. Study Liver Dis., Dallas, TX (Nov. 5-9, 1999)(Abstract 569).
Dorr et al., "Phase I-II trial of interferon-alpha 2b by continuous subcutaneous infusion over 28 days," J. Interferon Res. 8:717-725 (1988).
Uhlig et al., "The electro-osmotic acutation of implantable insulin micropumps," J. Biomed. Materials Res. 17:931-943 (1983).
Efendic et al., "Overview of incretin hormones," Horm. Metab. Res., 36(11-12):742-746 (2004).
Eissele et al., "Rat gastric somatostatin and gastrin release: interactions of exendin-4 and truncated glucagon-like peptide-1 (GLP-1) amide," Life Sci., 55(8):629-634 (1994).
Elias et al., "Infusional Interleukin-2 and 5-fluorouracil with subcutaneous interferon-α for the treatment of patients with advanced renal cell carcinoma: a southwest oncology group Phase II study," Cancer 89(3):597-603 (Aug. 2000).
Eng et al., "Isolation and characterization of exendin-4, an exendin-3 analogue, from Heloderma suspectum venom. Further evidence for an exendin receptor on dispersed acini from guinea pig pancreas," J. Biol. Chem., 267(11):7402-7405 (1992).
Eng et al., "Purification and structure of exendin-3, a new pancreatic secretagogue isolated from Heloderma horridum venom," J. Biol. Chem., 265(33):20259-20262 (1990).
Eppstein et al., "Biological activity of liposome-encapsulated murine interferon γ is mediated by a cell membrane receptor," PNAS USA 82:3688-3692 (1985).

Eros et al., "Multiple phase emulsions as controlled drug delivery therapeutic systems," Proc.-Conf. Colloid Chem. 193-196 (1993).
Fang et al., "The impact of baseline liver histology on virologic response to interferon α-2b±ρ ribavirin therapy in patients with chronic hepatitis C," Prog. Abstr. 50th Annu. Mtg. Postgrad. Courses Am. Assn. Study Liver Dis., Dallas, TX (Nov. 5-9, 1999)(Abstract 572).
Felker et al., "The Rate of Transfer of Unesterified Cholesterol from Rat Erythrocytes to Emulsions Modeling Nascent Triglyceride-Rich Lipoproteins and Chylomicrons Depends on the Degree of Fluidity of the Surface," J. Nutritional Biochem. 4(1):630-634 (1993).
Ferenci et al, "Combination of interferon (IFN) induction therapy and ribavirin in chronic hepatitis C," Prog. Abstr. Dig. Dis. Week 2000, San Diego, CA (May 21-24, 2000) (Abstract 977).
Fontaine et al., "Recovery from chronic hepatitis C in long-term responders to ribarivin plus interferon α," Lancet 356(9223):41 (Jul. 2000).
Franchetti et al., "Furanfurin and Thiophenfurin: Two Novel Tiazofurin Analogues. Synthesis, Structure, Antitumor Activity, and Interactions with Inosine Monophosphate Dehydrogenase," J. Medicinal Chem. 38(19):3829-3837 (1995).
Fujii et al., "Effect of phosphatidylcholine on Skin Permeation of Indomethacin from gel prepared with Liquid Paraffin and Hydrogenated Phospholipid," Int'l J. Pharmaceutics 222(1):57-64 (2001).
Fujii et al., "Enhancement of skin permeation of miconazole by phospholipid and dodecyl 2-(N, N-dimethylamino) propionate (DDAIP)," Int'l J. Pharmaceutics 234(1-2):121-128 (2002).
Luft et al., "Electro-osmotic valve for the controlled administration of drugs," Med. & Biological Engineering & Computing 45-50 (Jan. 1978) (non-English with English abstract).
Gan to Kagaku Ryoho, "Phase II study of recombinant leukocyte A interferon (Ro22-8181) in malignant brain tumors," Cancer & Chemotherapy 12(4):913-920 (Apr. 1985) (non-English with English abstract).
Gappa et al., "Juvenile laryngeal papillomatosis—a case report," Pneumologie 45(11):936-938 (Nov. 1991) (XP009079028) (non-English with English abstract).
Gause et al., "Phase I study of subcutaneously administered interleukin-2 in combination with interferon alfa-2a in patients with advanced cancer," J. Clin. Oncol. 14(8):2234-2241 (Aug. 1996).
Ghiglione et al., "How glucagon-like is glucagon-like peptide-1?" Diabetologia 27:599-600 (1984).
Glue et al., "A dose-ranging study of Peg-intron and ribavirin in chronic hepatitis C—safety, efficacy, and virological rationale," Prog. Abstr. 50th Annu. Mtg. Postgrad. Courses Am. Assn. Study Liver Dis., Dallas, TX (Nov. 5-9, 1999)(Abstract 571).
Goke et al., "Exendin-4 is a high potency agonist and truncated exendin-(9-39)-amide an antagonist at the glucagon-like peptide 1-(7-36)-amide receptor of insulin-secreting beta-cells," J. Biol. Chem., 268(26):19650-19655 (1993).
Gonzales et al., "Randomized controlled trial including an initial 4-week 'induction' period during one year of high-dose interferon α-2B treatment for chronic hepatitis C," Prog. Abstr. Dig. Dis. Week 2000, San Diego, CA (May 21-24, 2000) (Abstract 975).
Gosland et al., "A phase I trial of 5-day continuous infusion cisplatin and interferon alpha," Cancer Chemother. Pharmacol. 37(1-2):39-46 (1995).
Grant et al., "Combination therapy with interferon-α plus N-acetyl cysteine for chronic hepatitis C: a placebo controlled double-blind multicentre study," J. Med. Virol. 61(4):439-442 (Aug. 2000).
Gutniak et al., "Antidiabetogenic effect of glucagon-like peptide-1 (7-36)amide in normal subjects and patients with diabetes mellitus," N. Engl. J. Med., 326(20):1316-1322 (1992).
Hageman, "The Role of Moisture in Protein Stability, " Drug Dev. & Ind. Pharm. 14(14):2047-2070 (1988).
Heathcote et al., "Peginterferon alfa-2a in Patients With Chronic Hepatitis C and Cirrhosis," New England J. Med. 343(23):1673-1680 (2000).
Reim et al., "Intracellular signaling and antiviral effects of interferons," Dig. Liver Dis. 32(3):257-263 (Apr. 2000).

(56) References Cited

OTHER PUBLICATIONS

Heinrich et al., "Pre-proglucagon messenger ribonucleic acid: nucleotide and encoded amino acid sequences of the rat pancreatic complementary deoxyribonucleic acid," Endocrinol., 115:2176-2181 (1984).
Hellstrand et al., "Histamine and cytokine therapy," Acta Oncol. 37(4):347-353 (1998).
Hellstrand et al., "Histamine and the response to IFN-α in chronic hepatitis C," Interferon Cytokine Res. 18(1):21-22 (Jan. 1998).
Hellstrand et al., "Histamine in immunotherapy of advanced melanoma: a pilot study," Cancer Immunol Immunother. 39(6):416-419 (Dec. 1994).
Hisatomi et al., "Toxicity of polyoxyethylene hydrogenated castor oil 60 (HCO-60) in experimental animals," J. Toxicol. Sci., 18(3):1-9 (1993).
Hodoshima et al., "Lipid nanoparticles for delivering antitumor drugs," International Journal of Pharmaceutics, 146(1):81-92 (1997).
Hoffmann-La Roche Inc., Pegasys® (peginterferon alfa-2a), 15 pages (2002).
Horton et al., "Antitumor effects of interferon-omega: in vivo therapy of human tumor xenografts in nude mice" Cancer Res 59(16):4064-4068 (Aug. 1999).
Hubel et al., "A phase I/II study of idarubicin, dexamethasone and interferon-alpha (1-Dexa) in patients with relapsed or refractory multiple myeloma" Leukemia 11 Suppl 5:S47-S51 (Dec. 1997).
Iacobelli et al., "A phase I study of recombinant interferon-alpha administered as a seven-day continuous venous infusion at circadian-rhythm modulated rate in patients with cancer," Am. J. Clin. Oncol. 18(1):27-31 (1995).
IFNB Multiple Sclerosis Study Group, "Interferonβ-1b is effective in relapsing-remitting multiple sclerosis," Neurology 43(4):655-667 (Apr. 1993).
Interiviune® Inc., Infergen® (Interferon alfacon-1), 5 pages (2002).
"Introduction to Antibodies", http://www.chemicon.com/resource/ANT101/a1.asp, 8 pages (retrieved May 2, 2007).
Isaacs et al., "Virus interference. I. The interferon," Pro. R. Soc. Lond. B. Biol. Sci. 147:258-267 (1957).
Jain et al., "Controlled delivery of drugs from a novel injectable in situ formed biodegradable PLGA microsphere system," J. Microencapsulation 17(3):343-362 (2000).
Jordan et al., "Guidelines for Antiemetic Treatment of Chemotherapy-Induced Nausea and Vomiting: Past, Present and Future Recommendations," The Oncologist 12(9):1143-1150 (2007).
Kabalnov et al., "Macroemulsion type and stability of alkane-water-phospholipid systems," Abstracts of Papers, Part 1, 210th ACS National Meeting, 0-8412-3222-9, American Chemical Society, Chicago, IL (Aug. 20-24, 1995) (Abstract only).
Kabalnov et al., "Phospholipids as Emulsion Stabilizers.2. Phase Behavior Versus Emulsion Stability," Journal of Colloid and Interface Science 184(1):227-235 (1996).
Khalili et al., "Interferon and ribavirin versus interferon and amantadine in interferon nonresponders with chronic hepatitis C," Am. J. Gastroenterol. 95(5):1284-1289 (May 2000).
Kildsig et al., "Theoretical Justification of Reciprocal Rate Plots in Studies of Water Vapor Transmission through Films," J. Pharma. Sci. 29(11):1634-01637 (Nov. 17, 1970).
Kirkwood et al., "Interferon alfa-2b adjuvant therapy of high-risk resected cutaneous melanoma: The Eastern Cooperative Oncology Group Trial EST 1684," J. Clin. Oncol. 14(1):7-17 (1996).
Kita et al., "Characterization of a polyethylene glycol conjugate of recombinant human interferon-γ," Drug Des. Deliv. 6(3):157-0167 (Sep. 1990).
Knepp et al, "Identification of antioxidants for prevention of peroxide-mediated oxidation of recombinant human ciliary neurotrophic factor and recombinant human nerve growth factor," J. Pharm. Sci. Tech. 50(3):163-171 (1996).
Knepp et al., "Stability of nonaqueous suspension formulations of plasma derived factor IX and recombinant human alpha interferon at elevated temperatures," Pharma. Res. 15(7):1090-1095 (1998).
Knobler et al., "Systemic α-interferon therapy of multiple sclerosis," Neurology 34(10):1273-1279 (Oct. 1984).
Kovacevic et al., "Treatment of chronic viral hepatitis B in secondary membranoproliferative glomerulonephritis using recombinant α-2 interferon," Maksic Dj Vojnosanit. Pregl. 57(2):235-240 (Mar.-Apr. 2000) (non-English with English abstract).
Kracke et al., "Mx proteins in blood leukocytes for monitoring interferon β-1b therapy in patients with MS," Neurology 54(1):193-199 (Jan. 2000).
Kronenberger et al., "Influence of interferon-α on CD82-expression in HCV-positive patients," Prog. Abstr. Dig. Dis. Week 2000, San Diego, CA (May 21-24, 2000) (Abstract 976).
Krown et al., "Interferons and interferon inducers in cancer treatment," Semin. Oncol. 13(2):207-217 (1986).
Kubes et al., "Cross-species antiviral and antiproliferative activity of human interferon-ω," J. Interferon Res. 14:57-59 (1994).
Kunzi et al., "Role of interferon-stimulated gene ISG-15 in the interferon-ω-mediated inhibition of human immunodeficiency virus replication," J. Interferon Cytokine Res. 16(11):919-927 (Nov. 1996).
Larsson, "Stability of emulsions formed by polar lipids," Progress in the Chemistry of Fats and Other Lipids 16:163-0169 (1978).
Lee et al., "Dynamics of hepatitis C virus quasispecies turnover during interferon-A treatment," Prog. Abstr. Dig. Dis. Week 2000, San Diego, CA (May 21-24, 2000) (Abstract 974).
Lee, "Therapy of hepatitis C: interferon alfa-2A trials," Hepatology 26: 89S-95S (Sep. 1997) (XP000981288).
Lopez et al., "Mammalian pancreatic preproglucagon contains three glucagon-related peptides," Proc. Natl. Acad. Sci. USA, 80(18):5485-5489 (1983).
Lukaszewski et al., "Pegylated α interferon is an effective treatment for virulent Venezuelan equine encephalitis virus and has profound effects on host immune response to infection," J. Virol. 74(11):5006-5015 (Jun. 2000).
Lund et al., "Pancreatic preproglucagon cDNA contains two glucagon-related coding sequences arranged in tandem," Proc. Natl. Acad. Sci. USA, 79(2):345-349 (1982).
Lundberg, "A submicron lipid emulsion coated with amphipathic polyethylene glycol for parenteral administration of paclitaxel (Taxol)," J. Pharm. & Pharmacol. 49(1):16-21 (1997).
Magnuson et al. "Enhanced recovery of a secreted mammalian protein from suspension culture of genetically modified tobacco cells," Protein Expression & Purification 7:220-228 (1996).
Malley et al., "Chronic Toxicity and Oncogenicity of N-Methylpyrolidone (Nmp) in Rats and Mice by Dietary Administration," Drug Chem Toxicol. 24(4):315-38 (Nov. 2001).
Manning et al, "Stability of protein pharmaceuticals," Pharm. Res. 6(11):903-918 (1989).
Marincola et al., "Combination therapy with interferon alfa-2a and interleukin-2 for the treatment of metastatic cancer," J. Clinical Oncol. 13(5):1110-1122 (1995) (X0009078965).
Massey, "Interaction of vitamin E with saturated phospholipid bilayers," Biochem. & Biophys. Res. Comms. 106(3):842-847 (1982).
McHutchison et al., "Interferon α-2b alone or in combination with ribavirin as initial treatment for chronic hepatitis C," N. Engl. J. Med. 339(21):1485-1492 (Nov. 1998).
McHutchison et al., "Open-label phase 1B study of hepatitis C viral dynamics with omega interferon treatment," Hepatology 34(4):A333 (Oct. 1, 2001) (XP004716177) (Abstract Only).
Meter et al., "The glucagon-like peptide-1 metabolite GLP-1-(9-36) amide reduces postprandial glycemia independently of gastric emptying and insulin secretion in humans," Am. J. Physiol. Endocrinol. Metab., 290(6):E1118-E1123 (2006).
Merad et al., "Generation of monocyte-derived dendritic cells from patients with renal cell cancer: modulation of their functional properties after therapy with biological response modifiers (IFN-α plus IL-2 and IL-12)," J. Immunother. 23(3):369-378 (May-Jun. 2000).
Milella et al., "Neutralizing antibodies to recombinant α-interferon and response to therapy in chronic hepatitis C virus infection," Liver 13(3):146-150 (Jun. 1993).

(56) References Cited

OTHER PUBLICATIONS

Mohler, "Primer on electrodeposited coatings," Materials Engineering 5:38-45 (1972).
Mojsov, "Structural requirements for biological activity of glucagon-like peptide-I," Int. J. Peptide Protein Research, 40:333-343 (1992).
Morgan, "Structure and Moisture Permeability of Film-Forming Poloyers," Ind. Eng. Chem. 45(10):2296-2306 (1953).
Motzer et al., "Phase I trial of 40-kd branched pegylated interferon alfa-2a for patients with advanced renal cell carcinoma," J. Clinical Oncol. 19(5):1312-1319 (2001).
Nauck et al., "Normalization of fasting glycaemia by intravenous GLP-1 ([7-36 amide] or [7-37]) in type 2 diabetic patients," Diabet. Med., 15(11):937-945(1998).
Neumann et al., "Hepatitis C Viral Dynamics In Vivo and the Antiviral Efficacy of Interferon-alpha Therapy," Science 282:103-107 (Dec. 1998).
Nieforth et al., "Use of an indirect pharmacodynamic stimulation model of MX protein induction to compare in vivo activity of interferon-α-2a and a polyethylene glycol-modified derivative in healthy subjects," Clin. Pharmacol. Ther. 59(6):636-646 (Jun. 1996).
Norden et al., "Physicochemical characterization of a drug-containing phospholipid-stabilized o / w emulsion for intravenous administration," Eur. J. Pharm. Sci. 13(4):393-401 (2001).
Olaso et al., "Early prediction of lack of response to treatment with interferon and interferon plus ribavirin using biochemical and virological criteria in patients with chronic hepatitis C," Esp. Quimioter. 12(3):220-228 (Sep. 1999) (non-English with English abstract).
Ortiz et al., "A differential scanning calorimetry study of the interaction of α-tocopherol with mixtures of phospholipids," Biochim et Biophys Acta 898(2):214-222 (1987).
Panitch, "Interferons in multiple sclerosis," Drugs 44(6):946-962 (Dec. 1992).
Patzelt et al., "Identification and processing of proglucagon in pancreatic islets," Nature, 282:260-266 (1979).
Peterson et al., "Zucker Diabetic Fatty Rat as a Model for Non-insulin-dependent Diabetes Mellitus," ILAR Journal, 32(3):16-19 (1990).
Peterson et al., "Neuropathic complications in the Zucker diabetic fatty rat (ZDF/Drt-fa)," Frontiers in diabetes research. Lessons from Animal Diabetes III, Shafrir, E. (ed.), pp. 456-458, Smith-Gordon, London (1990).
Pimstone et al., "High dose (780 MIU/52 weeks) interferon monotherapy is highly effective treatment for hepatitis C," Prog. Abstr. Dig. Dis. Week 2000, San Diego, CA (May 21-24, 2000) (Abstract 973).
Plauth et al, "Open-label phase II study of omega interferon in previously untreated HCV infected patients," Hepatology 34(4):A331 (Oct. 1, 2001) (X004716169) (Abstract Only).
Plauth et al, "Open-label study of omega interferon in previously untreated HCV-infected patients," J. Hepatology 36(Supp. 1):125 (Apr. 2002) (X0002511882) (Abstract Only).
Pohl et al., "Molecular cloning of the helodermin and exendin-4 cDNAs in the lizard. Relationship to vasoactive intestinal polypeptide/ pituitary adenylate cyclase activating polypeptide and glucagon-like peptide 1 and evidence against the existence of mammalian homologues," J. Biol. Chem., 273(16):9778-9784 (1998).
Poynard et al., "Is an 'a la carte' combined interferon α 2b plus ribavirin possible for the first line treatment in patients with chronic hepatitis C," Hepatology 31(1):211-218 (Jan. 2000).
Poynard et al., "Randomized trial of interferon α 2b plus ribavirin for 48 weeks or for 24 weeks versus interferon α 2b plus placebo for 48 weeks for the treatment of chronic infection with hepatitis C virus," Lancet 352(9138):1426-1432 (Oct. 1998).
"Intarcia Presents Positive ITCA 650 Phase 2 Study Results for Type 2 Diabetes at EASD," Intarcia Therapeutics, Inc. (Sep. 22, 2010) (Press Release).
Quesada et al., "Interferons in Hematological Malignancies", eds. Baron et al., U. Tex. 487-495 (1987).
Quintanar-Guerrero et al., "Applications of the ion-pair concept to hydrophilic substances with special emphasis on peptides," Pharm. Res. 14(2):119-127 (1997).
Rajkumar et al., "Phase I evaluation of radiation combined with recombinant interferon alpha-2a and BCNU for patients with high-grade glioma," Int'l J. Radiat. Oncol. Biol. Phys. 40(2):297-302 (Jan. 15, 1998).
Roche Pharmaceuticals, Roferon®-A (Interferon alfa-2a, recombinant), 22 pages (2003).
Roff et al., "Handbook of Common Polymers", Cleveland Rubber Co. 72 pages (1971).
Rogers et al., "Permeability Valves," Ind. & Eng. Chem. 49(11):1933-1936 (Nov. 17, 1957).
Roman et al., "Cholestasis in the rat by means of intravenous administration of cyclosporine vehicle, Cremophor EL," Transplantation 48(4):554-558 (1989).
Roth et al., "High Dose Etretinate and Interferon-alpha—A Phase I Study in Squamous Cell Carcinomas and Transitional Cell Carcinomas," Acta Oncol. 38(5):613-617 (1999).
Roth et al., "Combination therapy with amylin and peptide YY[3-36] in obese rodents: anorexigenic synergy and weight loss additivity," Endocrinol. 148(12):6054-61 (Dec. 2007).
Schepp et al., "Exendin-4 and exendin-(9-39)NH12: agonist and antagonist, respectively, at the rat parietal cell receptor for glucagon-like peptide-1-(7-36)NH2," Eur. J. Pharmacol., 269(2):183-191 (1994).
Schering Corp., Intron® A for Injection, 6 pages (2001).
Schering Corp., PEG-Intron™ (Peginterferon alfa-2b) Powder for Injection, 29 pages (2003).
Schmalfub et al., "Modification of drug penetration into human skin using microemulsions," J. Controlled Release 46(3):279-285 (1997).
Sen et al., "The interferon system: a bird's eye view of its biochemistry," J. Biol. Chem. 267(8):5017-5020 (Mar. 1992).
Shiffman et al., "A decline in HCV-RNA level during interferon or interferon/ribavirin therapy in patients with virologic nonresponse is associated with an improvement in hepatic histology," Prog. Abstr. 50th Annu. Mtg. Postgrad. Courses Am. Assn. Study Liver Dis., Dallas, TX (Nov. 5-9, 1999) (Abstract 567).
Shima et al., "Serum total bile acid level as a sensitive indicator of hepatic histological improvement in chronic hepatitis C patients responding to interferon treatment," J. Gastroenterol. Hepatol. 15(3):294-299 (Mar. 2000).
Shiratori et al., "Histologic improvement of fibrosis in patients with hepatitis C who have sustained response to interferon therapy," Ann. Int. Med. 132(7):517-524 (Apr. 2000).
Simon et al., "A longitudinal study of T1 hypointense lesions in relapsing MS: MSCRG trial of interferon β1a," Neurology 55(2):185-192 (Jul. 2000).
Sparks et al., "Lipoprotein alterations in 10- and 20-week-old Zucker diabetic fatty rats: hyperinsulinemic versus insulinopenic hyperglycemia," Metabolism, 47(11):1315-1324 (1998).
Sulkowski et al., "Pegylated Interferon Alfa-2A (Pegasys™) and Ribavirin Combination Therapy for Chronic Hepatitis C: A Phase II Open-Label Study," Gastroenterology 118(4, Supp. 2) (2000) (Abstract 236).
Sulkowski et al., "Peginterferon-α-2a (40kD) and ribavirin in patients with chronic hepatitis C: a phase II open label study," Biodrugs 16(2):105-109 (2002).
Talpaz et al., "Phase I study of polyethylene glycol formulation of interferon alpha-2B (Schering 54031) in Philadelphia chromosome-positive chronic myelogenous leukemia," Blood 98(6):1708-1713 (2001).
Talsania et al., "Peripheral exendin-4 and peptide YY(3-36) synergistically reduce food intake through different mechanisms in mice," Endocrinology 146(9):3748-56 ( Sep. 2005).
Tanaka et al., "Effect of interferon therapy on the incidence of hepatocellular carcinoma and mortality of patients with chronic hepatitis C: a retrospective cohort study of 738 patients," Int. J. Cancer 87(5):741-749 (Sep. 2000).
Tong et al., "Prediction of response during interferon α 2b therapy in chronic hepatitis C patients using viral and biochemical characteristics: a comparison," Hepatology 26(6):1640-01645 (Dec. 1997).

(56) References Cited

OTHER PUBLICATIONS

Touza Rey et al., "The clinical response to interferon-γ in a patient with chronic granulomatous disease and brain abscesses due to Aspergillus fumigatus," Ann. Med. Int. 17(2):86-87 (Feb. 2000).
Trudeau et al., "A phase I study of recombinant human interferon alpha-2b combined with 5-fluorouracil and cisplatin in patients with advanced cancer," Cancer Chemother. Pharmacol. 35(6):496-500 (1995).
Tseng et al., "Glucose-dependent insulinotropic peptide: structure of the precursor and tissue-specific expression in rat," PNAS USA, 90(5):1992-1996 (1993).
Tsung et al., "Preparation and Stabilization of Heparin/Gelatin Complex Coacervate Microcapsules," J. Pharm. Sci. 86(5):603-7 (May 1997).
Unniappan et al., "Effects of dipeptidyl peptidase IV on the satiety actions of peptide YY," Diabetologia; Clinical and Experimental Diabetes and Metabolism 49(8):1915-1923 (Jun. 27, 2006).
Vokes et al., "A phase I trial of concomitant chemoradiotherapy with cisplatin dose intensification and granulocyte-colony stimulating factor support for advanced malignancies of the chest," Cancer Chemother. Pharmacol. 35(4):304-312 (1995).
Vrabec, "Tympanic membrane perforations in the diabetic rat: a model of impaired wound healing," Otolaryngol. Head Neck Surg., 118(3 Pt. 1):304-308 (1998).
Wang et al., "Preferential interaction of α-tocopherol with phosphatidylcholines in mixed aqueous dispersions of phosphatidylcholine and phosphatidylethanolamine," Eur. J. Biochem. 267(21):6362-6368 (2000).
Wang et al., "Ripple phases induced by α-tocopherol in saturated diacylphosphatidylcholines," Archives of Biochem. & Biophys. 377(2):304-314 (2000).
Wang et al., "The distribution of α-tocopherol in mixed aqueous dispersions of phosphatidylcholine and phosphattidylethanolamine," Biochimica et Biophysica Acta-Biomembranes 1509(1-2):361-372 (2000).
Wang et al, "Parenteral formulations of proteins and peptides: stability and stabilizers," J. Parenter. Sci. Technol. 42(2S):S4-S26 (1988).
Weinstock-Guttman et al., "What is new in the treatment of multiple sclerosis?" Drugs 59(3):401-410 (Mar. 2000).
Weissmann et al., "The interferon genes," Prog. Nucleic Acid Res. Mol. Biol. 33:251-300 (1986).
Wright et al., "Preliminary experience with α-2b-interferon therapy of viral hepatitis in liver allograft recipients," Transplantation 53(1):121-123 (Jan. 1992).
Young et al., "Glucose-lowering and insulin-sensitizing actions of exendin-4: studies in obese diabetic (ob/ob, db/db) mice, diabetic fatty Zucker rats, and diabetic rhesus monkeys (Macaca mulatta)," Diabetes, 48(5):1026-1034 (1999).
Younossi et al., "The role of amantadine, rimantadine, ursodeoxycholic acid, and NSAIDs, alone or in combination with α interferons, in the treatment of chronic hepatitis C," Semin. Liver Dis. 19(Supp. 1):95-102 (1999).
Yu et al., "Preparation, characterization, and in vivo evaluation of an oil suspension of a bovine growth hormone releasing factor analog," J. Pharm. Sci. 85(4):396-401 (1996).
Zeidner et al., "Treatment of FeLV-induced immunodeficiency syndrome (feLV-FAIDS) with controlled release capsular implantation of 2',3'-dideoxycytidine," Antivir. Res. 11(3):147-0160 (Apr. 1989).
Zein, "Interferons in the management of viral hepatitis," Cytokines Cell Mol. Ther. 4(4):229-241 (Dec. 1998).
Zeuzem et al., "Peginterferon Alfa-2a in Patients with Chronic Hepatitis C," New Engl. J. Med. 343(23):1666-1672 (2000).
Zeuzem et al., "Hepatitis C virus dynamics in vivo: effect of ribavirin and interferon αon viral turnover," Hepatology 28(1):245-252 (Jul. 1998).
Zhang et al., "Report on Large Dosage Interferon to Treat 30 Cases of Viral Encephalitis," J. Clinical Pediatrics 14(2):83-84 (1996).

Zhang et al, "A new strategy for enhancing the stability of lyophilized protein: the effect of the reconstitution medium on keratinocyte growth factor," Pharm. Res. 12(10):1447-1452 (1995).
Zheng et al. "Therapeutic Effect of Interferon Varied Dose in Treating Virus Encephalitis," Beijing Med. J. 13(2):80-81 (1998).
Ziesche et al., "A preliminary study of long-term treatment with interferon γ-1b and low-dose prednisolone in patients with idiopathic pulmonary fibrosis," New Engl. J. Med. 341(17):1264-1269 (Oct. 1999).
Sanofi-Aventis U.S. LLC, Prescribing Information for Adlyxin® (Lixisenatide) Injection, for Subcutaneous Use, rev. Jul. 2016, 31 pages.
Amylin Pharmaceuticals, Inc., Prescribing Information for Byetta® (Exenatide) Injection, rev. Oct. 2009, 34 pages.
Astrazeneca Pharmaceuticals LP, Prescribing Information for Bydureon® (Exenatide Extended-Release for Injectable Suspension), rev. Mar. 2015, 60 pages.
Novo Nordisk A/S, Prescribing Information for Victoza® (Liraglutide [rDNA Origin] Injection), Solution for Subcutaneous Use, v. 1, Jan. 2010, 23 pages.
Glaxosmithkline LLC, Prescribing Information for Tanzeum® (Albiglutide) for Injection, for Subcutaneous Use, rev. Jun. 2014, 55 pages.
Eli Lilly & Company, Prescribing Information for Trulicity® (Dulaglutide) Injection, for Subcutaneous Use, rev. Mar. 2015, 19 pages.
Akers, et al., "Formulation Design and Development of Parenteral Suspensions," Journal of Parenteral Science & Technology, 41(3): 88-96 (1987).
Alonso, et al., "Determinants of Release Rate of Tetanus Vaccine from Polyester Microspheres," Pharmaceutical Research, 10(7):945-953 (1993).
Beck, et al., "Poly(dl-lactide-co-glycolide)/norethisterone microcapsules: An injectable biodegradable contraceptive," Biology of Reproduction, 28(1): 186-195 (1983).
Bodmeier and McGinity, "Solvent selection in the preparation of poly(dl-lactide) microspheres prepared by the solvent evaporation method," International Journal of Pharmaceutics, 43(1-2): 179-186 (Apr. 1988).
Cha and Pitt, "A one-week subdermal delivery system for I-methadone based on biodegradable microcapsules," Journal of Controlled Release, 7: 69-78 (1988).
Cha and Pitt, "The acceleration of degradation-controlled drug delivery from polyester microspheres," Journal of Controlled Release, 8: 259-265 (1989).
Cohen, et al., "Controlled delivery systems for proteins based on poly(lactic/glycolic acid) microspheres," Pharmaceutical Research, 8(6): 713-720 (1991).
Conti, et al., "Use of polylactic acid for the preparation of microparticulate drug delivery systems," Journal of Microencapsulation, 9(2): 153-166 (1992).
Hodgman, et al., Eds., Handbook of Chemistry and Physics, 35th Edition, 1024-1025 (1953).
Jalil and Nixon, "Biodegradable poly(lactic acid) and poly(lactide-co-glycolide) microcapsules: Problems associated with preparative techniques and release properties," Journal of Microencapsulation, 7(3): 297-325 (Jul.-Sep. 1990).
Lee and Timasheff, "The stabilization of proteins by sucrose," J. Biological Chem., 256(14): 7193-7201 (Jul. 1981).
Li, et al., "Prediction of solvent removal profile and effect on properties for peptide-loaded PLGA microspheres prepared by solvent extraction/evaporation method," Journal of Controlled Release, 37: 199-214 (1995).
Maa and Hsu, "Liquid-liquid emulsification by static mixers for use in microencapsulation," Journal of Microencapsulation, 13(4): 419-433 (Jul.-Aug. 1996).
Maulding, et al., "Biodegradable microcapsules: Acceleration of polymeric excipient hydrolytic rate by incorporation of a basic medicament," Journal of Controlled Release, 3: 103-117 (1986).
Mehta, et al.,"Peptide containing microspheres from low molecular weight and hydrophilic poly(d,l-lactide-co-glycolide)," Journal of Controlled Release, 41: 249-257 (1996).

(56) References Cited

OTHER PUBLICATIONS

Sah, et al., "A novel method of preparing PLGA microcapsules utilizing methylethyl ketone," Pharmaceutical Research, 13(3): 360-367 (1996).

Sato, et al., "Porous biodegradable microspheres for controlled drug delivery. I. Assessment of processing conditions and solvent removal techniques," Pharmaceutical Research, 5(1): 21-30 (1988).

Szayna, et al., "Exendin-4 decelerates food intake, weight gain, and fat deposition in Zucker rats," Endocrinology, 141(6): 1936-1941 (2000).

Thomasin, et al., "A contribution to overcoming the problem of residual solvents in biodegradable microspheres prepared by coacervation," Eur. J. Pharm. Biopharm., 42(1): 16-24 (1996).

van Santbrink and Fauser, "Urinary follicle-stimulating hormone for normogonadotropic colomiphene-resistant anovulatory infertility: Prospective, randomized comparison between low dose step-up and step-down dose regimens," J. Clin. Endocrin. Metab., 82(11): 3597-3602 (1997).

Tracy et al., "Factors affecting the degradation rate of poly(lactide-co-glycolide) microspheresin vivo and in vitro." Biomaterials. 20(11:): 1057-1062 (1999).

Ertl et al., "Poly (DL-lactide-co-glycolide) microspheres as carriers for peptide vaccines," Vaccine 14(9):879-885.(1996).

Thompson et al., "Biodegradable microspheres as a delivery system for rismorelin porcine, a porcine-growth-hormone-releasing hormone," Journal of Controlled Release 43(1):9-22 (1997).

Glumetza Brochure 2009, 13 Pages.

Erowid,"Introduction to the Federal Controlled Substance Analog Act" 2001, 4 pages.

Li et al. ("Glucagon-Like Peptide-I Receptor Agonists Versus Insulin Glargine for Type 2 Diabetes Mellitus: a Systematic Review and Meta-Analysis of Randomized Controlled Trials" in Current Therapeutic Research, vol. 71, No. 4, Aug. 2010.

Georgios, et al., "Pharmacokinetics and Tolerability of Exenatide Delivered by 7-Day Continuous Subcutaneous Infusion in Healthy Volunteers", Advances in Therapy, Health Communications, Metuchen, NJ, US, vol. 32, No. 7, Jul. 10, 2015, pp. 650-661.

Yu et al., "Glucagon-like peptide 1 based therapy for type 2 diabetes", World Journal of Pediatrics vol. 4, No. 1, Feb. 1, 2008, pp. 8-13.

Taylor et al., "Day-long subcutaneous infusion of exenatide lowers glycemia in patients with type 2 diabetes", Horm Metab Res 37: 627-632 (2005).

Gao et al., "Target-Mediated Pharmacokinetic and Pharmacodynamic Model of Exendin-4 in Rats, Monkeys. and Humans," Drug Metabolism and Disposition, vol. 40, No. 5, pp. 990-997 (2012).

* cited by examiner

His-Ala-Glu-Gly-Thr-Phe-Thr-Ser-Asp-Val-
Ser-Ser-Tyr-Leu-Glu-Gly-Gln-Ala-Ala-Lys-
Glu-Phe-Ile-Ala-Trp-Leu-Val-Lys-Gly-Arg-NH$_2$
(SEQ ID NO: 1)

Figure 1A

His-Gly-Glu-Gly-Thr-Phe-Thr-Ser-Asp-Leu-
Ser-Lys-Gln-Met-Glu-Glu-Glu-Ala-Val-Arg-
Leu-Phe-Ile-Glu-Trp-Leu-Lys-Asn-Gly-Gly-
Pro-Ser-Ser-Gly-Ala-Pro-Pro-Pro-Ser-NH$_2$
(SEQ ID NO: 2)

Figure 1B

SEQUENCE LISTING

<160> NUMBER OF SEQ ID NOS: 2

<210> SEQ ID NO 1
<211> LENGTH: 30
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 39
<212> TYPE: PRT
<213> ORGANISM: Artificial Sequence
<220> FEATURE:
<223> OTHER INFORMATION: Synthetic Polypeptide sequence, exenatide,
      having the exendin-4 polypeptide sequence from Heloderma suspectum

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

COMPOSITIONS, DEVICES AND METHODS OF USE THEREOF FOR THE TREATMENT OF CANCERS

CROSS REFERENCE TO RELATED APPLICATIONS

This application is a continuation of U.S. patent application Ser. No. 14/525,201, filed on Oct. 27, 2014, which is a continuation of U.S. patent application Ser. No. 13/372,326, filed Feb. 13, 2012, now abandoned, which claims the benefit of U.S. Provisional Application No. 61/443,628, filed Feb. 16, 2011. The contents of the aforementioned patent applications are herein incorporated by reference in their entireties.

TECHNICAL FIELD

The present invention relates to formulations and methods for treating cancer. Aspects of the present invention provide formulations of glucagon-like peptide-1 (GLP-1) receptor agonists for use in mammals for the treatment of cancers.

INCORPORATION BY REFERENCE OF SEQUENCE LISTING

The contents of the text file named "ITCA-040C01US_ST25", which was created on Oct. 27, 2014 and is 1,236 bytes in size, are hereby incorporated by reference in their entireties.

BACKGROUND OF THE INVENTION

Glycolysis is the metabolic pathway that converts glucose into pyruvate. The free energy released in this process is used to form the high-energy compounds ATP and NADH. Increased aerobic glycolysis is seen in a variety of cancer cells, a phenomenon known as the Warburg theory. Under aerobic conditions, some tumor cells produce as much as 60% of their ATP through glycolysis (Nakashima et al., Cancer Res. (1984) 44:5702-5706) as opposed to normal cells which normally generate ATP through mitochondrial oxidative phosphorylation. In addition to increased aerobic glycolysis, increased glycolysis is also seen in tumors that reach a size that exceeds the capacity of blood supply due to hypoxia. For a review of the Warburg theory and implications thereof, see, e.g., Chen et al., J. Bioenerg. Biomenzbr. (2007) 39:267-274.

Glucagon-like peptide-1 (GLP-1) is an important hormone and a fragment of the human proglucagon molecule. GLP-1 is rapidly metabolized by a peptidase (dipeptidyl-peptidase IV or DPP-IV). A fragment of GLP-1, glucagon-like peptide-1 (7-36) amide (also known as GLP-1 (7-36) amide, glucagon-like insulinotropic peptide, or GLIP) is a gastrointestinal peptide that potentiates the release of insulin in physiologic concentrations (Gutniak et al., N Engl J Med (1992) 14:326(20):1316-22). Food intake, as well as stimulation of the sympathetic nervous system, stimulates secretion of GLP-1 in the small intestine of mammals. Further, GLP-1 stimulates the production and secretion of insulin, the release of somatostatin, glucose utilization by increasing insulin sensitivity, and, in animal studies, also stimulates beta-cell function and proliferation. GLP-1(7-36)amide and GLP-1(7-37) normalize fasting hyperglycemia in type 2 diabetic patients (Nauck, M. A., et al., Diabet. Med. 15(11): 937-45 (1998)).

Exendin-4, a GLP-1 receptor agonist, is a molecule purified from Heloderma suspectuni venom (Eng, et al., Biol. Chem. (1992) 267:7402-7405) and shows structural relationship to the hormone GLP-1(7-36)amide. Exendin-4 and truncated exendin-(9-39)amide specifically interact with the GLP-1 receptor on insulinoma-derived cells and on lung membranes (Goke et al., J Biol. Chem. (1993) 268:19650-19655). Exendin-4 has approximately 53% identity to human GLP-1 (Pohl, et al., J. Biol. Chem. (1998) 273:9778-9784). Unlike GLP-1, however, exendin-4 is resistant to degradation by DPP-IV. A glycine substitution confers resistance to degradation by DPP-1V (Young, et al., Diabetes (1999) 48(5):1026-1034).

The increased dependency of cancer cells on the glycolytic pathway is an important metabolic difference between normal and malignant cells. The present invention provides a unique solution to disrupting cancer cell energy reliance on the glycolytic pathway.

SUMMARY OF THE INVENTION

The present invention relates to compositions, devices and methods for treating cancer. The invention utilizes GLP-1 receptor agonists to restrict glucose as an energy source for cancer cells and tumors. The GLP-1 receptor agonists can be used alone or in combination with other beneficial agents, such as anticancer agents, antidiabetic agents and the like, as well as in combination with anticancer treatment modalities, such as radiation, surgery and chemotherapeutic regimens.

Thus, in one aspect the invention relates to a method of treating cancer in a subject in need of such treatment, comprising administering a GLP-1 receptor agonist to said subject.

In certain aspects of the method, the GLP-1 receptor agonist is a glucagon-like peptide-1 (GLP-1), a derivative of GLP-1, or an analog of GLP-1. In some embodiments, the GLP-1 receptor agonist is GLP(7-36)amide comprising the sequence of SEQ ID NO:1.

In other aspects of the invention, the GLP-1 receptor agonist is exenatide, a derivative of exenatide, or an analog of exenatide, such as a synthetic exenatide peptide comprising the sequence of SEQ ID NO:2.

In additional aspects of the invention, the GLP-1 receptor agonist is selected from the group consisting of lixisenatide, liraglutide (VICTOZA™), albiglutide (SYNCRIA™) semaglutide, taspoglutide, BYETTA™, BYDUREON™ and LY2189265. In some embodiments, formulations comprising the GLP-1 receptor agonist are delivered by injection.

In further aspects, the GLP-1 receptor agonist is delivered using an implanted drug delivery device, such as an osmotic delivery device, that provides continuous delivery of a suspension formulation of GLP-1 receptor agonist for a period of at least one month.

In other aspects, the GLP-1 receptor agonist and/or other beneficial agent is provided in a suspension formulation comprising: (a) a particle formulation comprising said GLP-1 receptor agonist and/or beneficial agent; and (b) a vehicle formulation, wherein the particle formulation is dispersed in the vehicle.

In additional aspects, the suspension formulation may further comprise a particle formulation comprising a GLP-1 receptor agonist and/or beneficial agent and one or more stabilizers selected from the group consisting of carbohydrates, antioxidants, amino acids, buffers, and inorganic compounds. The suspension formulation further comprises a non-aqueous, single-phase suspension vehicle comprising one or more polymers and one or more solvents. The suspension vehicle typically exhibits viscous fluid characteristics and the particle formulation is dispersed in the vehicle.

In another embodiment, the suspension formulation comprises a particle formulation comprising a GLP-1 receptor agonist and/or a beneficial agent, a disaccharide (e.g., sucrose), methionine, and a buffer (e.g., citrate), and a non-aqueous, single-phase suspension vehicle comprising one or more pyrrolidone polymer (e.g., polyvinylpyrrolidone) and one or more solvent (e.g., lauryl lactate, lauryl alcohol, benzyl benzoate, or mixtures thereof.

The particle formulations of the present invention may further comprise a buffer, for example, selected from the group consisting of citrate, histidine, succinate, and mixtures thereof.

The particle formulations of the present invention may further comprise an inorganic compound, for example, selected from the group consisting of citrate, histidine, succinate, and mixtures thereof. NaCl, $Na_2SO_4$, $NaHCO_3$, KCl, $KH_2PO_4$, $CaCl_2$, and $MgCl_2$.

The one or more stabilizers in the particle formulations may comprise, for example, a carbohydrate selected from the group consisting of lactose, sucrose, trehalose, mannitol, cellobiose, and mixtures thereof.

The one or more stabilizers in the particle formulations may comprise, for example, a antioxidant selected from the group consisting of methionine, ascorbic acid, sodium thiosulfate, ethylenediaminetetraacetic acid (EDTA), citric acid, cysteins, thioglycerol, thioglycolic acid, thiosorbitol, butylated hydroxanisol, butylated hydroxyltoluene, and propyl gallate, and mixtures thereof.

The one or more stabilizers in the particle formulations may comprise an amino acid.

In one embodiment, the solvent of the suspension vehicle of the present invention is selected from the group consisting of lauryl lactate, lauryl alcohol, benzyl benzoate, and mixtures thereof. An example of a polymer that can be used to formulate the suspension vehicle is a pyrrolidone (e.g., polyvinylpyrrolidone). In a preferred embodiment, the polymer is a pyrrolidone and the solvent is benzyl benzoate.

The suspension formulation typically has an overall moisture content less than about 10 wt % and in a preferred embodiment less than about 5 wt %.

In additional embodiments, a beneficial agent, such as an anticancer agent, in addition to the GLP-1 receptor agonist is delivered to said subject. In certain embodiments, the anticancer agent is a chemotherapeutic agent and/or an anticancer antibody. The additional beneficial agent can be delivered prior to, subsequent to or concurrent with the GLP-1 receptor agonist. In some embodiments, an implantable drug delivery device may be used to deliver formulations comprising an anticancer agent. In one embodiment, the device is an osmotic delivery device.

In some embodiments, implantable drug delivery devices deliver a GLP-1 receptor agonist formulations and/or other beneficial agent formulations at a substantially uniform rate for a period of about one month to about a year. Such devices may, for example, be implanted subcutaneously in convenient locations.

The present invention also includes methods of manufacturing the suspension formulations, particle formulations, suspension vehicles, and devices of the present invention as described herein.

These and other embodiments of the present invention will readily occur to those of ordinary skill in the art in view of the disclosure herein.

BRIEF DESCRIPTION OF THE FIGURES

FIGS. 1A and 1B present the sequences of two representative GLP-1 receptor agonists: FIG. 1A, glucagon-like peptide 1 (7-36)amide (GLP-1(7-36)amide) (SEQ ID NO:1), and FIG. 1B, synthetic exenatide peptide (SEQ ID NO:2).

DETAILED DESCRIPTION OF THE INVENTION

Figure 2:
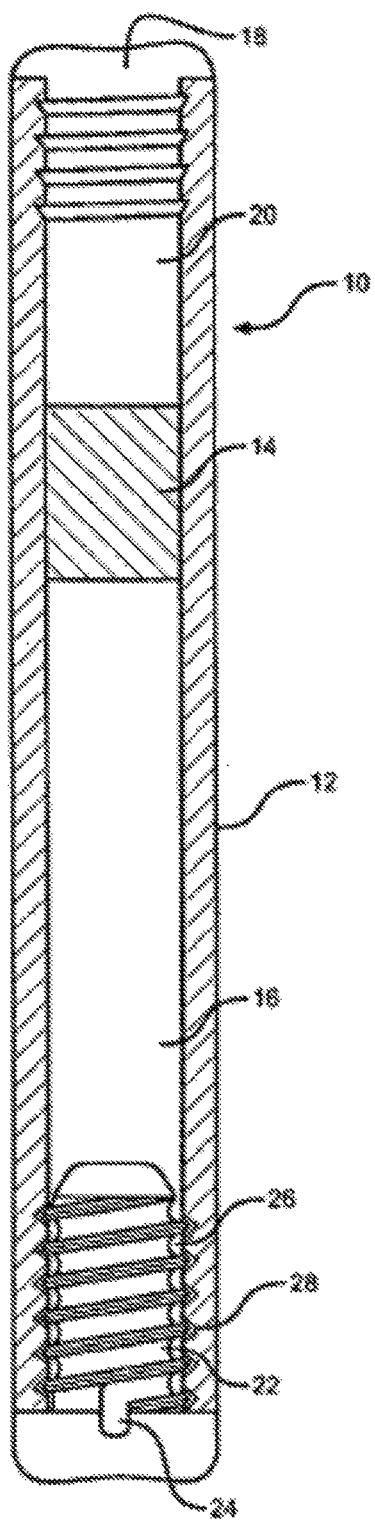
FIG. 2 presents a partial cross-sectional view of one embodiment of an osmotic delivery device useful in the practice of the present invention.

All patents, publications, and patent applications cited in this specification are herein incorporated by reference as if each individual patent, publication, or patent application was specifically and individually indicated to be incorporated by reference in its entirety for all purposes.

1.0.0 Definitions

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a GLP-1 receptor agonist" includes a combination of two or more such molecules, reference to "a peptide" includes one or more peptides, mixtures of peptides, and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The terms "peptide," "polypeptide," and "protein" are used interchangeably herein and typically refer to a molecule comprising a chain of two or more amino acids (e.g., most typically L-amino acids, but also including, e.g., D-amino acids, modified amino acids, amino acid analogs, and/or amino acid mimetic). Peptides may also comprise additional groups modifying the amino acid chain, for example, functional groups added via post-translational modification. Examples of post-translation modifications include, but are not limited to, acetylation, alkylation (including, methylation), biotinylation, glutamylation, glycylation, glycosylation, isoprenylation, lipoylation, phosphopantetheinylation, phosphorylation, selenation, and C-terminal amidation. The term peptide also includes peptides comprising modifications of the amino terminus and/or the carboxy terminus. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl).

The terminal amino acid at one end of the peptide chain typically has a free amino group (i.e., the amino terminus). The terminal amino acid at the other end of the chain typically has a free carboxyl group (i.e., the carboxy terminus). Typically, the amino acids making up a peptide are numbered in order, starting at the amino terminus and increasing in the direction of the carboxy terminus of the peptide.

The phrase "amino acid residue" as used herein refers to an amino acid that is incorporated into a peptide by an amide bond or an amide bond mimetic.

The term "GLP-1 receptor agonist" as used herein refers to an agent capable of binding and activating the GLP-1 receptor. The term includes GLP-1 hormones, as well as GLP-1 peptides, peptide analogs thereof, or peptide derivatives thereof. Also encompassed by the term GLP-1 receptor agonist are other molecules that are capable of binding and activating the GLP-1 receptor, such as without limitation, an exenatide peptide, a peptide analog thereof, or a peptide derivative thereof. Specific examples of preferred GLP-1 receptor agonists include exenatide having the amino acid sequence of exendin-4, GLP-1(7-36)amide, lixisenatide, liraglutide (VICTOZA™), albiglutide (SYNCRIA™), semaglutide, taspoglutide, BYETTA™, BYDUREON™ and LY2189265. The term also includes small molecules capable of binding and activating the GLP-1 receptor. See, e.g., Sloop et al., Diabetes (2010) 59:3099-3107.

The term "anticancer agent" refers to any agent that exhibits anti-tumor activity as defined below. Such agents include, without limitation, chemotherapeutic agents (i.e., a chemical compound or combination of compounds useful in the treatment of cancer), anticancer antibodies, agents that disrupt nucleic acid transcription and/or translation, such as antisense oligonucleotides, small interfering RNA (siRNA), and the like.

By "anti-tumor activity" is intended a reduction in the rate of cell proliferation, and hence a decline in growth rate of an existing tumor or in a tumor that arises during therapy, and/or destruction of existing neoplastic (tumor) cells or newly formed neoplastic cells, and hence a stabilization or decrease in the overall size of a tumor during therapy.

By "antidiabetic agent" is meant any agent that when administered to a subject either directly or indirectly causes a reduction in glucose levels. Such agents include, without limitation, agents for treating types 1 and 2 diabetes, such as but not limited to, GLP-1 receptor agonists; small molecules such as metformin, tolbutamide, glibenclamide, glipizide, gliquidone, glibornuride, tolazamide, sulfonylureas, meglitinides (e.g., repaglinide, and nateglinide); thiazolidinediones (TZDs), such as pioglitazone; $SGLT_1$ and $SGLT_2$ inhibitors; alpha glucosidase inhibitors; amylin (as well as synthetic analogs such as pramlintide); dipeptidyl peptidase IV (DPP-1V) inhibitors (e.g., saxagliptin, sitagliptin, alogliptin and vildagliptin); long/short acting insulins; glucagon receptor antagonists; GRP agonists (e.g., GRP-119 and GRP-40), and the like. Use of oral dipeptidyl peptidase-IV (DPP-IV or DPP-4) inhibitors orally to prevent cleavage of GLP-1 may be particularly useful when the formulation comprises a GLP-1 that is cleavable by dipeptidyl peptidase-1V (see, e.g., U.S. Pat. No. 7,205,409, incorporated herein by reference in its entirety).

An "antibody" intends a molecule that binds to an epitope of interest present in an antigen. The term "antibody" as used herein includes antibodies obtained from both polyclonal and monoclonal preparations, as well as, the following: hybrid (chimeric) antibody molecules (see, for example, Winter et al., Nature (1991) 349:293-299; and U.S. Pat. No. 4,816,567); F(ab')2 and F(ab) fragments; Fv molecules (non-covalent heterodimers, see, for example, Inbar et al., Proc Natl Acad Sci USA (1972) 69:2659-2662; and Ehrlich et al., Biochem (1980) 19:4091-4096); single-chain Fv molecules (sFv) (see, for example, Huston et al., Proc Natl Acad Sci USA (1988) 85:5879-5883); dimeric and trimeric antibody fragment constructs; diabodies; avamers; aptamers; affitins; affitins; anticalins; affibody molecules; designed ankyrin repeat proteins; domain antibodies; minibodies (see, e.g., Pack et al., Biochem (1992) 31:1579-1584; Cumber et al., J Immunology (1992) 149B:120-126); humanized antibody molecules (see, for example, Riechmann et al., Nature (1988) 332:323-327; Verhoeyan et al., Science (1988) 239: 1534-1536; and U.K. Patent Publication No. GB 2,276,169, published 21 Sep. 1994); and, any functional fragments obtained from such molecules, or fusions thereof, wherein such fragments and fusions retain immunological binding properties of the parent antibody molecule. Chimeric antibodies composed of human and non-human amino acid sequences may be formed from monoclonal antibody molecules to reduce their immunogenicity in humans (Winter et al. (1991) Nature 349:293; Lobuglio et al. (1989) Proc. Nat. Acad. Sci. USA 86:4220; Shaw et al. (1987) J Immunol. 138:4534; and Brown et al. (1987) Cancer Res. 47:3577; Rieclunann et al. (1988) Nature 332:323; Verhoeyen et al. (1988) Science 239:1534; and Jones et al. (1986) Nature 321:522; EP Publication No. 519,596, published 23 Dec. 1992; and U.K. Patent Publication No. GB 2,276,169, published 21 Sep. 1994).

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab')2, Fv, and other fragments, as well as chimeric and humanized homogeneous antibody populations, that exhibit immunological binding properties of the parent monoclonal antibody molecule.

As used herein, the term "anti-cancer antibody" encompasses antibodies that have been designed to target cancer cells, particularly cell-surface antigens residing on cells of a particular cancer of interest.

The term "vehicle" as used herein refers to a medium used to carry a compound, e.g., a drug. Vehicles of the present invention typically comprise components such as polymers and solvents. The suspension vehicles of the present invention typically comprise solvents and polymers that are used to prepare suspension formulations further comprising drug particle formulations.

The phrase "phase separation" as used herein refers to the formation of multiple phases (e.g., liquid or gel phases) in the suspension vehicle, such as when the suspension vehicle contacts the aqueous environment. In some embodiments of the present invention, the suspension vehicle is formulated to exhibit phase separation upon contact with an aqueous environment having less than approximately 10% water.

The phrase "single-phase" as used herein refers to a solid, semisolid, or liquid homogeneous system that is physically and chemically uniform throughout.

The term "dispersed" as used herein refers to dissolving, dispersing, suspending, or otherwise distributing a compound, for example, a peptide, in a suspension vehicle.

A "homogeneous suspension" typically refers to a particle that is insoluble in a suspension vehicle and is distributed uniformly in a suspension vehicle.

The phrase "chemically stable" as used herein refers to formation in a formulation of an acceptable percentage of degradation products produced over a defined period of time by chemical pathways, such as deamidation, (usually by hydrolysis), aggregation, or oxidation.

The phrase "physically stable" as used herein refers to formation in a formulation of an acceptable percentage of aggregates (e.g., dimers and other higher molecular weight products). Further, a physically stable formulation does not change its physical state as, for example, from liquid to solid, or from amorphous to crystal form.

The term "viscosity" as used herein typically refers to a value determined from the ratio of shear stress to shear rate (see, e.g., Considine, D. M. & Considine, G. D., Encyclopedia of Chemistry, 4th Edition, Van Nostrand, Reinhold, N.Y., 1984) essentially as follows:

$$F/A = \mu * V/L \quad \text{(Equation 1)}$$

where F/A=shear stress (force per unit area).
μ=a proportionality constant (viscosity), and
V/L=the velocity per layer thickness (shear rate).

From this relationship, the ratio of shear stress to shear rate defines viscosity. Measurements of shear stress and shear rate are typically determined using parallel plate rheometery performed under selected conditions (for example, a temperature of about 37° C.). Other methods for the determination of viscosity include, measurement of a kinematic viscosity using a viscometer, for example, a Cannon-Fenske viscometer, a Ubbelohde viscometer for the Cannon-Fenske opaque solution, or a Ostwald viscometer. Generally, suspension vehicles of the present invention have a viscosity sufficient to prevent particles suspended therein from settling during storage and use in a method of delivery, for example, in an implantable, drug delivery device.

The term "non-aqueous" as used herein refers to an overall moisture content, for example, of a suspension formulation, typically of less than or equal to about 10 wt %, preferably less than or equal to about 5 wt %, and more preferably less than about 4 wt %.

The term "subject" as used herein refers to any member of the subphylum chordata, including, without limitation, humans and other primates, including non-human primates such as rhesus macaque, chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

The terms "drug," "therapeutic agent", and "beneficial agent" are used interchangeably to refer to any therapeutically active substance that is delivered to a subject to produce a desired beneficial effect. In one embodiment of the present invention, the drug is a GLP-1 receptor agonist, e.g., GLP-1 (7-36)amide, exenatide, and derivatives or analogs thereof. The devices and methods of the present invention are well suited for the delivery of polypeptides as well as small molecules and combinations thereof.

The term "osmotic delivery device" as used herein typically refers to a device used for delivery of one or more GLP-1 receptor agonists, or other beneficial agents to a subject, wherein the device comprises, for example, a reservoir (made, for example, from a titanium alloy) having a lumen that contains, in one chamber, a beneficial agent formulation (e.g., comprising one or more beneficial agent) and, in another chamber, an osmotic agent formulation. A piston assembly positioned in the lumen isolates the beneficial agent formulation from the osmotic agent formulation. A semi-permeable membrane (also termed a semi-permeable plug) is positioned at a first distal end of the reservoir adjacent the osmotic agent formulation. A diffusion moderator (which defines a delivery orifice through which the beneficial agent formulation exits the device) is positioned at a second distal end of the reservoir adjacent the suspension formulation. The piston assembly and the diffusion moderator define a chamber that contains the beneficial agent formulation and the piston assembly and the semipermeable membrane define a chamber that contains the osmotic agent formulation. The terms "flow modulator," "diffusion modulator," "flow moderator," and "diffusion moderator" are used interchangeably herein. Typically, the osmotic delivery device is implanted within the subject, for example, subcutaneously (e.g., in the inside, outside, or back of the upper arm; or in the abdominal area). An exemplary osmotic delivery device is the DUROS™ delivery device.

2.0.0 General Overview of the Invention

Before describing the present invention in detail, it is to be understood that this invention is not limited to particular types of drug delivery, particular types of drug delivery devices, particular sources of peptides, particular solvents, particular polymers, and the like, as use of such particulars may be selected in view of the teachings of the present specification. It is also to be understood that the terminology used herein is for the purpose of describing particular embodiments of the invention only, and is not intended to be limiting.

In one aspect, the present invention relates to methods of treating cancer in a subject in need of treatment, including, but not limited to, treating hematological tumors and solid tumors. The method comprises providing delivery of a GLP-1 receptor agonist formulation to a subject in need thereof. In certain embodiments, the GLP-1 receptor agonist formulation is delivered using an osmotic delivery device at a substantially uniform rate. The length of delivery of the formulation is determined based on the cancer being treated. In some embodiments, for example, the administration period is for at least about one month, at least about one month to about one year, at least about three months to about one year, at least about four months to about one year, at least about five months to about one year, at least about six months to about one year, at least about eight months to about one year, at least about nine months to about one year, or at least about 10 months to about one year. The period of administration can also exceed one year if necessary, such as from one year to two years. The method may further include subcutaneously inserting an osmotic delivery device, loaded with the GLP-1 receptor agonist formulation, into the subject.

In other embodiments of the invention, the GLP-1 receptor agonist is delivered parenterally (including by subcutaneous, intravenous, intramedullary, intraarticular, intramuscular, or intraperitoneal injection) rectally, topically, transdermally, intranasally, by inhalation, or orally (for example, in capsules, suspensions, or tablets). Injectable formulations of GLP-1 agonists are known and include, without limitation, lixisenatide, liraglutide (VICTOZA™), albiglutide (SYNCRIA™), semaglutide, taspoglutide, BYETTA™, BYDLIREON™ and LY2189265.

In one embodiment of the present invention the formulation comprises a glucagon-like peptide-1 (GLP-1), a derivative of GLP-1, or an analog of GLP-1.

In certain embodiments, the GLP-1 receptor agonist is GLP-1(7-36)amide shown in FIG. 1A (SEQ ID NO:1).

In another embodiment of the present invention the formulation comprises exenatide, a derivative of exenatide, or an analog of exenatide. In certain embodiments, the exenatide is the exenatide peptide shown in FIG. 1B (SEQ ID NO:2).

In certain embodiments, additional beneficial agents are provided with the GLP-1 receptor agonist formulations, such as anticancer agents, including without limitation, chemotherapeutic agents, anticancer antibodies, antisense nucleotides, siRNA, anticancer vaccines, and the like. Such additional beneficial agents are described in detail below. Administration of these agents is not limited to any particular delivery system and may include, without limitation, delivery using osmotic delivery devices as described herein if the agent is suitable for such delivery, or may be parenteral (including subcutaneous, intravenous, intramedullary, intraarticular, intramuscular, or intraperitoneal injection), rectal, topical, transdermal, intranasal, by inhalation, or oral (for example, in capsules, suspensions, or tablets). Administration of the additional agents to an individual may occur in a single dose or in repeat administrations, and in any of a variety of physiologically acceptable salt forms, and/or with an acceptable pharmaceutical carrier and/or additive as part of a pharmaceutical composition.

Physiologically acceptable salt forms and standard pharmaceutical formulation techniques and excipients are well known to persons skilled in the art (see, e.g., Physicians' Desk Reference (PDR) 2009, 63th ed. (PDR.net), Medical Economics Company; and Remington: The Science and Practice of Pharmacy, eds. Gennado et al., 21th ed, Lippincott, Williams & Wilkins, 2005). In certain embodiments, the GLP-1 receptor agonist and/or suitable additional beneficial agents, if present, are provided in a suspension formulation, comprising a particle formulation and a suspension vehicle. The particle formulation includes, but is not limited to, the GLP-1 receptor agonist or other agent of interest and one or more stabilizers. The one or more stabilizers are typically selected from the group consisting of carbohydrates, antioxidants, amino acids, and buffers. The suspension vehicle is typically a non-aqueous, single-phase suspension vehicle comprising one or more polymers and one or more solvents. The suspension vehicle exhibits viscous fluid characteristics. The particle formulation is uniformly dispersed in the vehicle.

The particle formulation of the present invention typically includes one or more of the following stabilizers: one or more carbohydrates (e.g., a disaccharide, such as, lactose, sucrose, trehalose, cellobiose, and mixtures thereof); one or more antioxidants (e.g., methionine, ascorbic acid, sodium thiosulfate, ethylenediaminetetraacetic acid (EDTA), citric acid, butylated hydroxyltoluene, and mixtures thereof); and one or more buffers (e.g., citrate, histidine, succinate, and mixtures thereof). In a preferred embodiment, the particle formulation comprises a GLP-1 receptor agonist, sucrose, methionine, and citrate buffer. The ratio of the GLP-1 receptor agonist to sucrose+methionine is typically about 1/20, about 1/10, about 1/5, about 1/2, about 2/1, about 5/1, about 10/1, or about 20/1, preferably between about 1/5 to 5/1, more preferably between about 1/3 to 3/1. The particle formulation is preferably a particle formulation prepared by spray drying and has a low moisture content, preferably less than or equal to about 10 wt %, more preferably less or equal to about 5 wt %. Alternatively, the particle formulation can be lyophilized.

The suspension vehicle for use in the present formulations comprises one or more solvents and one or more polymers. Preferably the solvent is selected from the group consisting of lauryl lactate, lauryl alcohol, benzyl benzoate, and mixtures thereof. More preferably the solvent is lauryl lactate or benzyl benzoate. Preferably the polymer is a pyrrolidone polymer. In some embodiments the polymer is polyvinylpyrrolidone (e.g., polyvinylpyrrolidone K-17, which typically has an approximate average molecular weight range of 7,900-10,800). In one embodiment, the solvent consists essentially of benzyl benzoate and polyvinylpyrrolidone.

The suspension formulation typically has a low overall moisture content, for example, less than or equal to about 10 wt % and in a preferred embodiment less than or equal to about 5 wt %.

2.1.0 Compositions and Formulations 2.1.1 GLP-1 Receptor Agonists

GLP-1, including three forms of the peptide, GLP-1(1-37), GLP-1(7-37) and GLP-1(7-36)amide, as well as peptide analogs of GLP-1 have been shown to stimulate insulin secretion (i.e., they are insulinotropic), which results in decreases in serum glucose concentrations (see, e.g., Mojsov, S., Int. J. Peptide Protein Research (1992) 40:333-343). The sequence of GLP-1(7-36)amide is shown in FIG. 1A and SEQ ID NO:1.

Numerous GLP-1 peptide derivatives and peptide analogs demonstrating insulinotropic action are known in the art (see, e.g., U.S. Pat. Nos. 5,118,666; 5,120,712; 5,512,549; 5,545,618; 5,574,008; 5,574,008; 5,614,492; 5,958,909; 6,191,102; 6,268,343; 6,329,336; 6,451,974; 6,458,924; 6,514,500; 6,593,295; 6,703,359; 6,706,689; 6,720,407; 6,821,949; 6,849,708; 6,849,714; 6,887,470; 6,887,849; 6,903,186; 7,022,674; 7,041,646; 7,084,243; 7,101,843; 7,138,486; 7,141,547; 7,144,863; and 7,199,217, all of which are incorporated herein by reference in their entireties), as well as in clinical trials (e.g., taspoglutide and albiglutide). One example of a GLP-1 peptide derivative useful in the practice of the present invention is VICTOZA™ (liraglutide; U.S. Pat. Nos. 6,268,343, 6,458,924, 7,235,627, incorporated herein by reference in their entireties). Once-daily injectable VICTOZA™ (liraglutide) is commercially available in the United States, Europe, and Japan. Other injectable GLP-1 peptides for use with the present invention are described above and include, without limitation taspoglutide, albiglutide (SYNCRIA™), LY2189265 and semaglutide. For ease of reference the family of GLP-1 peptides, GLP-1 peptide derivatives and GLP-1 peptide analogs having insulinotropic activity is referred to collectively as "GLP-1."

The molecule exenatide has the amino acid sequence of exendin-4 (Kolterman O. G., et al., J. Clin. Endocrinol. Metab. (2003) 88(7):3082-3089) and is produced by chemical synthesis or recombinant expression. Twice-daily injectable exenatide is commercially available in the United States and Europe, and sold under the tradename of BYETTA™. Another injectable exenatide under development is BYDUREON™. Exendin-3 and exendin-4 are known in the art and were originally isolated from Heloderma spp. (Eng, et al., J. Biol. Chem. (1990) 265:20259-62; Eng., et al., J. Biol. Chem. (1992) 267:7402-05). Numerous exenatide peptide derivatives and peptide analogs (including, e.g., exendin-4 agonists) are known in the art (see, e.g., U.S. Pat. Nos. 5,424,286; 6,268,343; 6,329,336; 6,506,724; 6,514,500; 6,528,486; 6,593,295; 6,703,359; 6,706,689; 6,767,887; 6,821,949; 6,849,714; 6,858,576; 6,872,700; 6,887,470; 6,887,849; 6,924,264; 6,956,026; 6,989,366; 7,022,674; 7,041,646; 7,115,569; 7,138,375; 7,141,547; 7,153,825; and 7,157,555, all of which are incorporated herein by reference in their entireties). One example of an exenatide derivative useful in the practice of the present invention is lixisenatide (see, e.g., U.S. Pat. No. 6,528,486, incorporated herein by reference in its entirety). For ease of reference herein, the family of exenatide peptides (e.g., including exendin-3, exendin-4, and exendin-4-amide), exenatide peptide derivatives, and exenatide peptide analogs is referred to collectively as "exenatide."

2.1.2 Suspension Formulations

In one aspect, the present invention utilizes particle formulations of GLP-1 receptor agonists described above that can be used to prepare suspension formulations. The GLP-1 receptor agonists for use with the present invention shall not be limited by method of synthesis or manufacture and shall include those obtained from natural sources, or synthesized or manufactured by recombinant (whether produced from cDNA or genomic DNA), synthetic, transgenic, and gene-activated methods. In preferred embodiments of the present invention, the GLP-1 receptor agonist is a GLP-1 peptide or an exendin peptide (as described above), for example, GLP-1(7-36)amide or exenatide, such as the exenatide peptide shown in FIG. 1B and SEQ ID NO:2. The present invention also includes combinations of two or more such agents, for example, GLP-1(7-36)amide and GIP.

Particle formulations are preferably chemically and physically stable for at least one month, preferably at least three months, more preferably at least six months, more preferably at least 12 months at delivery temperature. The delivery temperature is typically normal human body temperature, for example, about 37° C., or slightly higher, for example, about 40° C. Further, particle formulations are preferably chemically and physically stable for at least three months, preferably at least six months, more preferably at least 12 months, at storage temperature. Examples of storage temperatures include refrigeration temperature, for example, about 5° C., or room temperature, for example, about 25° C.

A particle formulation may be considered chemically stable if less than about 25%, preferably less than about 20%, more preferably less than about 15%, more preferably less than about 10%, and more preferably less than about 5% breakdown products of the peptide particles are formed after about three months, preferably after about six months, preferably after about 12 months at delivery temperature and after about six months, after about 12 months, and preferably after about 24 months at storage temperature.

A particle formulation may be considered physically stable if less than about 10%, preferably less than about 5%, more preferably less than about 3%, more preferably less than 1% aggregates of the peptide particles are formed after about three months, preferably after about six months, at delivery temperature and about 6 months, preferably about 12 months, at storage temperature.

To preserve protein stability, a GLP-1 receptor agonist solution is generally kept in a frozen condition and lyophilized or spray dried to a solid state. Tg (glass transition temperature) may be one factor to consider in achieving stable compositions of peptide. While not intending to be bound by any particular theory, the theory of formation of a high Tg amorphous solid to stabilize peptides, polypeptides, or proteins has been utilized in pharmaceutical industry. Generally, if an amorphous solid has a higher Tg, such as 100° C., peptide products will not have mobility when stored at room temp or even at 40° C. because the storage temperature is below the Tg. Calculations using molecular information have shown that if a glass transition temperature is above a storage temperature of 50° C. that there is zero mobility for molecules. No mobility of molecules correlates with no instability issues. Tg is also dependent on the moisture level in the product formulation. Generally, the more moisture, the lower the Tg of the composition.

Accordingly, in some aspects of the present invention, excipients with higher Tg may be included in the protein formulation to improve stability, for example, sucrose (Tg=75° C.) and trehalose (Tg=110° C.). Preferably, particle formulations are formable into particles using processes such as spray drying, lyophilization, desiccation, milling, granulation, ultrasonic drop creation, crystallization, precipitation, or other techniques available in the art for forming particles from a mixture of components. The particles are preferably substantially uniform in shape and size.

A typical spray dry process may include, for example, loading a spray solution containing a peptide, for example, GLP-1(7-36)amide or exenatide, and stabilizing excipients into a sample chamber. The sample chamber is typically maintained at a desired temperature, for example, refrigeration to room temperature. Refrigeration generally promotes stability of the protein. A solution, emulsion, or suspension is introduced to the spray dryer where the fluid is atomized into droplets. Droplets can be formed by use of a rotary atomizer, pressure nozzle, pneumatic nozzle, or sonic nozzle. The mist of droplets is immediately brought into contact with a drying gas in a drying chamber. The drying gas removes solvent from the droplets and carries the particles into a collection chamber. In spray drying, factors that can affect yield include, but are not limited to, localized charges on particles (which may promote adhesion of the particles to the spray dryer) and aerodynamics of the particles (which may make it difficult to collect the particles). In general, yield of the spray dry process depends in part on the particle formulation.

In one embodiment, the particles are sized such that they can be delivered via an implantable drug delivery device. Uniform shape and size of the particles typically helps to provide a consistent and uniform rate of release from such a delivery device; however, a particle preparation having a non-normal particle size distribution profile may also be used. For example, in a typical implantable osmotic delivery device having a delivery orifice, the size of the particles is less than about 30%, preferably is less than about 20%, more preferably is less than about than 10%, of the diameter of the delivery orifice. In an embodiment of the particle formulation for use with an osmotic delivery device, wherein the delivery orifice diameter of the implant is in a range of, for example, about 0.1 to about 0.5 mm, particle sizes may be preferably less than about 50 microns, more preferably less than about 10 microns, more preferably in a range from about 3 to about 7 microns. In one embodiment, the orifice is about 0.25 mm (250 microns) and the particle size is approximately 3-5 microns.

In a preferred embodiment, when the particles are incorporated in a suspension vehicle they do not settle in less than about three months at delivery temperature. Generally speaking, smaller particles tend to have a lower settling rate in viscous suspension vehicles than larger particles. Accordingly, micron- to nano-sized particles are typically desirable. In an embodiment of the particle formulation for use in an implantable osmotic delivery device, wherein the delivery orifice diameter of the implant is in a range of, for example, about 0.1 to about 0.5 mm, particle sizes may be preferably less than about 50 microns, more preferably less than about 10 microns, more preferably in a range from about 3 to about 7 microns.

In one embodiment, a particle formulation for use with the present invention comprises one or more GLP-1 receptor agonists, as described above and one or more stabilizers. The stabilizers may be, for example, carbohydrate, antioxidant, amino acid, buffer, or inorganic compound. The amounts of stabilizers in the particle formulation can be determined experimentally based on the activities of the stabilizers and buffers and the desired characteristics of the formulation. Typically, the amount of carbohydrate in the formulation is determined by aggregation concerns. In general, the carbohydrate level should not be too high so as to avoid promoting crystal growth in the presence of water due to excess carbohydrate unbound to insulinotropic peptide. Typically, the amount of antioxidant in the formulation is determined by oxidation concerns, while the amount of amino acid in the formulation is determined by oxidation concerns and/or formability of particles during spray drying. Typically, the amount of buffer components in the formulation is determined by pre-processing concerns, stability concerns, and formability of particles during spray drying. Buffer may be required to stabilize the GLP-1 receptor agonist during processing, e.g., solution preparation and spray drying, when all excipients are solubilized.

Examples of carbohydrates that may be included in the particle formulation include, but are not limited to, monosaccharides (e.g., fructose, maltose, galactose, glucose, D-mannose, and sorbose), disaccharides (e.g., lactose, sucrose, trehalose, and cellobiose), polysaccharides (e.g., raffinose, melezitose, maltodextrins, dextrans, and starches), and alditols (acyclic polyols; e.g., mannitol, xylitol, maltitol, lactitol, xylitol sorbitol, pyranosyl sorbitol, and myoinsitol). Preferred carbohydrates include non-reducing sugars, such as sucrose, trehalose, and raffinose.

Examples of antioxidants that may be included in the particle formulation include, but are not limited to, methionine, ascorbic acid, sodium thiosulfate, catalase, platinum, ethylenediaminetetraacetic acid (EDTA), citric acid, cysteins, thioglycerol, thioglycolic acid, thiosorbitol, butylated hydroxanisol, butylated hydroxyltoluene, and propyl gallate.

Examples of amino acids that may be included in the particle formulation include, but are not limited to, arginine, methionine, glycine, histidine, alanine, L-leucine, glutamic acid, iso-leucine, L-threonine, 2-phenylamine, valine, norvaline, praline, phenylalanine, trytophan, serine, asparagines, cysteine, tyrosine, lysine, and norleucine. Preferred amino acids include those that readily oxidize, e.g., cysteine, methionine, and trytophan.

Examples of buffers that may be included in the particle formulation include, but are not limited to, citrate, histidine, succinate, phosphate, maleate, tris, acetate, carbohydrate, and gly-gly. Preferred buffers include citrate, histidine, succinate, and tris. It is to be understood that buffers can be added to the solution before formation of the particles, for example, by spray drying. However, after the dry particle formation is prepared, the buffer component no longer serves as a buffer in the dried particles. For ease of reference herein, when referring to buffer components, the term buffer is used.

Examples of inorganic compounds that may be included in the particle formulation include, but are not limited to, NaCl, $Na_2SO_4$, $NaHCO_3$, KCl, $KH_2PO_4$, $CaCl_2$, and $MgCl_2$.

In addition, the particle formulation may include other excipients, such as but not limited to surfactants and salts. Examples of surfactants include, but are not limited to, Polysorbate 20, Polysorbate 80, PLURONIC™, F68, and sodium docecyl sulfate (SDS). Examples of other excipients include, but are not limited to, mannitol and glycine. Examples of salts include, but are not limited to, sodium chloride, calcium chloride, and magnesium chloride.

In one embodiment, the particle formulation comprises, for example, exenatide peptide, sucrose (carbohydrate), methionine (antioxidant), and sodium citrate/citric acid.

All components included in the particle formulation are typically acceptable for pharmaceutical use in mammals, in particular, in humans.

Particle size distribution of the dry particle powder can be well controlled (0.1 micron-20 micron), for example, by using the methods of spray drying or lyophilization to prepare the particle formulations. The process parameters for formation of the dry powder are optimal to produce particles with desired particle size distribution, density, and surface area.

The selected excipients and stabilizers in the particle formulation may provide, for example, the following functions: density modification of the dry powder; preservation of the peptide chemical stability; maintenance of the peptide's physical stability (e.g., high glass transition temperature, and avoiding phase to phase transition); producing homogenous dispersions in suspension; and modification of hydrophobicity and/or hydrophilicity to manipulate dry powder solubility in selected solvents.

See U.S. Patent Publication No. 2008/0260840, incorporated herein by reference in its entirety, for detailed methods of producing particle formulations.

In summary, GLP-1 receptor agonists can be formulated into dried powders in solid state, which preserves maximum chemical and biological stability of proteins or peptides. The particle formulation offers long term storage stability at high temperature, and therefore, allows delivery to a subject of stable and biologically effective peptide for extended periods of time.

Although the particle formulations described above are with reference to GLP-1 receptor agonists, such particle formulations can also be formed with any other suitable agents, such as other suitable beneficial polypeptides, including suitable anticancer polypeptides, antibodies and the like, described in detail below.

Suspension formulations for use with the present invention can be produced using particle formulations as described above. See U.S. Patent Publication No. 2008/0260840, incorporated herein by reference in its entirety, for detailed methods of producing such suspension formulations. In one aspect of the present invention, the suspension formulation includes a suspension vehicle to provide a stable environment in which the GLP-1 receptor agonist particle formulation (or other suitable particle formulation) is dispersed. The particle formulations are chemically and physically stable (as described above) in the suspension vehicle. The suspension vehicle typically comprises one or more polymers and one or more solvents that form a solution of sufficient viscosity to uniformly suspend the particles comprising the GLP-1 receptor agonist or other suitable agent. In addition to the GLP-1 receptor agonist, the suspension formulations can be used with any suitable agents, such as other suitable beneficial polypeptides, including suitable anticancer polypeptides, antibodies and the like, described in detail below.

The viscosity of the suspension vehicle is typically sufficient to prevent the particle formulation from settling during storage and use in a method of delivery, for example, in an implantable, drug delivery device. The suspension vehicle is biodegradable in that the suspension vehicle disintegrates or breaks down over a period of time in response to a biological environment. The disintegration of the suspension vehicle may occur by one or more physical or chemical degradative processes, such as by enzymatic action, oxidation, reduction, hydrolysis (e.g., proteolysis), displacement (e.g., ion exchange), or dissolution by solubilization, emulsion or micelle formation. After the suspension vehicle disintegrates, components of the suspension vehicle are absorbed or otherwise dissipated by the body and surrounding tissue of the patient.

The solvent in which the polymer is dissolved may affect characteristics of the suspension formulation, such as the behavior of the particle formulation during storage. A solvent may be selected in combination with a polymer so that the resulting suspension vehicle exhibits phase separation upon contact with the aqueous environment. In some embodiments, the solvent may be selected in combination with the polymer so that the resulting suspension vehicle exhibits phase separation upon contact with the aqueous environment having less than approximately about 10% water.

The solvent may be an acceptable solvent that is not miscible with water. The solvent may also be selected so that the polymer is soluble in the solvent at high concentrations, such as at a polymer concentration of greater than about 30%. However, typically particles comprising the GLP-1 receptor agonists are substantially insoluble in the solvent. Examples of solvents useful in the practice of the present invention include, but are not limited to, lauryl alcohol, benzyl benzoate, benzyl alcohol, lauryl lactate, decanol (also called decyl alcohol), ethyl hexyl lactate, and long chain ($C_8$ to $C_{24}$) aliphatic alcohols, esters, or mixtures thereof. The solvent used in the suspension vehicle may be "dry," in that it has a low moisture content. Preferred solvents for use in formulation of the suspension vehicle include lauryl lactate, lauryl alcohol, benzyl benzoate, and combinations thereof.

Examples of polymers for formulation of the suspension vehicles include, but are not limited to, a polyester (e.g., polylactic acid or polylacticpolyglycolic acid), pyrrolidone polymer (e.g., polyvinylpyrrolidone (PVP) having a molecular weight ranging from approximately 2,000 to approximately 1,000,000), ester or ether of an unsaturated alcohol (e.g., vinyl acetate), polyoxyethylenepolyoxypropylene block copolymer, or mixtures thereof. In one embodiment, the polymer is PVP having a molecular weight of 2,000 to 1,000,000. In a preferred embodiment the polymer is polyvinylpyrrolidone K-17 (typically having an approximate average molecular weight range of 7,900-10,800). Polyvinylpyrrolidone can be characterized by its K-value (e.g., K-17), which is a viscosity index. The polymer used in the suspension vehicle may include one or more different polymers or may include different grades of a single polymer. The polymer used in the suspension vehicle may also be dry or have a low moisture content.

Generally speaking, a suspension vehicle according to the present invention may vary in composition based on the desired performance characteristics. In one embodiment, the suspension vehicle may comprise about 40% to about 80% (w/w) polymer(s) and about 20% to about 60% (w/w) solvent(s). Preferred embodiments of a suspension vehicle include vehicles formed of polymer(s) and solvent(s) combined at the following ratios: about 25% solvent and about 75% polymer; about 50% solvent and about 50% polymer; about 75% solvent and about 25% polymer.

The suspension vehicle may exhibit Newtonian behavior. The suspension vehicle is typically formulated to provide a viscosity that maintains a uniform dispersion of the particle formulation for a predetermined period of time. This helps facilitate making a suspension formulation tailored to provide controlled delivery of the insulinotropic peptide at a desired rate. The viscosity of the suspension vehicle may vary depending on the desired application, the size and type of the particle formulation, and the loading of the particle formulation in the suspension vehicle. The viscosity of the suspension vehicle may be varied by altering the type or relative amount of the solvent or polymer used.

The suspension vehicle may have a viscosity ranging from about 100 poise to about 1,000,000 poise, preferably from about 1,000 poise to about 100,000 poise. The viscosity may be measured at a selected temperature, for example, 33° C., at a shear rate of 10.sup.−4/sec, using a parallel plate rheometer. In some embodiments, the viscosity of the suspension vehicle ranges from approximately 5,000 poise to approximately 50,000 poise, such as about 7,000 poise to about 40,000 poise, about 8,000 poise to about 20,000 poise, about 9,000 poise to about 25,000 poise, about 10,000 poise to about 20,000 poise, and the like. In preferred embodiments, the viscosity range is between about 12,000 to about 18,000 poise at 33° C.

The suspension vehicle may exhibit phase separation when contacted with the aqueous environment; however, typically the suspension vehicle exhibits substantially no phase separation as a function of temperature. For example, at a temperature ranging from approximately 0° C. to approximately 70° C. and upon temperature cycling, such as cycling from 4° C. to 37° C. to 4° C., the suspension vehicle typically exhibits no phase separation.

The suspension vehicle may be prepared by combining the polymer and the solvent under dry conditions, such as in a dry box. The polymer and solvent may be combined at an elevated temperature, such as from approximately 40° C. to approximately 70° C., and allowed to liquefy and form the single phase. The ingredients may be blended under vacuum to remove air bubbles produced from the dry ingredients. The ingredients may be combined using a conventional mixer, such as a dual helix blade or similar mixer, set at a speed of approximately 40 rpm. However, higher speeds may also be used to mix the ingredients. Once a liquid solution of the ingredients is achieved, the suspension vehicle may be cooled to room temperature. Differential scanning calorimetry (DSC) may be used to verify that the suspension vehicle is a single phase. Further, the components of the vehicle (e.g., the solvent and/or the polymer) may be treated to substantially reduce or substantially remove peroxides (e.g., by treatment with methionine; see, e.g., U.S. Patent Application Publication No. 2007-0027105, incorporated herein by reference in its entirety).

The particle formulation, comprising a GLP-1 receptor agonist, or other suitable agent, is added to the suspension vehicle to form a suspension formulation. The suspension formulation may be prepared by dispersing the particle formulation in the suspension vehicle. The suspension vehicle may be heated and the particle formulation added to the suspension vehicle under dry conditions. The ingredients may be mixed under vacuum at an elevated temperature, such as from about 40° C. to about 70° C. The ingredients may be mixed at a sufficient speed, such as from about 40 rpm to about 120 rpm, and for a sufficient amount of time, such as about 15 minutes, to achieve a uniform dispersion of the particle formulation in the suspension vehicle. The mixer may be a dual helix blade or other suitable mixer. The resulting mixture may be removed from the mixer, sealed in a dry container to prevent water from contaminating the suspension formulation, and allowed to cool to room temperature before further use, for example, loading into an implantable, drug delivery device, unit dose container, or multiple-dose container.

The suspension formulation typically has an overall moisture content of less than about 10 wt %, preferably less than about 5 wt %, and more preferably less than about 4 wt %.

The suspension formulations of the present invention are exemplified herein below with reference to exenatide and GLP-1(7-36)amide as representative GLP-1 receptor agonists (see, Example 3 and Example 4). These examples are not intended to be limiting.

In summary, the components of the suspension vehicle provide biocompatibility. Components of the suspension vehicle offer suitable chemico-physical properties to form stable suspensions of, for example, dry powder particle formulations. These properties include, but are not limited to, the following: viscosity of the suspension; purity of the vehicle; residual moisture of the vehicle; density of the vehicle; compatibility with the dry powders; compatibility with implantable devices; molecular weight of the polymer; stability of the vehicle; and hydrophobicity and hydrophilicity of the vehicle. These properties can be manipulated and controlled, for example, by variation of the vehicle composition and manipulation of the ratio of components used in the suspension vehicle.

3.0.0 Delivery of Suspension Formulations

The suspension formulations described herein may be used in an implantable, drug delivery device to provide sustained delivery of a compound over an extended period of time, such as over weeks, months, or up to about one year. Such an implantable drug delivery device is typically capable of delivering the compound at a desired flow rate over a desired period of time. The suspension formulation may be loaded into the implantable, drug delivery device by conventional techniques.

The suspension formulation may be delivered, for example, using an osmotically, mechanically, electromechanically, or chemically driven drug delivery device. The active agent in the suspension formulation is delivered at a flow rate that is therapeutically effective to the subject in need of treatment.

The active agent, such as GLP-1(7-36)amide, exenatide, or other suitable beneficial agent, may be delivered over a period ranging from more than about one week to about one year or more, preferably for about one month to about a year or more, more preferably for about three months to about a year or more. The implantable, drug delivery device may include a reservoir having at least one orifice through which the agent is delivered. The suspension formulation may be stored within the reservoir. In one embodiment, the implantable, drug delivery device is an osmotic delivery device, wherein delivery of the drug is osmotically driven. Some osmotic delivery devices and their component parts have been described, for example, the DUROS™ delivery device or similar devices (see, e.g., U.S. Pat. Nos. 5,609,885; 5,728,396; 5,985,305; 5,997,527; 6,113,938; 6,132,420; 6,156,331; 6,217,906; 6,261,584; 6,270.787; 6,287,295; 6,375,978; 6,395,292; 6,508,808; 6,544,252; 6,635,268; 6,682,522; 6,923,800; 6,939,556; 6,976,981; 6,997,922; 7,014,636; 7,207,982; 7,112,335; 7,163,688; U.S. Patent Publication Nos. 2005-0175701, 2007-0281024, and 2008-0091176, all of which are incorporated herein by reference in their entireties).

The DUROS™ delivery device typically consists of a cylindrical reservoir which contains the osmotic engine, piston, and drug formulation. The reservoir is capped at one end by a controlled-rate water-permeable membrane and capped at the other end by a diffusion moderator through which drug formulation is released from the drug reservoir. The piston separates the drug formulation from the osmotic engine and utilizes a seal to prevent the water in the osmotic engine compartment from entering the drug reservoir. The diffusion moderator is designed, in conjunction with the drug formulation, to prevent body fluid from entering the drug reservoir through the orifice.

The DUROS™ device releases a therapeutic agent at a predetermined rate based on the principle of osmosis. Extracellular fluid enters the DUROS™ device through a semipermeable membrane directly into a salt engine that expands to drive the piston at a slow and even delivery rate. Movement of the piston forces the drug formulation to be released through the orifice or exit port at a predetermined sheer rate. In one embodiment, the reservoir of the DUROS™ device is loaded with a suspension formulation comprising, for example, GLP-1(7-36)amide or exenatide, wherein the device is capable of delivering the suspension formulation to a subject over an extended period of time (e.g., about one, about two, about three, about six, or about 12 months) at a predetermined, therapeutically effective delivery rate.

Other implantable, drug delivery devices may be used in the practice of the present invention and may include regulator-type implantable pumps that provide constant flow, adjustable flow, or programmable flow of the compound, such as those available from Codman & Shurtleff, Inc. (Raynham, Mass.), Medtronic, Inc. (Minneapolis, Minn.), and Tricumed Medinzintechnik GmbH (Germany).

Implantable devices, for example, the DUROS™ device, provide the following advantages for administration of the formulations of the present invention: true zero-order release of the insulinotropic peptide pharmacokinetically; long-term release period time (e.g., up to about 12 months); and reliable delivery and dosing of the GLP-1 receptor agonist or other suitable beneficial agent.

FIG. 2 depicts a representative osmotic delivery device useful in the practice of the present invention. In FIG. 2, an osmotic delivery device 10 is shown comprising a reservoir 12. A piston assembly 14 is positioned in the lumen of the reservoir and divides the lumen into two chambers. In this example, the chamber 16 contains a beneficial agent formulation, such as a GLP-1 receptor agonist (e.g., GLP-1 (7-36)amide or exenatide) formulation, an anticancer agent, or the like and the chamber 20 contains an osmotic agent formulation. A semi-permeable membrane 18 is positioned at a distal end of the reservoir, adjacent the chamber 20 containing the osmotic agent formulation. A diffusion moderator 22 is positioned in mating relationship at a distal end of the reservoir 12, adjacent the chamber 16 containing the beneficial agent formulation. The diffusion moderator 22 includes a delivery orifice 24. The diffusion moderator 22 may be any suitable flow device having a delivery orifice. In this embodiment, the flow path 26 is formed between a threaded diffusion moderator 22 and threads 28 formed on the interior surface of the reservoir 12. In alternative embodiments, the diffusion moderator can, for example, (i) be press-fit (or friction fit) through an opening and contacting a smooth interior surface of the reservoir, or (ii) comprise two pieces with an outer shell constructed and arranged for positioning in an opening, an inner core inserted in the outer shell, and a fluid channel having a spiral shape defined between the outer shell and the inner core (e.g., U.S. Patent Publication No. 2007-0281024, incorporated herein by reference in its entirety).

Fluid is imbibed into the chamber 20 through the semipermeable membrane 18. The beneficial agent formulation is dispensed from the chamber 16 through the delivery orifice 24 in the diffusion moderator 22. The piston assembly 14 engages and seals against the interior wall of the reservoir 12, thereby isolating the osmotic agent formulation in chamber 20 and fluid imbibed through the semi-permeable membrane 18 from the beneficial agent formulation in chamber 16. At steady-state, the beneficial agent formulation is expelled through the delivery orifice 24 in the diffusion moderator 22 at a rate corresponding to the rate at which external fluid is imbibed into the chamber 20 through the semi-permeable membrane 18.

The semi-permeable membrane 18 may be in the form of a plug that is resiliently engaged in sealing relationship with the interior surface of the reservoir 12. In FIG. 2, it is shown to have ridges that serve to frictionally engage the semi-permeable membrane 18 with the interior surface of the reservoir 12.

The amount of beneficial agent employed in the delivery device of the invention is that amount necessary to deliver a therapeutically effective amount of the agent to achieve the desired therapeutic result. In practice, this will vary depending upon such variables, for example, as the particular agent, the site of delivery, the severity of the condition, and the desired therapeutic effect. Typically, for an osmotic delivery device, the volume of a beneficial agent chamber comprising the beneficial agent formulation is between about 100 µl to about 1000 µl, more preferably between about 120 µl and about 500 µl, more preferably between about 150 µl and about 200 µl.

Typically, the osmotic delivery device is implanted within the subject, for example, subcutaneously. The device(s) can be inserted in either or both arms (e.g., in the inside, outside, or back of the upper arm) or into the abdomen. Preferred locations in the abdomen are under the abdominal skin in the area extending below the ribs and above the belt line. To provide a number of locations for insertion of one or more osmotic delivery devices within the abdomen, the abdominal wall can be divided into 4 quadrants as follows: the upper right quadrant extending 5-8 centimeters below the right ribs and about 5-8 centimeters to the right of the midline, the lower right quadrant extending 5-8 centimeters above the belt line and 5-8 centimeters to the right of the midline, the upper left quadrant extending 5-8 centimeters below the left ribs and about 5-8 centimeters to the left of the midline, and the lower left quadrant extending 5-8 centimeters above the belt line and 5-8 centimeters to the left of the midline. This provides multiple available locations for implantation of one or more devices on one or more occasions.

The suspension formulation may also be delivered from a drug delivery device that is not implantable or implanted, for example, an external pump such as a peristaltic pump used for subcutaneous delivery in a hospital setting.

The suspension formulations of the present invention may also be used in infusion pumps, for example, the ALZET™ osmotic pumps which are miniature, infusion pumps for the continuous dosing of laboratory animals (e.g., mice and rats).

The suspension formulations of the present invention may also be used in the form of injections to provide highly concentrated bolus doses of biologically active agents, such as the GLP-1 receptor agonists, anti-cancer agents, etc.

4.0.0 Anticancer Agents

The GLP-1 receptor agonists, such as GLP-1(7-36)amide and exenatide, can be delivered to a patient as a single modality treatment or in combination with other beneficial agents, including anticancer agents as described below, chemotherapeutic drugs, anticancer antibodies, antisense molecules, siRNA, and the like.

For example, one useful combination is with a tyrosine kinase inhibitor, such as SUTENT™, NEXAVAR™, BIBF 1120, ZD1839 (gefitinib), erlotinib, TYKERB™, and the like.

mTOR inhibitors, such as rapamycin (sirolimus), AZD8055, NVP-BEZ235, deforolimus, everolimus, temsirolimus, GSK1059615, WYE354, KU0063794, XL765 (all available from Selleck Chemicals) will also find use in a combination treatment.

Other drugs for use in combination with the GLP-1 receptor agonists (e.g., exenatide and GLP-1(7-36)amide), are those that cause hypoxia in tumor tissues, such as metformin, and drugs that inhibit the hypoxia inducible factor 1 such as CCAA/enhancer binding protein a, PX-478, resveratrol, and the various small molecule inhibitors described in Jones et al., Mol. Cancer. Ther. (2006) 5:2193-2202.

Also useful are drugs that inhibit IGF-1, such as octreonide acetate and tyrosine kinase inhibitors, that serve to block IGF-1 receptor signaling.

VEGF-inhibitors, such as anti-VEGF antibodies including bevacizumab) (AVASTIN™, as well as prolactin, sunitinib and sorafenib, may also be used in combination with the GLP-1 receptor agonists.

Another useful combination therapy is the use of a sugar analog, such as 2DG, subsequent to reducing glucose availability to the cancer cells using GLP-1 receptor agonists, such as exenatide and GLP-1(7-36)amide.

Cell cycle blockers will also find use herein, such as a cyclin-dependent kinase (cdk)-inhibitor, e.g., olomoucin, butyrolactone-I, n-butyrate, upregulators of cdk activity, e.g., flavopiridol, Chalcones (1,3-diphenylpropen-1-ones) and derivatives thereof.

The histone deacetylase (HDAC) enzyme SIRT-1 and other related sirtuin proteins, analogs and derivatives thereof will also find use herein.

Also useful are peptides that induce cell apoptosis, such TRAIL, antagonists or antibodies against integrin $\alpha_v$-$\beta_3$, anti-survivin antibodies and antagonists of survivin, and numerous pro-apoptotic peptides, well known in the art, such as described in Ellerby et al., Nat. Med. (1999) 5:1032-1038.

Examples of cytokines which can be administered in a combination treatment include G-CSF, GM-CSF, M-CSF, IL-1.alpha., IL-1.beta., IL-2, IL-3, IL-4, IL-5, IL-6, IL-7, IL-8, IL-10, IL-12, IL-18, IL-21, IL-23, IFN-.alpha., IFN-.beta., IFN-.gamma., IFN-.lamda., MIP-1.alpha., MIP-1.beta., TGF-.beta., TNF.alpha., and TNF-.beta.

Examples of chemokines which can be administered include BCA-1/BLC, BRAK, Chemokine CC-2, CTACK, CXCL-16, ELC, ENA, ENA-70, ENA-74, ENA-78, Eotaxin, Exodus-2, Fractalkine, GCP-2, GRO, GRO alpha (MGSA), GRO-beta, GRO-gamma, HCC-1, HCC-4, 1-309, IP-10, 1-TAC, LAG-1, LD78-beta, LEC/NCC-4, LL-37, Lymphotactin, MCP, MCAF (MCP-1), MCP-2, MCP-3, MCP-4, MDC, MDC, MDC-2, MDC-4, MEC/CCL28, MIG, MIP, MIP-1 alpha, MIP-1 beta, MIP-1 delta, MIP-3/MPIF-1, MIP-3 alpha, MIP-3 bet, MIP-4 (PARC), MIP-5, NAP-2, PARC PF-4, RANTES, RANTES-2, SDF-1 alpha, SDF-1 beta, TARC, and TECK.

Examples of growth factors which can be delivered include Human Amphiregulin, Human Angiogenesis Proteins, Human ACE, Human Angiogenin, Human Angiopoietin, Human Angiostatin, Human Endostatin, Human Betacellulin, Human BMP, Human BMP-13/CDMP-2, Human BMP-14/CDMP-1, Human BMP-2, Human BMP-3, Human BMP-4, Human BMP-5, Human BMP-6, Human BMP-7, Human BMP-8, Human BMP-9, Human Colony Stimulating Factors, Human flt3-Ligand, Human G-CSF, Human GM-CSF, Human M-CSF, Human Connective Tissue Growth Factor, Human Cripto-1, Human Cryptic, Human ECGF, Human EGF, Human EG-VEGF, Human Erythropoietin, Human Fetuin, Human FGF, Human FGF-1, Human FGF-10, Human FGF-16, Human FGF-17, Human FGF-18, Human FGF-19, Human FGF-2, Human FGF-20, Human FGF-3, Human FGF-4, Human FGF-5, Human FGF-6, Human FGF-7/KGF, Human FGF-8, Human FGF-9, Human FGF-acidic, Human FGF-basic, Human GDF-11, Human GDF-15, Human Growth Hormone Releasing Factor, Human HB-EGF, Human Heregulin, Human HGF, Human IGF, Human IGF-1, Human IGF-11, Human Inhibin, Human KGF, Human LCGF, Human LIF, Human Miscellaneous Growth Factors, Human MSP, Human Myostatin, Human Myostatin Propeptide, Human Nerve Growth Factor, Human Oncostatin M, Human PD-ECGF, Human PDGF, Human PDGF (AA Homodimer), Human PDGF (AB Heterodimer), Human PDGF (BB Homodimer), Human PDGF (CC Homodimer), Human PLGF, Human PLGF-1, Human PLGF-2, Human SCF, Human SMDF, Human Stem Cell Growth Factor, Human SCGF-alpha, Human SCGF-beta, Human Thrombopoietin, Human Transforming Growth Factor, Human TGF-alpha, and Human TGF-beta.

In some embodiments, chemotherapeutic agents used in the methods of the invention are selected from antimetabolites; enzyme inhibitors including topoisomerase I and II inhibitors, tyrosine and serine/threonine kinase inhibitors and COX2 inhibitors, tubulin binders, proteasome inhibitors, anticancer alkylating agents including bifunctional and monofunctional alkylating agents and methylating agents, anticancer antibiotics, anticancer antibodies and active fragments and fusions thereof and antibody-drug conjugates, bisphosphonates, antiestrogens and antiandrogens, anticancer cytokines, anticancer enzymes, immunomodulatory agents, anticancer peptides, anticancer retinoids, anticancer steroids and related agents, anticancer phototherapeutics, normal tissue protectors and antihormonal agents including aromatase inhibitors.

Antimetabolites may include folate analogs, which inhibit dihydrofolate reductase resulting in DNA breaks by blocking purine and thymidylate synthesis. Examples of folate analogs include methotrexate (FOLEX™), trimetrexate (NEUTREXIN™) and pemetrexed (ALIMTA™). Other anitmetabolites are nucleoside analogs that disrupt DNA or RNA synthesis, such as purine or pyrimidine analogs. Examples of purine analogs include allopurinol (ZYLOPRIM™), mercaptopurine (PURINETHOL™), fludarabine (FLUDARA™), thioguanine (6-TG), cladribine (LEUSTATIN™, 2-CdA), and pentostatin (NIPENT™). Examples of pyrimidine analogs include capecitabine (XELODA™), cytarabine (CYTOSAR™), liposomal cytarabine (DEPOCYT™), floxuridine (FUDR™), fluororouracil (ADRUCIL™), gemcitabine (GEMZAR™), and clofarabine (CLOLAR™), decitabine (DACOGEN™) and azacitadine (VIDAZA™).

Topoisomerase II inhibitors bind to topoisomerase II and DNA, preventing the resealing of DNA strands during replication, and leading to DNA strand breaks, such as epipodophyllotoxins. Examples of epipodophyllotoxins include etoposide (VEPESID™, ETOPOPHOS™) and teniposide (VUMON™, VM26™). Alternatively, topoisomerase II inhibitors, such as anthracycline antibiotics, intercalate between DNA base pairs leading to free radicals and also topoisomerase II inhibition. Examples of anthracyclines include daunorubicin (DANOIJXOME™, CERUBIDINE™), liposomal daunorubicin (DAUNOXOME™), doxorubicin (ADRIAMYCIN™, RUBEX™), liposomal doxorubicin (DOXIL™), epirubicin (ELLENCE™), valrubicin (VALSTAR™), and idarubicin (IDAMYCIN™). Mitoxantrone (NOVANTRONE™) also inhibits topoisomerase II and is an anticancer therapeutic.

Topoisomerase I inhibitors bind to topoisomerase I and DNA, preventing DNA strand breaks, such as, e.g., camptothecins, including irinotecan (CAMPTOSAR™) and topotecan (HYCAMTIN™).

Anticancer kinase inhibitors inhibit phosphorylation of a protein or small molecule messenger in a an intracellular signaling pathway in malignant cells or vascular or stromal cells, such as, e.g., imatinib mseylate (GLEEVEC™), gefitinib (IRESSA™) or erlotinib (TARCEVA™), sorafenib (NEXAVAR™), sunitinib (SUTENT™), nilotinib (TASIGN™), everolimus (AFINITOR™), lapatinib (TYKERB™), dasatinib (SPRYCEL™), BRAF inhibitors such as GSK218436 (GlaxoSmithKline, London UK) and vemurafenib (Plexxikon Inc., CA) and MEK inhibitors.

Tubulin binders include agents that bind to microtubules, shift the microtubules toward polymerization, and are active in the M phase, such as taxanes including docetaxel (TAXOTERE™) and paclitaxel (TAXOL™) and epothilones including ixabepilone (IXEMPRA™) and eribulin mesylate. Other tubulin binders act by inhibiting polymerization and mitotic spindle formation, and are active in the S phase, such as, e.g., vinca alkaloids, including vinblastine (VELBAN™), vincristine (ONCOVIN™), and vinorelbine (NAVELBINE™). Other tubulin binders include ILX-651 (TASIDOTIN™) and estramustine (EMCYT™), which inhibit microtubule assembly and disassembly.

Proteasome inhibitors block the trypsin-like, chymotrypsin-like and/or peptidylglutamyl peptide hydrolyzing-like protease activities in nuclear and cytoplasmic proteasomes. Examples of proteasome inhibitors include bortezomib (VELCADE™).

Anticancer alkylating agents are reactive molecules that bind to DNA and interfere with DNA replication. These agents include, but are not limited to, alkyl sulfonates such as busulfan (MYLERAN™), platinum analogs such as carboplatin (PARAPLATIN™), cisplatin (PLATINOL™-AQ, and oxaliplatin (ELOXATIN™), nitrosoureas such as carmustine (BICNU™), lomustine (CCNU™, CEENU™), and streptozocin (ZANOSAle), nitrogen mustards including chlorambucil (LEUKERAN™), uracil mustard, cyclophosphamide (CYTOXAN™), ifosfamide (IFEX™), meclorethamine (MUSTARGEN™), and melphalan (ALKERAN™, L-PAM), bendamustine (TREANDA™), triazenes such as dacarbazine (DTIC-DOME™), procarbazine (MATULANE™), temozolomide (TEMODAR™), ethylenimines including hexamethylamine (HEXALEN™), and thiotepa (THIOPLEX™), hydroxyurea (HYDREA™, arsenic trioxide (TRISENOX™), mitomycin C (MUTAMYCIN™, MITOZYTREX™) and trabectedin (YONDELIS™).

Anticancer antibiotics act by a variety of mechanisms including inhibition of protein synthesis generation of oxygen free radicals in the vicinity of DNA and other mechanisms. Examples of anticancer antibiotics include actinomycin D (COSMEGEN™), bleomycin sulfate (BLENOXANE™) and plicamycin (MITHRACIN™).

Anticancer antibodies bind to specific molecular targets on cells or in the extracellular space. Anticancer antibodies act by neutralizing the activity of the target, attracting immune cells to the target cell or by being directly or indirectly cytotoxic toward the target cell. Anticancer antibodies include, but are not limited to, anti-CD52 antibodies such as alemtuzumab (CAMPATH™); anti-VEGF antibodies including bevacizumab (AVASTIN™); anti-CD33 antibodies, including gemtuzumab ozogamicin (MYLOTARG™); anti-CD20 antibodies including ibritumomab (ZEVALIN™), rituximab (RITUXAN™), tositumomab (BEXXAR™) and ofatumumab (ARZERRA™); anti-EGFR antibodies such as cetuximab (ERBITUX™) and panitumumab (VECTIBEX™); anti-Her2 antibodies, including trastuzumab (HERCEPTIN™); anti-CTLA4 antibodies including Ipilimumab (YERVOY™); adnectins; and domain antibodies. Active fragments and fusions of these antibodies will also find use herein.

Anticancer cytokines include, but are not limited to, aldesleukin (PROLEUKIN™), denileukin diftitox (ONTAK™), GM-CSF (sargramostim, PROKINE™, LEUKINE™), interferon alfa-2b (INTRON™-A), PEGinterferon alpha (PEGASYS™ or PEGINTRON™) and consensus interferon (INFERGEN™).

Immunomodulatory agents are effective by increasing the response of the immune system of the host to the malignancy. Immunomodulatory agents include, but are not limited to, *Bacillus* Calmette-Gurerin (BCG Vaccine), levamisole (ERGAMISOL™), thalidomide (THALIDOMID™), sipuleucel-T (PROVENGE™), and lenalidomide (REVLIMID™).

Anticancer retinoids include, but are not limited to, aliretinoin (PANRETIN™), bexarotene (TARGRETIN™) and tretinoin (VESANOID™, ATRA™); other agents include octreotide acetate (SANDOSTATIN™).

Anticancer enzymes include asparaginase (ELSPAR™), pegademase (ADAGEN™), and pegaspargase (ONCASPAR™).

Anticancer steroids and related agents include dexamethasone (DECADRON™), predisone (DELTASONE™), prednisolone (DELTA-CORTEF™) and mitotane (LYSODREN™).

Normal tissue protectors include, but are not limited to, amifostine (ETHYOL™), darbepoetin alfa (ARANESP™), dexrazoxane (ZINECARD™), epoetin alfa (EPOGEN™, PROCRIT™), filgrastim (NEUPOGEN™), folinic acid (leucovorin), allopurinol (ALOPRIM™) mesna (MESNEX™), oprelvekin (NEUMEGA™), pegfilgrastim (NEULASTA™), GM-CSF (sargramostim, PROKINE™, LEUKINE™), raloxifene (EVISTA™) and eltrombopag (PROMACTA™).

Phototherapeutics are agents that sensitize cells so that exposure to a specific frequency of laser light induces abundant free radical formation and DNA alkylation. These agents include, but are not limited to, porfimer sodium (PHOTOFRIN™).

Antihormones include LHRH agonists, which compete with gonadotropin by binding to the hypothalamus causing an initial surge of LH and FSH followed by down regulation by negative feedback, including goserelin (ZOLADEX™), leuprolide (LUPRON™ or ELIGARD™), and triptorelin (TRELSTAR™); and antiandrogens, which competitively bind and inhibit the binding of androgens to androgen receptors, such as hicalutamide (CASODEX™), flutamide (EULEXIN™), nilutamide (NILANDRON™), aminoglutethimide (CYTADREN™), and abarelix (PLENAXIS™); and antiestrogens, which competitively bind and inhibit the binding of estrogens to estrogen receptors such as tamoxifen (NOLVADEX™), fluoxymesterone (HALOTESTIN™) and megestrol (MEGACE™), bisphosphonates including pamidronate (AREDIA™) and zoledronate (ZOMETA™), and aromatase inhibitors including anastrozole (ARIMIDEX™), exemestane (AROMASIN™), fulvestrant (FASLODEX™), and letrozole (FEMARA™), androgen biosynthesis inhibitors such as abiraterone acetate (ZITIGA™), androgen signaling inhibitor such as MDV 3100.

ATP-competitive inhibitors of c-Met/HGF receptor and/or the nucleophosmin-anaplastic lymphoma kinase (NPM-ALK) include crizotinib, CH5424802 (Chugai Pharmaceutical Co., Ltd., Japan), and AP26113 (ARIAD Pharmaceuticals, Inc., MA).

Exemplary agents including beneficial agents and anticancer agents that can be delivered with the GLP-1 receptor agonist compositions described herein include those described above and/or shown in Table 1.

TABLE 1

Antimetabolites
    Folate Anatagonists
        Methotrexate (FOLEX ™)
        Trimetrexate (NEUTREXIN ™)
        Pemetrexed (ALIMTA ™)
    Purine Analogs
        Allopurinol (ZYLOPRIM ™)
        Mercaptopurine (PURINETHOL ™)
        Fludarabine (FLUDARA ™)
        Thioguanine (6-TG)
        Cladribine (LEUSTATIN ™)
        Pentostatin (NIPENT ™)
    Pyrimidine Analogs
        Capecitabine (XELODA ™)
        Cytarabine (CYTOSAR ™)
        Liposomal cytarabine (DEPOCYT ™)
        Floxuridine (FUDR ™)
        Fluorouracil (ADRUCIL ™)
        Gemcitabine (GEMZAR ™)
        Clofarabine (CLOLAR ™)
        Decitabine (DACOGEN ™)
        Azacitadine (VIDAZA ™)
Enzyme Inhibitors
    COX-2 Inhibitors (CELEBREX ™)
    Topoisomerase II Inhibitors
        Epipodophyllotoxins
        Etoposide (VEPESID ™, ETOPOPHOS ™)
        Teniposide (VUMON ™, VM 26 ™)
    Anthracyclines
        Daunorubicin (CERUBIDINE ™)
        Liposomal Daunorubicin (DAUNOXOME ™)
        Doxorubicin (ADRIAMYCIN ™, RUBEX ™)
        Liposomal Doxorubicin (DOXIL ™)
        Epirubicin (ELLENCE ™)
        Valrubicin (VALSTAR ™)
        Idarubicin (IDAMYCIN ™)
        Mitoxantrone (NOVANTRONE ™)
    Topoisomerase I Inhibitors
        Camptothecins
        Irinotecan (CAMPTOSAR ™)
        Topotecan (HYCAMTIN ™)
    Anticancer Kinase Inhibitors
        Imatinib mesylate (GLEEVEC ™)
        Gefitinib (IRESSA ™)
        Erlotinib (TARCEVA ™)
        Sorafenib (NEXAVAR ™)
        Sunitinib (SUTENT ™)
        Nilotinib (TASIGNA ™)
        Everolimus (AFINITOR ™)
        Lapatinib (TYKERB ™)
        Dasatinib (SPRYCEL ™)
Antitubulins
    Taxanes
        Docetaxel (TAXOTERE ™)
        Paclitaxel (TAXOL ™)
        Ixabepilone (IXEMPRA ™)
        Cabazitaxel (JEVTANA ™)
    Vinca Alkaloids
        Vinblastine (VELBAN ™)
        Vincristine (ONCOVIN ™)
        Vinorelbine (NAVELBINE ™)
        Vinflunine (JAVLOR ™)

TABLE 1-continued

ILX-651 (TASIDOTIN™)
Tasidotin-C-carboxylate
Estramustine (EMCYT™)
Anticancer Phototherapeutics
    Porfimer Sodium (PHOTOFRIN™)
Anticancer Antibodies
    Anti-CD52 Antibodies
        Alemtuzumab (CAMPATH™)
    Anti-CD33 Antibodies
        Gemtuzumab ozogamicin (MYLOTARG™)
    Anti-CD20 Antibodies
        Ibritumomab (ZEVALIN™)
        Rituximab (RITUXAN™)
        Tositumomab (BEXXAR™)
        Ofatumumab (ARZERRA™)
    Anti-Her2 Antibodies
        Trastuzumab (HERCEPTIN™)
    Anti-VEGF
        Bevacizumab (AVASTIN™)
    Anti-EGFR
        Cetuximab (ERBITUX™)
Anticancer Retinoids
    Alitretinoin (PANRETIN™)
    Bexarotene (TARGRETIN™)
    Tretinoin (VESANOID™, ATRA™)
    Octreotide acetate (SANDOSTATIN™)
Normal Tissue Protectors
    Amifostine (ETHYOL™)
    Darbepoetin alfa (ARANESP™)
    Dexrazoxane (ZINECARD™)
    Epoetin alfa (EPOGEN™, PROCRIT™)
    Filgrastim (NEUPOGEN™)
    Folinic Acid (leucovorin)
    Allopurinol (ALOPRIM™)
    Mesna (MESNEX™)
    Oprelvekin (rhIL-11) (NEUMEGA™)
    Pegfilgrastim (NEULASTA™)
    GM-CSF (sargramostim, PROKINE™, LEUKINE™)
    Eltrombopag (PROMACTA™)
    AMD3100 (plerixafor, MOZOBIL™)
Alkylating Agents
    Alkyl Sulfonates
        Busulfan (MYLERAN™)
    Platinum Analogs
        Carboplatin (PARAPLATIN™)
        Cisplatin (PLATINOL™-AQ)
        Oxaliplatin (ELOXATIN™)
    Nitrosoureas
        Carmustine (BICNU™)
        Lomustine (CCNU™, CEENU™)
        Streptozocin (ZANOSAR™)
    Nitrogen Mustards
        Chlorambucil (LEUKERAN™)
        Uracil mustard Cyclophosphamide (CYTOXAN™)
        Ifosfamide (IFEX™)
        Mechlorethamine (MUSTARGEN™)
        Melphalan (ALKERAN™, L-PAM)
        Bendamustine (TREANDA™)
    Triazenes
        Dacarbazine (DTIC-DOME™)
        Procarbazine (MATULANE™)
        Temozolomide (TEMODAR™)
    Ethylenimines
        Hexamethylamine (HEXALEN™, altretamine, HEXASTAT™)
        Thiotepa (THIOPLEX™, TESPA™)
    Hydroxyurea (HYDREA™)
    Arsenic trioxide (TRISENOX™)
    Mitomycin C (MUTAMYCIN™)
    Trabectedin (YONDELIS™)
Anticancer Antibiotics
    Actinomycin D (dactinomycin, COSMEGEN™)
    Bleomycin sulfate (BLENOXANE™)
    Plicamycin (MITHRACIN™)
Proteasome Inhibitors
    Bortezomib (VELCADE™)
Anticancer Anti-hormones
    LHRH Agonists
        Histrelin (VANTAS™)
        Goserelin (ZOLADEX™)
        Leuprolide (LUPRON™, ELIGARD™)
        Triptorelin (TRELSTAR™)
    Anti-Androgens
        Bicalutamide (CASODEX™)
        Flutamide (EULEXIN™)
        Nilutamide (NILANDRON™)
        Aminoglutethimide (CYTADREN™)
        Abarelix (PLENAXIS™)
    Anti-Estrogens and Aromatase Inhibitors
        Tamoxifen (NOLVADEX™)
        Raloxifene (EVISTA™)
        Anastrozole (ARIMIDEX™)
        Exemestane (AROMASIN™)
        Fulvestrant (FASLODEX™)
        Letrozole (FEMARA™)
        Fluoxymesterone (HALOTESTIN™)
        Megestrol acetate (MEGACE™)
Bisphosphonates
    Pamidronate (AREDIA™)
    Zoledronate (ZOMETA™)
    Ibandronate (BONIVA™)
Anticancer Enzymes
    Asparaginase (ELSPAR™)
    Pegademase (ADAGEN™)
    Pegaspargase (ONCASPAR™)
Anticancer Cytokines
    Aldesleukin (rhIL-2) (PROLEUKIN™)
    Denileukin Diftitox (ONTAK™)
    Interferon alfa-2b (INTRON™ A)
    Peginterferon alfa-2a (PEGASYS™)

Treatment will depend on the cancer in question. Tests can be performed prior to treatment to specifically tailor a treatment for a patient. Such tests may include genetic or protein marker testing of tumor markers to determine susceptibility or resistance to a particular drug or class of drugs. For example, recently a mutation in von Hippel-Landau (VHL) gene have been found to be associated with a more favorable drug response for drugs such as SUTENT™, NEXAVAR™, and AVASTIN™. Other genetic and protein tests can be performed to link a treatment to an appropriate patient population.

The agents described above can be provided in formulations obtained from the manufacturer. Such formulations typically include the active components mixed with a pharmaceutically acceptable vehicle or excipient. The vehicle may contain minor amounts of auxiliary substances such as wetting or emulsifying agents. The formulations may also include ancillary substances, such as pharmacological agents, cytokines, or other biological response modifiers.

In other embodiments of the invention, the pharmaceutical composition comprising the agent is a sustained-release formulation, and/or a formulation that is administered using a sustained-release device. Such devices are well known in the art, and include, for example, transdermal patches, and miniature implantable pumps (such as described herein) that can provide for drug delivery over time in a continuous, steady-state fashion at a variety of doses to achieve a sustained-release effect with either a non-sustained-release or a sustained release pharmaceutical composition. For example, polypeptide agents and antibodies described herein are suitable agents for delivery using an osmotic delivery device such as the DUROS™ implantable device described above. In this embodiment, two or more such implantable delivery devices can be used, one including the GLP-1 receptor agonist and one or more including one or more additional beneficial agents, such as anticancer polypeptide formulations, antibodies, and the like. See, e.g., U.S. Patent Publication 2009/0202608, incorporated herein by reference in its entirety, for a description of the use of two or more implantable delivery devices.

The additional beneficial agents may also be formulated as particle and suspension formulations as described herein, if appropriate. Such particle and suspension formulations are useful with polypeptide agents and antibodies and can be delivered using implantable devices as described above. In addition to the suspension formulations, comprising a suspension vehicle and particle formulation, described above, some polypeptide agents (e.g., leuprolide acetate) can be directly dissolved or dispersed in a vehicle for delivery from implantable devices. For example, some polypeptides (e.g., leuprolide acetate) can be dissolved in non-aqueous polar aprotic solvents (e.g., dimethylsulfoxide) to provide peptide formulations (see, e.g., U.S. Pat. Nos. 5,932,547; 6,235,712; 5,981,489, incorporated herein by reference in their entireties). The use of one such formulation in an implantable osmotic delivery device is described below in Example 5. Other examples of peptide formulations include, but are not limited to, non-aqueous protic peptide formulations (see, e.g., U.S. Pat. No. 6,066,619, incorporated herein by reference in its entirety) and aqueous formulations of peptides (see, e.g., U.S. Pat. No. 6,068,850, incorporated herein by reference in its entirety).

Other suitable routes of administration for the beneficial agents include parenteral administration, such as subcutaneous (s.c.), intraperitoneal (i.p.), intramuscular (i.m.), intravenous (i.v.), or infusion, oral (p.o.) and pulmonary, nasal, topical, transdermal, and suppositories. Where the composition is administered via pulmonary delivery, the therapeutically effective dose is adjusted such that the soluble level of the agent in the bloodstream, is equivalent to that obtained with a therapeutically effective dose that is administered parenterally, for example s.c., i.p., i.m., or i.v. In some embodiments of the invention, the pharmaceutical composition comprising the beneficial agent is administered by i.m. or s.c. injection, particularly by i.m. or s.c. injection locally to the region where the GLP-1 receptor agonist is administered.

One or more therapeutically effective dose of the additional beneficial agent, such as an anticancer agent will be administered. By "therapeutically effective dose or amount" of each of these agents is intended an amount that when administered in combination with the other agents, brings about a positive therapeutic response with respect to treatment of an individual with cancer. Of particular interest is an amount of these agents that provides an anti-tumor effect, as defined herein. In certain embodiments, multiple therapeutically effective doses of the additional beneficial agent will be provided.

The additional beneficial agents can be administered prior to, concurrent with, or subsequent to administration of the GLP-1 receptor agonist. For example, initial treatment with a chemotherapeutic agent can be performed, followed by implantation of a delivery device including the GLP-1 receptor agonist formulation or vice versa. Moreover, the additional beneficial agent may be administered over the time that the GLP-1 receptor agonist formulation is also being delivered. By "concurrent therapy" is intended administration to a subject such that the therapeutic effect of the combination of the substances is caused in the subject undergoing therapy.

5.0.0 Uses

The GLP-1 receptor agonists, e.g., exenatide and GLP-1(7-36)amide, optionally in combination with other beneficial agents, can be used to treat various cancers. In particular, as explained above, cancer cells are known to exhibit increased glycolysis as compared to normal cells. An advantage of the present invention is that inhibiting glucose availability to cancer cells by using a GLP-1 receptor agonist, such as exenatide and GLP-1(7-36)amide, effectively reduces the amount of energy metabolites such as ATP and NADH produced, thereby starving the cancer cell of energy.

Any number of cancers can benefit from the delivery of GLP-1 receptor agonists. For example, tumors or cancers such as hemangiomas, neufibromatosis, breast, colorectal, lung, brain and CNS, renal, gynecological (e.g., ovarian, fallopian, cervical, peritoneal), hematological (lymphoma, multiple myeloma, leukemia), neuroendocrine, mesothelioma, melanoma, prostate, esophagus, liver, gastric, rectal, carcinoid tumors; head and neck, squamous cell carcinoma, sarcomas, pancreas, colon, thymoma, thyroid, small intestine, bladder, testicular, bile duct, gall bladder, kidney, gastrointestinal stromal tumors, endometrial cancers and choriocarcinoma. A list of cancers that may benefit from delivery of the GLP-1 receptor agonists is shown in Table 2.

TABLE 2

Acute Lymphoblastic Leukemia, Adult
Acute Lymphoblastic Leukemia, Childhood
Acute Myeloid Leukemia, Adult
Acute Myeloid Leukemia, Childhood
Adrenocortical Carcinoma
Adrenocortical Carcinoma, Childhood
AIDS-Related Cancers
AIDS-Related Lymphoma
Anal Cancer
Appendix Cancer
Atypical Teratoid/Rhabdoid Tumor, Childhood, Central Nervous System
Basal Cell Carcinoma, see Skin Cancer (Non-melanoma)
Bladder Cancer
Bladder Cancer, Childhood
Bone Cancer, Osteosarcoma and Malignant Fibrous Histiocytoma
Brain Stem Glioma, Childhood
Brain Tumor, Adult
Brain Tumor, Brain Stem Glioma, Childhood
Brain Tumor, Central Nervous System Atypical Teratoid/Rhabdoid Tumor, Childhood
Brain Tumor, Central Nervous System Embryonal Tumors, Childhood
Brain Tumor, Cerebellar Astrocytoma, Childhood
Brain Tumor, Cerebral Astrocytoma/Malignant Glioma, Childhood
Brain Tumor, Craniopharyngioma, Childhood
Brain Tumor, Ependymoblastoma, Childhood
Brain Tumor, Ependymoma, Childhood
Brain Tumor, Medulloblastoma, Childhood
Brain Tumor, Medulloepithelioma, Childhood
Brain Tumor, Pineal Parenchymal Tumors of Intermediate Differentiation, Childhood
Brain Tumor, Supratentorial Primitive Neuroectodermal Tumors and Pineoblastoma, Childhood
Brain Tumor, Visual Pathway and Hypothalamic Glioma, Childhood
Brain and Spinal Cord Tumors, Childhood (Other)
Breast Cancer
Breast Cancer and Pregnancy
Breast Cancer, Childhood
Breast Cancer Male
Bronchial Tumors, Childhood
Burkitt Lymphoma
Carcinoid Tumor, Childhood
Carcinoid Tumor, Gastrointestinal
Carcinoma of Unknown Primary
Central Nervous System Embryonal Tumors, Childhood
Central Nervous System Lymphoma, Primary
Cerebral Astrocytoma/Malignant Glioma, Childhood
Cervical Cancer
Cervical Cancer, Childhood
Childhood Cancers
Chordoma, Childhood
Chronic Lymphocytic Leukemia
Chronic Myelogenous Leukemia
Chronic Myeloproliferative Disorders
Colon Cancer
Colorectal Cancer, Childhood TABLE 2-continued Cutaneous T-Cell Lymphoma, see Mycosis Fungoides and Sezary Syndrome
Ependymoma, Childhood
Esophageal Cancer
Esophageal Cancer, Childhood
Ewing Family of Tumors
Extracranial Germ Cell Tumor, Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastrointestinal Carcinoid Tumor
Gastrointestinal Stromal Tumor (GIST)
Gastrointestinal Stromal Cell Tumor, Childhood
Germ Cell Tumor, Extracranial, Childhood
Germ Cell Tumor, Extragonadal
Germ Cell Tumor, Ovarian
Gestational Trophoblastic Tumor
Glioma, Adult
Glioma, Childhood, Brain Stem
Glioma, Childhood Cerebral Astrocytoma
Hairy Cell Leukemia
Head and Neck Cancer
Hepatocellular (Liver) Cancer, Adult, (Primary)
Hepatocellular (Liver) Cancer, Childhood, (Primary)
Histiocytosis, Langerhans Cell
Hodgkin Lymphoma, Adult
Hodgkin Lymphoma, Childhood
Hypopharyngeal Cancer
Hypothalamic and Visual Pathway Glioma, Childhood
Islet Cell Tumors (Endocrine Pancreas)
Kaposi Sarcoma
Kidney (Renal Cell) Cancer
Kidney Cancer, Childhood
Laryngeal Cancer
Laryngeal Cancer, Childhood
Lip and Oral Cavity Cancer
Liver Cancer, Adult, (Primary)
Liver Cancer, Childhood, (Primary)
Malignant Fibrous Histiocytoma of Bone and Osteosarcoma
Mesothelioma, Adult, Malignant
Mesothelioma, Childhood
Metastatic Squamous Neck Cancer with Occult Primary
Mouth Cancer
Multiple Endocrine Neoplasia Syndrome, Childhood
Multiple Myeloma/Plasma Cell Neoplasm
Mycosis Fungoides
Myelodysplastic Syndromes
Myelodysplastic/Myeloproliferative Diseases
Nasal Cavity and Paranasal Sinus Cancer
Nasopharyngeal Cancer
Nasopharyngeal Cancer, Childhood
Neuroblastoma
Non-Hodgkin Lymphoma, Adult
Non-Hodgkin Lymphoma, Childhood
Non-Small Cell Lung Cancer
Oral Cancer, Childhood
Oral Cavity Cancer, Lip tongue and mouth
Oropharyngeal Cancer
Ovarian Cancer, Childhood
Ovarian Epithelial Cancer
Ovarian Germ Cell Tumor
Ovarian Low Malignant Potential Tumor
Pancreatic Cancer
Pancreatic Cancer, Childhood
Pancreatic Cancer, Islet Cell Tumors
Papillomatosis, Childhood
Parathyroid Cancer
Penile Cancer
Pharyngeal Cancer
Pheochromocytoma
Pineoblastoma and Supratentorial Primitive Neuroectodermal Tumors, Childhood
Pituitary Tumor
Pleuropulmonary Blastoma
Prostate Cancer
Rectal Cancer
Respiratory Tract Carcinoma Involving the NUT Gene on Chromosome 15
Rhabdomyosarcoma, Childhood TABLE 2-continued Salivary Gland Cancer
Salivary Gland Cancer, Childhood
Sarcoma, Ewing Family of Tumors
Sezary Syndrome
Skin Cancer (Non-melanoma)
Skin Cancer, Childhood
Skin Cancer (Melanoma)
Skin Carcinoma, Merkel Cell
Small Cell Lung Cancer
Small Intestine Cancer
Soft Tissue Sarcoma, Adult
Soft Tissue Sarcoma, Childhood
Squamous Neck Cancer with Occult Primary, Metastatic
Stomach (Gastric) Cancer
Stomach (Gastric) Cancer, Childhood
Testicular Cancer
Throat Cancer
Thymoma and Thymic Carcinoma
Thymoma and Thymic Carcinoma, Childhood
Thyroid Cancer
Thyroid Cancer, Childhood
Transitional Cell Cancer of the Renal Pelvis and Ureter
Trophoblastic Tumor, Gestational
Unusual Cancers of Childhood
Ureter and Renal Pelvis, Transitional Cell Cancer
Urethral Cancer
Uterine Cancer, Endometrial
Uterine Sarcoma
Vaginal Cancer
Vaginal Cancer, Childhood
Vulvar Cancer
Waldenstrom Macroglobulinemia
Wilms Tumor In some embodiments, the GLP-1 receptor agonists, are used in the treatment of hematological tumors and/or solid tumors. In a preferred embodiment, the GLP-1 receptor agonists, for example, exenatide and GLP-1(7-36)amide, are used in the treatment of solid tumors.

The GLP-1 receptor agonists are delivered in order to provide a positive therapeutic response. By "positive therapeutic response" it is intended the individual undergoing the combination treatment of a GLP-1 receptor agonist, such as exenatide and GLP-1(7-36)amide, and an additional beneficial agent exhibits an improvement in one or more symptoms of the cancer for which the individual is undergoing therapy. Therefore, for example, a positive therapeutic response refers to one or more of the following improvements in the disease: (1) reduction in tumor size; (2) reduction in the number of cancer cells; (3) inhibition (i.e., slowing to some extent, preferably halting) of tumor growth; (4) inhibition (i.e., slowing to some extent, preferably halting) of cancer cell infiltration into peripheral organs; (5) inhibition (i.e., slowing to some extent, preferably halting) of tumor metastasis; and (6) some extent of relief from one or more symptoms associated with the cancer. Such therapeutic responses may be further characterized as to degree of improvement. Thus, for example, an improvement may be characterized as a complete response. By "complete response" is documentation of the disappearance of all symptoms and signs of all measurable or evaluable disease confirmed by physical examination, laboratory, nuclear and radiographic studies (i.e., CT (computer tomography) and/or MRI (magnetic resonance imaging)), and other non-invasive procedures repeated for all initial abnormalities or sites positive at the time of entry into the study. Alternatively, an improvement in the disease may be categorized as stabilization of the disease or may be a partial response. By "partial response" is intended a reduction of greater than 50% in the sum of the products of the perpendicular diameters of one or more measurable lesions when compared with pretreatment measurements (for patients with evaluable response only, partial response does not apply).

In one embodiment, the GLP-1 receptor agonist is delivered in a suspension formulation, administered using an osmotic delivery device as described above. Examples of target rates of delivery for suspension formulations of the present invention, comprising GLP-1 receptor agonists, include, but are not limited to: suspension formulations comprising particle formulations comprising GLP-1 (e.g., GLP-1(7-36)amide), between about 20 µg/day and about 900 µg/day, preferably between about 100 µg/day and about 600 µg/day, for example, at about 480 µg/day; and suspension formulations comprising particle formulations comprising exenatide, between about 5 µg/day and about 320 µg/day, preferably between about 5 µg/day and about 160 µg/day, for example, at about 10 µg/day to about 20 µg/day, such as 10, 20, 40, 60, 80, 100, 120 µg/day, or any integers between the above ranges. An exit sheer rate of the suspension formulation from the osmotic delivery device is determined such that the target daily target delivery rate of the GLP-1 receptor agonist is reasonably achieved by substantially continuous, uniform delivery of the suspension formulation from the osmotic delivery device. Examples of exit sheer rates include, but are not limited to, about 1 to about $1 \times 10^4$ reciprocal second, preferably about $4 \times 10^{-2}$ to about $6 \times 10^4$ reciprocal second, more preferably $5 \times 10^{-3}$ to $1 \times 10^{-3}$ reciprocal second.

As explained above, a subject being treated with the GLP-1 receptor agonist formulations of the present invention may also benefit from co-treatment with other beneficial agents, including anticancer agents described above, as well as antidiabetic agents.

Additional beneficial agents that can be delivered include, but are not limited to, pharmacologically beneficial peptides proteins, polypeptides, genes, gene products, other gene therapy agents, or other small molecules. The additional beneficial agents are useful for the treatment of a variety of conditions including but not limited to hemophilia and other blood disorders, growth disorders, diabetes, leukemia and lymphoma, hepatitis, renal failure, bacterial infection, viral infection (e.g., infection by HIV, HCV, etc.), hereditary diseases such as cerbrosidase deficiency and adenosine deaminase deficiency, hypertension, septic shock, autoimmune diseases (e.g., Graves disease, systemic lupus erythematosus and rheumatoid arthritis), shock and wasting disorders, cystic fibrosis, lactose intolerance, Crohn's disease, inflammatory bowel disease, Alzheimer's disease, metabolic disorders (such as obesity), and cancers.

The polypeptides may include but are not limited to the following: glucagon-like peptide 2 (GLP-2), cholecystokinin (CCK), CCK octapeptide, growth hormone, somatostatin; somatropin, somatotropin, somatotropin analogs, somatomedin-C, somatotropin plus an amino acid, somatotropin plus a protein; follicle stimulating hormone; luteinizing hormone, luteinizing hormone-releasing hormone (LHRH), LHRH analogs/agonists such as leuprolide, nafarelin and goserelin, LHRH antagonists; growth hormone releasing factor; calcitonin; colchicine; gonadotropins such as chorionic gonadotropin; antiandrogens such as flutamide, nilutamide and cytoprerone; aromatase inhibitors such as exemastane, letrozole and anastrazole; selective estrogen receptor modulators such as raloxifene, lasoxifene; oxytocin, octreotide; vasopressin; adrenocorticotrophic hormone; epidermal growth factor; fibroblast growth factor; platelet-derived growth factor; transforming growth factor; nerve growth factor; prolactin; cosyntropin; lypressin polypeptides such as thyrotropin releasing hormone; thyroid stimulation hormone; secretin; leptin; adiponectin; amylin, amylin analogs (e.g., pramlintide acetate); pancreozymin; enkephalin; glucagon; endocrine agents secreted internally and distributed by way of the bloodstream; carbohydrases, nucleases, lipase, proteases, amylase, or the like.

Further beneficial agents that may be delivered include but are not limited to the following: alpha antitrypsin; factor VII; factor IX, thrombin and other coagulation factors; insulin; peptide hormones; adrenal cortical stimulating hormone, thyroid stimulating hormone and other pituitary hormones; erythropoietin; growth factors such as granulocyte-colony stimulating factor, granulocyte-macrophage colony stimulating factor, thrombopoietin, insulin-like growth factor 1; tissue plasminogen activator; CD4; 1-deamino-8-D-arginine vasopressin; interleukin-1 receptor antagonist; tumor necrosis factor, tumor necrosis factor receptor; tumor suppresser proteins; pancreatic enzymes; lactase; cytokines, including lymphokines, chemokines or interleukins such as interleukin-1, interleukin-2 and other members of the interleukin family (e.g., IL-1, 6, 12, 15, 17, 18, 32); cytotoxic proteins; superoxide dismutase; endocrine agents secreted internally and distributed in an animal by way of the bloodstream; recombinant antibodies, antibody fragments, humanized antibodies, single chain antibodies, monoclonal antibodies; avimers; or the like.

Further, the beneficial agents that may be administered include, but are not limited to, organic compounds including those compounds that transport across a vessel. Examples of beneficial agents that may be used in the practice of the present invention include, but are not limited to, the following: hypnotics and sedatives such as pentobarbital sodium, phenobarbital, secobarbital, thiopental, amides and ureas exemplified by diethylisovaleramide and alpha-bromo-isovaleryl urea, urethanes, or disulfanes; heterocyclic hypnotics such as dioxopiperidines, and glutarimides; antidepressants such as isocarboxazid, nialamide, phenelzine, imipramine, tranylcypromine, pargyline; tranquilizers such as chloropromazine, promazine, fluphenazine reserpine, deserpidine, meprobamate, benzodiazepines such as chlordiazepoxide; tricyclic antidepressants; anticonvulsants such as primidone, diphenylhydantoin, ethltoin, pheneturide, ethosuximide; muscle relaxants and anti-parkinson agents such as mephenesin, methocarbomal, trihexylphenidyl, biperiden, levo-dopa, also known as L-dopa and L-beta-3-4-dihydroxyphenylalanine; analgesics such as morphine, codeine, meperidine, nalorphine; antipyretics and anti-inflammatory agents such as aspirin, salicylamide, sodium salicylamide, naproxin, ibuprofen, acetaminophen; local anesthetics such as procaine, lidocaine, naepaine, piperocaine, tetracaine, dibucane; antispasmodics and antiulcer agents such as atropine, scopolamine, methscopolamine, oxyphenonium, papaverine, prostaglandins such as $PGE_1$, $PGE_2$, $PGF_1alpha$, $PGF_2alpha$, PGA; anti-microbials such as penicillin, tetracycline, oxytetracycline, chlorotetracycline, chloramphenicol, sulfonamides, bacitracin, chlorotetracycline, levofloxacin, erythromycin; anti-fungals such as Amphotericin B; anti-malarials such as 4-aminoquinolines, 8-aminoquinolines and pyrimethamine; hormonal agents such as prednisolone, cortisone, cortisol and triamcinolone, androgenic steroids (for example, methyltestosterone, fluoxmesterone), estrogenic steroids (for example, 17-beta-estradiol and ethinyl estradiol), progestational steroids (for example, 17-alpha-hydroxyprogesterone acetate, 19-nor-progesterone, norethindrone); sympathomimetic drugs such as epinephrine, amphetamine, ephedrine, norepinephrine; cardiovascular drugs such as procainamide, amyl nitrate, nitroglycerin, dipyridamole, sodium nitrate, mannitol nitrate; diuretics such as acetazolamide, chlorothiazide, flumethiazide; antiparasitic agents such as bephenium hydroxynaphthoate, dichlorophen, enitabas, dapsone; antineoplastic agents such as mechloroethamine, uracil mustard, 5-fluorouracil, 6-thioguanine, procarbazine, paclitaxel, docetaxel, carboplatin, gemcitabine, oxaliplatin, fludarabine, ara-C, camptothecin, bortezomib, methrotrexate, capecitabine, doxorubicin, vincristine, cyclophosphamide, etoposide; VEGF/EGF inhibitors (for example, small molecules and antibodies); VEGF/EGF receptor inhibitors; hypoglycemic drugs such as insulin related compounds (for example, isophane insulin suspension, protamine zinc insulin suspension, globin zinc insulin, extended insulin zinc suspension) tolbutamide, acetohexamide, tolazamide, chlorpropamide; nutritional agents such as vitamins, essential amino acids, and essential fats; eye drugs such as pilocarpine base, pilocarpine hydrochloride, pilocarpine nitrate; antiviral drugs such as disoproxil fumarate, aciclovir, cidofovir, docosanol, famciclovir, fomivirsen, foscarnet, ganciclovir, idoxuridine, penciclovir, trifluridine, tromantadine, valaciclovir, valganciclovir, vidarabine, amantadine, arbidol, oseltamivir, peramivir, rimantadine, zanamivir, abacavir, didanosine, emtricitabine, lamivudine, stavudine, zalcitabine, zidovudine, tenofovir, efavirenz, delavirdine, nevirapine, loviride, amprenavir, atazanavir, darunavir, fosamprenavir, indinavir, lopinavir, nelfinavir, ritonavir, saquinavir, tipranavir, enfuvirtide, adefovir, fomivirsen, imiquimod, inosine, podophyllotoxin, ribavirin, viramidine, fusion inhibitors specifically targeting viral surface proteins or viral receptors (for example, gp-41 inhibitor (T-20), CCR-5 inhibitor, enfuvirtide (FUZEON™)); anti-nausea (such as scopolamine, dimenhydrinate, granisetron, dolasetron, palonesetron, metaclopramide, ondansetron); iodoxuridine, hydrocortisone, eserine, phospholine, iodide, as well as other beneficial agents.

Numerous peptides, proteins, or polypeptides that are useful in the practice of the present invention are described herein. In addition to the peptides, proteins, or polypeptides described, modifications of these peptides, proteins, or polypeptides are also known to one of skill in the art and can be used in the practice of the present invention following the guidance presented herein. Such modifications include, but are not limited to, amino acid analogs, amino acid mimetics, analog polypeptides, or derivative polypeptides. Further, the beneficial agents disclosed herein may be formulated singly or in combination (e.g., mixtures).

Peptide YY (PYY) inhibits gut motility and blood flow (Laburthe, M., Trends Endocrinol Metab. 1(3):168-74 (1990), mediates intestinal secretion (Cox, H. M., et al., Br J Pharmacol 101(2):247-52 (1990); Playford, R. J., et al., Lancet 335(8705):1555-7 (1990)), stimulate net absorption (MacFayden, R. J., et al., Neuropeptides 7(3):219-27 (1986)), and two major in vivo variants (PYY and $PYY_{3-36}$) have been identified (e.g., Eberlein, G. A., et al., Peptides 10 (4), 797-803 (1989)). The sequence of PYY, as well as analogs and derivatives thereof, including $PYY_{3-36}$, are known in the art (e.g., U.S. Pat. Nos. 5,574,010 and 5,552,520). For ease of reference herein, the family of PYY polypeptides, PYY derivatives, variants and analogs are referred to collectively as PYY.

GIP is an insulinotropic peptide hormone (Efendic, S., Horm Metab Res. (2004) 36:742-746) and is secreted by the mucosa of the duodenum and jejunum in response to absorbed fat and carbohydrate that stimulate the pancreas to secrete insulin. GIP stimulates insulin secretion from pancreatic beta cells in the presence of glucose (Tseng et al., PATAS (1993) 90:1992-1996). GIP circulates as a biologically active 42-amino acid peptide. GIP is also known as glucose-dependent insulinotropic protein. The sequence of GIP, as well as peptide analogs and peptide derivatives thereof, are known in the art (see, e.g., Meier J. J., Diabetes Metab Res Rev. (2005) 21(2):91-117; Efendic S., Horm Metab Res. (2004) 36(11-12):742-746). For ease of reference herein, the family of GIP polypeptides, GIP derivatives, variants and analogs are referred to collectively as GIP.

Oxyntomodulin is a naturally occurring 37 amino acid peptide hormone found in the colon that has been found to suppress appetite and facilitate weight loss (Wynne K, et al., Int J Obes (Lond) 30(12):1729-36 (2006)). The sequence of oxyntomodulin, as well as analogs and derivatives thereof, are known in the art (e.g., U.S. Patent Publication Nos. 2005-0070469 and 2006-0094652). For ease of reference herein, the family of oxyntomodulin polypeptides, oxyntomodulin derivatives, variants and analogs are referred to collectively as oxyntomodulin.

Amylin, as well as analogs and derivatives thereof: are known in the art (e.g., U.S. Pat. Nos. 5,686,411, 5,814,600, 5,998,367, 6,114,304, 6,410,511, 6,608,029, and 6,610,824). For ease of reference herein, the family of amylin polypeptides, amylin derivatives, variants and analogs are referred to collectively as amylin.

The cDNA sequence encoding the human leptin protein hormone is known (e.g., Masuzaki, H., et al. (Diabetes 44: 855-858, 1995)). Leptin, as well as analogs and derivatives thereof, are known in the art (e.g., U.S. Pat. Nos. 5,521,283, 5,525,705, 5,532,336, 5,552,522, 5,552,523, 5,552,524, 5,554,727, 5,559,208, 5,563,243, 5,563,244, 5,563,245, 5,567,678, 5,567,803, 5,569,743, 5,569,744, 5,574,133, 5,580,954, 5,594,101, 5,594,104, 5,605,886, 5,691,309, and 5,719,266; P.C.T. International Patent Publication Nos. WO96/22308, WO96/31526, WO96/34885, 97/46585, WO97/16550, and WO 97/20933; European Patent Publication No. EP 0 741 187). For ease of reference herein, the family of leptin polypeptides, leptin derivatives, variants and analogs are referred to collectively as leptin.

Further, oligonucleotides (e.g., RNA, DNA, alternative backbones) may be used as beneficial agents in the practice of the present invention. In one embodiment therapeutic RNA molecules may include, but are not limited to, small nuclear RNAs (snRNAs), and small interfering RNA strands (siRNA) for use in RNA interference (RNAi) inhibition of gene expression. RNAi inhibition typically occurs at the stage of translation or by hindering the transcription of specific genes. RNAi targets include, but are not limited to, RNA from viruses and genes with roles in regulating development and genome maintenance.

The beneficial agents can also be in various forms including, but not limited to, the following: uncharged molecules; components of molecular complexes; and pharmacologically acceptable salts such as hydrochloride, hydrobromide, sulfate, laurates, palmatates, phosphate, nitrate, borate, acetate, maleate, tartrate, oleates, or salicylates. For acidic drugs, salts of metals, amines or organic cations, for example, quaternary ammonium, can be employed. Furthermore, simple derivatives of the drug such as esters, ethers, amides and the like that have solubility characteristics suitable for the purpose of the invention can also be used herein. The formulation used can have been in various art known forms such as solution, dispersion, paste, cream, particle, granule, tablet, emulsions, suspensions, powders and the like. In addition to the one or more beneficial agents, the beneficial agent formulation may optionally include pharmaceutically acceptable carriers and/or additional ingredients such as antioxidants, stabilizing agents, buffers, and permeation enhancers.

The amount of beneficial agent used is that amount necessary to deliver a therapeutically effective amount of the agent to achieve the desired therapeutic result. In practice, this will vary depending upon such variables, for example, as the particular agent, the site of delivery, the severity of the condition, and the desired therapeutic effect. Beneficial agents and their dosage unit amounts are known to the prior art in Goodman & Gilman's The Pharmacological Basis of Therapeutics, 11th Ed., (2005), McGraw Hill; Remington's Pharmaceutical Sciences, 18th Ed., (1995), Mack Publishing Co.; and Martin's Physical Pharmacy and Pharmaceutical Sciences, 1.00 edition (2005), Lippincott Williams & Wilkins.

The additional beneficial agent can be delivered using any of the various delivery techniques outlined above, including without limitation parenterally (including by subcutaneous, intravenous, intramedullary, intraarticular, intramuscular, or intraperitoneal injection) rectally, topically, transdermally, intranasally, by inhalation, or orally (for example, in capsules, suspensions, or tablets). In certain embodiments, the agent is in a sustained-release formulation, or administered using a sustained-release device. Such devices are well known in the art, and include, for example, transdermal patches, and miniature implantable pumps (such as the DUROS™ delivery device described herein) that can provide for drug delivery over time in a continuous, steady-state fashion at a variety of doses to achieve a sustained-release effect with a non-sustained-release pharmaceutical composition. If an osmotic delivery device is used, the volume of a beneficial agent chamber comprising the beneficial agent formulation is between about 50 µl to about 1000 µl, more preferably between about 100 µl and about 500 µl, more preferably between about 150 µl and about 200 µl. Moreover, two or more such devices can be used, one including the GLP-1 receptor agonist and one or more including one or more additional beneficial agents, such as an antidiabetic compound. See, e.g., U.S. Patent Publication 2009/0202608, incorporated herein by reference in its entirety, for a description of the use of two or more implantable delivery devices.

An example of a cancer treatment using delivery of an anticancer agent from a first osmotic delivery device and delivery of a GLP-1 receptor agonist from a second osmotic delivery device is presented below in Example 5. In the example, the cancer is prostate cancer, the anticancer agent is leuprolide acetate and the GLP-1 receptor agonist is exenatide.

Other objects may be apparent to one of ordinary skill upon reviewing the following specification and claims.

6.0.0 Experimental

The following examples are put forth so as to provide those of ordinary skill in the art with a complete disclosure and description of how to make and use the devices, methods, and formulae of the present invention, and are not intended to limit the scope of what the inventor regards as the invention. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The compositions produced according to the present invention meet the specifications for content and purity required of pharmaceutical products.

Example 1

Exenatide Particle Formulations

This example describes making exenatide particle formulations.

A. Formulation 1

Exenatide (0.25 g) was dissolved in 50 mM sodium citrate buffer at pH 6.04. The solution was dialyzed with a formulation solution containing sodium citrate buffer, sucrose, and methionine. The formulated solution was then spray dried using Buchi 290 with 0.7 mm nozzle, outlet temperature of 75° C., atomization pressure of 100 Psi, solid content of 2%, and flow rate of 2.8 mL/min. The dry powder contained 21.5% of exenatide with 4.7% residual moisture and 0.228 g/ml density.

B. Formulations 2 and 3

Two additional formulations of exenatide were prepared essentially by the method just described. Following here in Table 3 is a summary of the weight percentages (wt %) of the components of the Formulations 1, 2 and 3.

TABLE 3

| Component | Particle Formulation 1 (wt %) | Particle Formulation 2 (wt %) | Particle Formulation 3 (wt %) |
| --- | --- | --- | --- |
| Exenatide | 21.5 | 11.2 | 50.0 |
| Sodium Citrate* | 63.6 | 74.7 | 28.4 |
| Citric Acid* | 7.1 | 9.1 | 3.6 |
| Sucrose | 3.9 | 2.5 | 9.0 |
| Methionine | 3.9 | 2.5 | 9.0 |

*Sodium Citrate/Citric Acid formed the citrate buffer in the pre-spray drying process for preparation of this particle formulation.

Example 2

GLP-1 (7-36)Amide Dry Powder

This example describes making a GLP-1(7-36)amide particle formulation. GLP-1(7-36)amide (1.5 g) was dissolved in 5 mM sodium citrate buffer at pH 4. The solution was dialyzed with a formulation solution containing sodium citrate buffer and methionine. The formulated solution was then spray dried using Buchi 290 with 0.7 mm nozzle, outlet temperature of 70° C., atomization pressure of 100 Psi, solid content of 1.5%, and flow rate of 5 mL/min. The dry powder contained 90% of GLP-1(7-36)amide.

Example 3

Exenatide Suspension Formulation

This example describes making suspension formulations comprising a suspension vehicle and an exenatide particle formulation.

A. Suspension Formulation of 20 wt % Exenatide Particles

An exenatide particle formulation was generated by spray-drying, and contained 20 wt % exenatide, 32 wt % sucrose, 16 wt % methionine and 32 wt % citrate buffer.

A suspension vehicle was formed by dissolving the polymer polyvinylpyrrolidone in the solvent benzyl benzoate at approximately a 50/50 ratio by weight. The vehicle viscosity was approximately 12,000 to 18,000 poise when measured at 33° C. Particles containing the peptide exenatide were dispersed throughout the vehicle at a concentration of 10% particles by weight.

B. Suspension Formulations of Particle Formulations 1, 2, and 3

A suspension vehicle was formed by dissolving the polymer polyvinylpyrrolidone K-17 (typically having an approximate average molecular weight range of 7,900-10,800) in the solvent benzyl benzoate heated to approximately 65° C. under a dry atmosphere and reduced pressure at approximately a 50/50 ratio by weight. The vehicle viscosity was approximately 12,000 to 18,000 poise when measured at 33° C. Particle formulations 1-3, described in Example 1, were dispersed throughout the vehicle at the concentrations (by weight percent) shown in Table 4.

TABLE 4

| Component | Suspension Formulation 1 (wt %) | Suspension Formulation 2 (wt %) | Suspension Formulation 3 (wt %) |
|---|---|---|---|
| Particle Formulation 1 | 21.4 | — | — |
| Particle Formulation 2 | — | 11.73 | — |
| Particle Formulation 3 | — | — | 10.05 |
| Polyvinylpyrrolidone | 39.30 | 44.13 | 44.98 |
| Benzyl Benzoate | 39.30 | 44.13 | 44.98 |

Example 4

GLP-1(7-36)Amide Formulation

This example describes making a suspension formulation comprising a suspension vehicle and an GLP-1(7-36)amide particle formulation. A GLP-1(7-36)amide particle formulation was generated by spray-drying, and contained 90 wt % GLP-1, 5 wt % methionine and 5 wt % citrate buffer.

A suspension vehicle containing the polymer polyvinylpyrrolidone was dissolved in the solvent benzyl benzoate at approximately a 50/50 ratio by weight. The vehicle viscosity was approximately 12,000 to 18,000 poise when measured at 33° C. Particles containing the peptide GLP-1 (7-36)amide were dispersed throughout the vehicle at a concentration of 33% particles by weight.

Example 5

Co-Treatment of Prostate Cancer Using Leuprolide Acetate and Exenatide

Leuprolide acetate, an LHRH agonist, acts as a potent inhibitor of gonadotropin secretion when given continuously and in therapeutic doses. Animal and human studies indicate that following an initial stimulation, chronic administration of leuprolide acetate results in suppression of testicular steroidogenesis. This effect is reversible upon discontinuation of drug therapy. Administration of leuprolide acetate has resulted in inhibition of the growth of certain hormone-dependent tumors (prostatic tumors in Noble and Dunning male rats and DMBA-induced mammary tumors in female rats) as well as atrophy of the reproductive organs. In humans, administration of leuprolide acetate results in an initial increase in circulating levels of luteinizing hormone (LH) and follicle stimulating hormone (FSH), leading to a transient increase in levels of the gonadal steroids (testosterone and dihydrotestosterone in males). However, continuous administration of leuprolide acetate results in decreased level of LH and FSH. In males, testosterone is reduced to castrate levels. These decreases occur within two to six weeks after initiation of treatment, and castrate levels of testosterone in prostatic cancer patients have been demonstrated for multiyear periods. Leuprolide acetate is not active when given orally.

An implantable device containing leuprolide acetate for the treatment of prostate cancer is assembled as described in U.S. Pat. No. 5,728,396, incorporated herein by reference in its entirety. The device includes the following components:

Reservoir (Titanium, Ti6A 14V alloy) (4 mm outside diameter, 3 mm inside diameter)

Piston (C-Flex™)

Lubricant (silicone medical fluid) Compressed osmotic engine (76.4% NaCl, 15.5% sodium carboxymethyl cellulose, 6% povidone, 0.5% Mg Stearate, 1.6% water) PEG 400 (8 mg added to osmotic engine to fill air spaces) Membrane plug (polyurethane polymer, injection molded to desired shape) Back diffusion Regulating Outlet (polyethylene) Drug formulation (1) 0.150 g of 60% water and 40% leuprolide acetate; or (2) leuprolide acetate dissolved in DMSO to a measured content of 65 mg leuprolide.

To assemble the device, the piston and inner diameter of the reservoir are lightly lubricated. The piston is inserted about 0.5 cm into the reservoir at the membrane end. PEG 400 is added into the reservoir. Two osmotic engine tablets (40 mg each) are then inserted into the reservoir from the membrane end. After insertion, the osmotic engine is flush with the end of the reservoir. The membrane plug is inserted by lining up the plug with the reservoir and pushing gently until the retaining features of the plug are fully engaged in the reservoir. Formulation is loaded into a syringe which is then used to fill the reservoir from the outlet end by injecting formulation into the open tube until the formulation is about 3 mm from the end. The filled reservoir is centrifuged (outlet end "up") to remove any air bubbles that have been trapped in the formulation during filling. The outlet is screwed into the open end of the reservoir until completely engaged. As the outlet is screwed in, excess formulation exits out of the orifice ensuring a uniform fill.

These devices deliver about 0.35 μL/day leuprolide formulation containing on average 150 μg leuprolide in the amount delivered per day. They provide delivery of leuprolide at this rate for at least one year. The devices can achieve approximately 70% steady-state delivery by day 14.

Exenatide suspension formulations are produced as described in Example 1 and loaded into an implantable delivery device as above. Two implantable devices, one including an exenatide formulation and one including a leuprolide formulation are implanted under local anesthetic and by means of an incision in a patient suffering from advanced prostatic cancer. Implantation can be accomplished using, for example, an implanter device. See e.g., U.S. Pat. No. 6,190,350, incorporated herein by reference in its entirety. After an appropriate period of time, the implantable delivery devices are removed under local anesthetic. New devices may be inserted at that time.

7.0.0 Further Exemplary Embodiments of the Present Invention

Embodiments of the present invention include, but are not limited to, the following:

1. A method of treating cancer in a subject in need of such treatment, comprising: administering a GLP-1 receptor agonist to said subject.

2. The method of embodiment 1, wherein the GLP-1 receptor agonist is a small molecule.

3. The method of embodiment 1, wherein the GLP-1 receptor agonist is a peptide, polypeptide or protein.

4. The method of embodiment 3, wherein the GLP-1 receptor agonist is a glucagon-like peptide-1 (GLP-1), a derivative of GLP-1, or an analog of GLP-1.

5. The method of embodiment 4, wherein the GLP-1 receptor agonist is GLP(7-36)amide comprising the sequence of SEQ ID NO: 1.

6. The method of embodiment 3, wherein the GLP-1 receptor agonist is exenatide, a derivative of exenatide, or an analog of exenatide.

7. The method of embodiment 6, wherein the GLP-1 receptor agonist is synthetic exenatide peptide comprising the sequence of SEQ ID NO:2.

8. The method of embodiment 4, wherein the GLP-1 receptor agonist is selected from the group consisting of liraglutide, albiglutide, semaglutide and taspoglutide.

9. The method of embodiment 6, wherein the GLP-1 receptor agonist is lixisenatide.

10. The method of any one of embodiments 1-9, wherein the GLP-1 receptor agonist is provided in a suspension formulation comprising: (a) a particle formulation comprising said GLP-1 receptor agonist; and (b) a vehicle formulation, wherein the particle formulation is dispersed in the vehicle.

11. The method of embodiment 10, wherein (a) the particle formulation additionally comprises a disaccharide, methionine and a buffer and (b) the vehicle formulation is a non-aqueous, single-phase suspension vehicle comprising one or more pyrrolidone polymers and one or more solvents selected from the group consisting of lauryl lactate, lauryl alcohol, benzyl benzoate, and mixtures thereof; wherein the suspension vehicle exhibits viscous fluid characteristics, and the particle formulation is dispersed in the vehicle.

12. The method of embodiment 11, wherein the buffer is selected from the group consisting of citrate, histidine, succinate, and mixtures thereof.

13. The method of embodiment 12, wherein the buffer is citrate.

14. The method of embodiment 11, wherein the disaccharide is selected from the group consisting of lactose, sucrose, trehalose, cellobiose, and mixtures thereof.

15. The method of embodiment 11, wherein the particle formulation is a spray dried preparation of particles.

16. The method of embodiment 11, wherein the solvent is selected from the group consisting of lauryl lactate, benzyl benzoate, and mixtures thereof.

17. The method of embodiment 16, wherein the solvent consists essentially of benzyl benzoate.

18. The method of embodiment 11, wherein the pyrrolidone polymer consists essentially of polyvinylpyrrolidone.

19. The method of embodiment 11, wherein the vehicle consists essentially of a pyrrolidone polymer and benzyl benzoate.

20. The method of embodiment 19, wherein the vehicle is about 50% solvent and about 50% polymer.

21. The method of embodiment 11, wherein the suspension formulation has an overall moisture content of less than or equal to about 10 wt %.

22. The method of any one of embodiments 1-21, wherein the GLP-1 receptor agonist is delivered using an implantable osmotic delivery device.

23. The method of embodiment 22, wherein the osmotic delivery device provides continuous delivery of the GLP-1 receptor agonist for a period of at least one month.

24. The method of any one of embodiments 1-9, wherein the GLP-1 receptor agonist is provided in an injectable formulation.

25. The method of any one of embodiments 1-24, wherein a beneficial agent in addition to the GLP-1 receptor agonist is delivered to said subject.

26. The method of embodiment 25, wherein the additional beneficial agent is an anticancer agent.

27. The method of embodiment 26, wherein the anticancer agent is a chemotherapeutic agent.

28. The method of embodiment 26, wherein the anticancer agent is an anticancer antibody.

29. The method of any one of embodiments 25-28, wherein the additional beneficial agent is an antidiabetic agent.

30. The method of any one of embodiments 25-29, wherein the additional beneficial agent is delivered using an implantable osmotic delivery device.

31. The method of embodiment 30, wherein the osmotic delivery device provides continuous delivery of the GLP-1 receptor agonist for a period of at least one month.

32. The method of either one of embodiments 30 or 31, wherein the additional beneficial agent is a luteinizing hormone-releasing hormone (LHRH) agonist.

33. The method of any one of embodiments 25-29, wherein the additional beneficial agent is provided in an injectable formulation.

34. The method of any one of embodiments 25-29, wherein the additional beneficial agent is provided in an oral formulation.

35. The method of embodiment 25, wherein the additional beneficial agent is GIP.

36. The method of any one of embodiments 25-35, wherein the additional beneficial agent is delivered prior to the GLP-1 receptor agonist.

37. The method of any one of embodiments 25-35, wherein the additional beneficial agent is delivered subsequent to the GLP-1 receptor agonist.

38. The method of any one of embodiments 25-35, wherein the additional beneficial agent is delivered concurrent with the GLP-1 receptor agonist.

As is apparent to one of skill in the art, various modification and variations of the above embodiments can be made without departing from the spirit and scope of this invention. Such modifications and variations are within the scope of this invention.

What is claimed is:

1. An implantable osmotic delivery device comprising a suspension formulation, the suspension formulation comprising: (a) a particle formulation comprising semaglutide, sucrose and methionine, the particle formulation having a ratio of semaglutide:(sucrose+methionine) of from about 2:1 to about 20:1, and (b) a non-aqueous vehicle formulation, wherein the particle formulation is dispersed in the non-aqueous vehicle formulation.

2. The implantable osmotic delivery device of claim 1, wherein the particle formulation additionally comprises: a buffer selected from the group consisting of citrate, histidine, succinate, and mixtures thereof; the particle formulation is a spray dried preparation of particles, and the suspension formulation has an overall moisture content of less than or equal to about 10 wt %.

3. The implantable osmotic delivery device of claim 1, wherein (a) the particle formulation additionally comprises a buffer and (b) the vehicle formulation is a single-phase suspension vehicle comprising one or more pyrrolidone polymers and one or more solvents selected from the group consisting of lauryl lactate, lauryl alcohol, benzyl benzoate, and mixtures thereof.

4. The implantable osmotic delivery device of claim 3, wherein the buffer is selected from the group consisting of citrate, histidine, succinate, and mixtures thereof.

5. The implantable osmotic delivery device of claim 1, wherein the particle formulation is a spray dried preparation of particles.

6. The implantable osmotic delivery device of claim 1, wherein the vehicle consists essentially of polyvinylpyrrolidone and benzyl benzoate.

7. The implantable osmotic delivery device of claim 1, wherein the vehicle is about 50% solvent and about 50% polymer.

8. The implantable osmotic delivery device of claim 1, wherein the suspension formulation has an overall moisture content of less than or equal to about 10 wt %.

* * * * *